(12) United States Patent
Bouillot et al.

(10) Patent No.: US 8,557,984 B2
(45) Date of Patent: Oct. 15, 2013

(54) IMIDAZO [4, 5-C] QUINOLINE DERIVATIVES AS BROMODOMAIN INHIBITORS

(75) Inventors: Anne Marie Jeanne Bouillot, Les Ulis (FR); Frederic Donche, Les Ulis (FR); Francoise Jeanne Gellibert, Les Ulis (FR); Yann Lamotte, Les Ulis (FR); Olivier Mirguet, Les Ulis (FR)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/503,722

(22) PCT Filed: Nov. 3, 2010

(86) PCT No.: PCT/EP2010/066699
§ 371 (c)(1),
(2), (4) Date: Apr. 24, 2012

(87) PCT Pub. No.: WO2011/054846
PCT Pub. Date: May 12, 2011

(65) Prior Publication Data
US 2012/0232074 A1    Sep. 13, 2012

(30) Foreign Application Priority Data
Nov. 5, 2009   (GB) .................................. 0919423.4

(51) Int. Cl.
*C07D 471/04*    (2006.01)
*C07D 471/14*    (2006.01)

(52) U.S. Cl.
USPC .............. 544/126; 544/333; 544/405; 546/82

(58) Field of Classification Search
None
See application file for complete search history.

(56) References Cited

U.S. PATENT DOCUMENTS

2004/0147543 A1    7/2004   Hays et al.

FOREIGN PATENT DOCUMENTS

WO    WO 2007/075468         7/2007
WO    2009084693 A1          7/2009

OTHER PUBLICATIONS

Zeng, L., & Zhou, M., Bromodomain: An Acetyl-Lysine Binding Domain, 513 FEBS Letts. 124-128 (2002).*

* cited by examiner

*Primary Examiner* — Janet L. Andres
*Assistant Examiner* — Timothy R Rozof
(74) *Attorney, Agent, or Firm* — Robert H. Brink

(57) ABSTRACT

Novel compounds of formula (I)

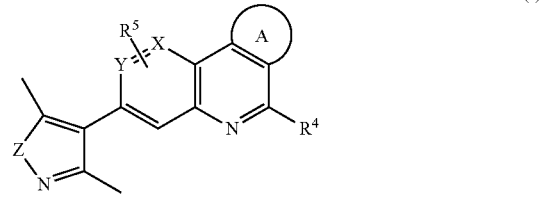

and salts thereof, pharmaceutical compositions containing such compounds and their use in therapy.

17 Claims, No Drawings

IMIDAZO [4, 5-C] QUINOLINE DERIVATIVES AS BROMODOMAIN INHIBITORS

CROSS-REFERENCE TO RELATED APPLICATIONS

This application is filed pursuant to 35 USC 371 as a United States National Phase Application of International Patent Application Serial No. PCT/EP2010/066699 filed on Nov. 3, 2010, which claims priority from 0919423.4 filed on Nov. 5, 2009 in the United Kingdom.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693A1 discloses a series of thienotriazolodiazepiene derivatives that are said to inhibit the binding between an acetylated histone and a bromodomain containing protein which are said to be useful as anti-cancer agents.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof.

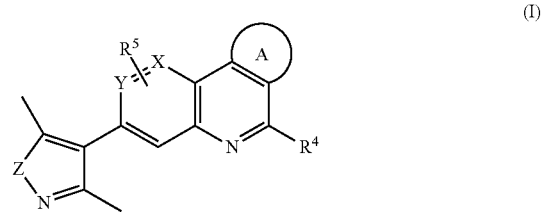

(I)

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof

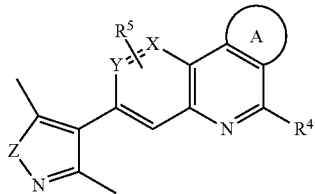

(I)

wherein:
A is a group selected from the following:

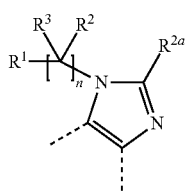

(i)

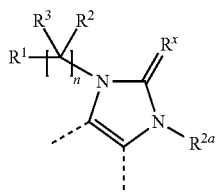

(ii)

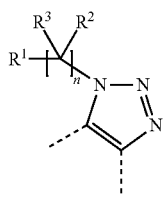

(iii)

X represents CH or N;
Y represents CH or N with the proviso that when X is N, Y is CH;
$R^x$ represents O or S;
$R^1$ represents $C_{1-6}$alkyl, $C_{3-6}$cycloalkyl, a 5- or 6-membered heterocyclyl, an aromatic group or a heteroaromatic group, wherein the aromatic group or the heteroaromatic group is optionally substituted by one to three groups selected from:
  halogen, hydroxy, cyano, nitro, $C_{1-6}$alkyl, $C_{1-4}$alkoxy, halo$C_{1-4}$alkyl, halo$C_{1-4}$alkoxy, hydroxy$C_{1-4}$alkyl, $C_{1-4}$alkoxy$C_{1-4}$alkyl, $C_{1-4}$alkoxycarbonyl, $C_{1-4}$alkylsulfonyl, $C_{1-4}$alkylsulfonyloxy, $C_{1-4}$alkylsulfonyl-$C_{1-4}$alkyl and $C_{1-4}$alkylsulfonamido;
$R^2$ is hydrogen or $C_{1-6}$alkyl,
$R^{2a}$ represents:
  H, $C_{1-6}$alkyl, $C_{1-6}$ haloalkyl, $(CH_2)_m$cyano, $(CH_2)_m$OH, $(CH_2)_m C_{1-6}$alkoxy, $(CH_2)_m C_{1-6}$ haloalkoxy, $(CH_2)_m C_{1-6}$ haloalkyl $(CH_2)_m C(O)NR^a R^b$, $(CH_2)_m NR^a R^b$, $(CH_2)_m C(O)CH_3$,
  $(CHR^6)_p$phenyl optionally substituted by $C_{1-6}$alkyl, $C_{1-6}$alkoxy, cyano halo$C_{1-4}$alkoxy, halo$C_{1-4}$alkyl, $(CHR^6)_p$ heteroaromatic or $(CHR^6)_p$ heterocyclyl,
  wherein
  $R^a$ represents H, $C_{1-6}$alkyl, or heterocyclyl;
  $R^b$ represents H or $C_{1-6}$alkyl, or
  $R^a$ and $R^b$ together with the N to which they are attached form a 5- or 6-membered heterocyclyl;
$R^{2b}$ represents H, $C_{1-6}$alkyl, $(CH_2)_2 C_{1-6}$alkoxy, $(CH_2)_2$cyano or $(CH_2)_m$phenyl, $(CH_2)_2$ heterocyclyl;
$R^3$ represents hydrogen;
$R^4$ represents hydrogen, cyano or $C_{1-6}$alkyl;
Z represents O; or when $R^4$ represents hydrogen and A is a group selected from (i) or (ii) and wherein $R^x$ represents O, Z may additionally represent NH;
$R^5$ represents hydrogen or $C_{1-6}$alkoxy;
$R^6$ represents hydrogen or $C_{1-6}$alkyl;
m represents 1, 2 or 3;
n represents 0, 1 or 2; and
p represents 0, 1 or 2.

As used herein, the term "aromatic group" refers to a 5- to 7-membered monocyclic aromatic group such as phenyl, or a 8- to 11-membered bicyclic aromatic group such as naphthyl, indenyl or azulenyl.

As used herein heterocyclyl refers to a 5- or 6-membered non-aromatic, saturated or unsaturated ring comprising 1, 2, or 3 heteroatoms selected from O, N and S. Examples of heterocyclyls include morpholinyl, piperidinyl, tetrahydropyranyl, and piperazinyl.

As used herein, the term "heteroaromatic group" refers to a 5- or 6-membered monocyclic aromatic group wherein 1, 2, 3, 4 of the carbon atoms are replaced by a heteroatom independently selected from O, S and N; or to a 8- to 11-membered bicyclic aromatic group wherein 1, 2, 3, 4 or 5 of the carbon atoms are replaced by a heteroatom independently selected from O, S and N.

Examples of 5- or 6-membered monocyclic heteroaromatic groups include pyrrolinyl, furanyl, thienyl, pyrrolyl, oxazolyl, thiazolyl, imidazolyl, oxadiazolyl, thiadiazolyl, pyridinyl, triazolyl, triazinyl, pyridazyl, pyrimidinyl, isothiazolyl, isoxazolyl, pyrazinyl, pyrazolyl and pyrimidinyl. Examples of 8- to 11-membered bicyclic heteroaromatic groups include 6H-thieno[2,3-b]pyrrolyl, imidazo[2,1-b][1,3]thiazolyl, imidazo[5,1-b][1,3]thiazolyl, indolyl, isoindolyl, indazolyl, benzimidazolyl, [1,3]thiazolo[3,2-b][1,2,4]triazolyl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

Examples of $C_{3-6}$cycloalkyls include cyclopropyl, cyclobutyl, cyclopentyl and cyclohexyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "halogen" refers to the elements fluorine, chlorine, bromine and iodine, for example, fluorine, chlorine and bromine.

As used herein, the term "substituted" refers to substitution with the named substituent or substituents, multiple degrees of substitution being allowed unless otherwise stated. When the substituent is on a ring comprising a heteroatom the substituent may be located on a carbon or a heteroatom, if the latter is appropriate.

In one embodiment, X is CH.

In one embodiment Y is CH.

In one embodiment Z is O.

In another embodiment Z is NH (and in consequence $R^4$ represents hydrogen, A is a group selected from (i) or (ii) as defined above, and $R^x$ represents O).

In one embodiment $R^x$ is O.

In one embodiment n is 0 or 1, such as 1.

In one embodiment, A is a group of formula (i) or (ii) as described above.

Representative examples of $R^1$ include, pyridinyl such as pyridin-2-yl, phenyl optionally substituted by 1 or 2 groups such as 1 substitutent, wherein said substituents are independently selected from methyl, t-butyl, fluoro, chloro, and —$OCF_3$. Optional substituents on the phenyl may, for example, be in the ortho or para position.

In one embodiment $R^1$ is a heteroaromatic group optionally substituted by one or two groups selected from hydroxy, $C_{1-3}$alkyl, $C_{1-3}$alkoxy, hydroxy$C_{1-4}$alkyl and $C_{1-4}$alkoxy$C_{1-4}$alkyl. In one embodiment the heteroaromatic group is pyridyl. In a further embodiment the heteroaromatic group is selected from furanyl, thienyl, isoxazolyl, thiazolyl, pyrazolyl, pyrazinyl and pyrimidinyl.

In one embodiment, n is 0 and $R^1$ is phenyl substituted by $C_{1-6}$alkyl (such as phenyl substituted by t-butyl), or phenyl substituted by halo$C_{1-6}$alkoxy (such as $OCF_3$).

In one embodiment n is 1 and $R^1$ is unsubstituted phenyl.

In one embodiment n is 1 or 2 such as 1 and $R^1$ is phenyl optionally substituted by, for example 1 or 2 halogens such as chlorine, and/or fluoro.

In one embodiment $R^2$ is hydrogen or methyl.

In one embodiment $R^{2a}$ is H, $C_{1-3}$alkyl, $(CH_2)_m$OH, $(CH_2)_mC_{1-3}$alkoxy, $(CH_2)_mNR^aR^b$ or $(CHR^6)_p$ heterocyclyl, wherein $R^a$ represents H, $C_{1-3}$alkyl, or heterocyclyl;

$R^b$ represents H or $C_{1-3}$alkyl, or $R^a$ and $R^b$ together with the N to which they are attached form a 5 or 6 membered heterocyclyl;

$R^6$ represents H or $C_{1-3}$alkyl;

m represents 1, 2 or 3; and p represents 0, 1, 2.

In one embodiment, $R^{2a}$ is hydrogen, $C_{1-6}$alkyl such as methyl, isopropyl or t-butyl or $C_{1-6}$alkoxy$C_{1-6}$alkyl such as —$(CH_2)_2OCH_3$.

In one embodiment $R^{2a}$ is tetrahydropyranyl.

In one embodiment $R^{2b}$ is hydrogen.

In one embodiment $R^{2b}$ is $(CH_2)_2C_{1-6}$alkoxy such as $(CH_2)_2$OMe.

In one embodiment $R^a$ and $R^b$ together with the N to which they are attached form a 5 or 6 membered heterocyclyl such as morpholine, piperidine or pyrrolidine.

In one embodiment $R^4$ is hydrogen.

In one embodiment, $R^5$ is hydrogen or —$OCH_3$ such as —$OCH_3$.

In one embodiment X is CH, Y is CH and $R^5$ is —$OCH_3$, for example in the 8 position.

In one embodiment X is N, Y is CH and $R^5$ is —$OCH_3$, for example in the 8 position In one embodiment, the compounds of the present invention have a formula (IA):

(IA)

wherein A and $R^4$ are as defined for formula (I).

In one embodiment, the compounds of the present invention have the formula (IB):

(IB)

wherein $R^1$, $R^2$, $R^3$, $R^5$ and n are as defined for compounds of formula (I).

In this aspect of the invention n may, for example, represent 1.

In this aspect of the invention $R^1$ may represent, for example pyridinyl such as pyridin-2-yl or phenyl.

In this aspect of the invention $R^5$ may represent, for example, —$OCH_3$.

In one embodiment, compounds of the invention have the formula (IC)

(IC)

wherein $R^1$, $R^2$, $R^3$, $R^{2a}$ and n are defined above for compounds of formula (I).

It is to be understood that the present invention covers all combinations of suitable, convenient and preferred groups described herein above. Thus all features and embodiments of formula (I) may apply to formula (IA), (IB) and (IC).

Specific compounds of formula (I) include Examples 1-226 as described herein or a salt thereof, in particular a pharmaceutically acceptable salt thereof.

In one embodiment there is provided a compound which is 7-(3,5-dimethyl-4-isoxazolyl)-8-(methyloxy)-1-[(1R)-1-(2- pyridinyl)ethyl]-1,3-dihydro-2H-imidazo[4,5-c]quinolin-2-one or a salt thereof. In another embodiment there is provided a compound which is 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one or a pharmaceutically acceptable salt thereof. In another embodiment there is provided a compound which is 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. As used herein, the term 'pharmaceutically acceptable salt' means any pharmaceutically acceptable salt or solvate of a compound of formula (I), which upon administration to the recipient is capable of providing (directly or indirectly). In one embodiment, the term 'pharmaceutically acceptable salt' means any pharmaceutically acceptable salt of a compound of formula (I), which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognizable to those skilled in the art, without undue experimentation. Nevertheless, reference is made to the teaching of Burger's Medicinal Chemistry and Drug Discovery, $5^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain compounds described herein may contain one or more chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Any previously defined variable will continue to have the previously defined meaning unless otherwise indicated. Illustrative general synthetic methods are set out below and then specific compounds of formula (I) and pharmaceutically acceptable salts thereof, are prepared in the working Examples. These processes form further aspects of the present invention.

Throughout the specification, general formulae are designated by Roman numerals (I), (II), (III), (IV) etc.

In another aspect, the present invention provides a process for the preparation of a compound of formula (I) wherein Z represents O, the process comprising the step of reacting a compound of formula (II):

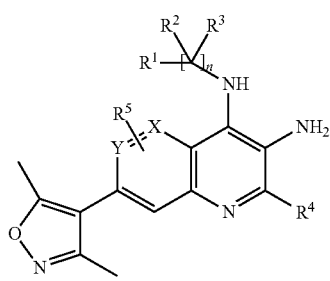

(II)

wherein X, Y, $R^1$, $R^2$ and $R^3$ are as defined for compounds of formula (I) with:
a) $R^{2a}$COOH, $R^{2a}$CHO or $R^{2a}$COCl, wherein $R^{2a}$ is as defined above for compounds of formula (I), or
b) (t-butylOCO)$_2$O, or
c) CS$_2$, or
d) NaNO$_2$,
under appropriate conditions.

Step a) may be effected by refluxing in a suitable solvent such as acetic acid.

When $R^{2a}$COOH is the reagent, prior to refluxing in acetic acid, activation of the starting material with a reagent such as HOBT may be required. The coupling reaction may be performed in the presence of a coupling agent such as EDCl and an organic base such as triethylamine, in a suitable solvent, for example a polar aprotic solvent such as dichloromethane.

When an acid chloride $R^{2a}$COCl is employed, prior to refluxing in acetic acid, the acid chloride is allowed to react with the compound of formula (II) in a suitable solvent, for example a polar aprotic solvent such as dichloromethane in the presence of an organic base such as triethylamine.

Step b) may be performed at 80° C. for a period of about 2 h, followed by treatment at an elevated temperature, for example, 180° C. for a period of about 3 h in a solvent such as diphenylether.

Step c) may be effected at elevated temperatures, for example above 50° C. such as 80° C., under basic conditions, for example in the presence of triethylamine in a suitable solvent, for example an alcohol such as ethanol.

Step d) may be effected at low temperature, for example sodium nitrite is added at 0° C., after which the reaction mixture is allowed to warm to room temperature and continue reacting for about 18 h.

In the schemes below X, Y, $R^1$, $R^2$, $R^3$, n etc have the definitions as given above for compounds of formula (I).

Compounds of formula (I) wherein $R^4$ represents H or alkyl and A is an imidazole derivative can be prepared as shown in Scheme 1 below.

Scheme 1

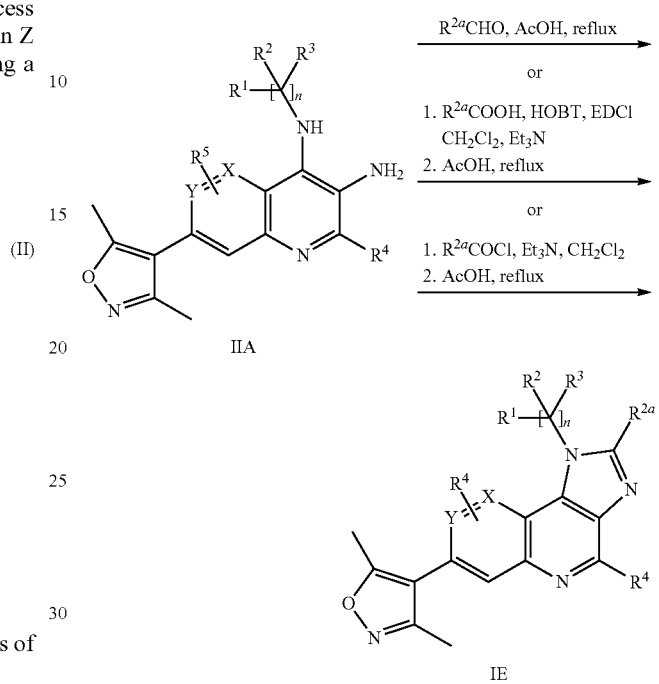

The imidazole derivatives of general formula (IE) may be prepared (scheme 1) by reacting the amino derivatives (IIA) with aldehydes ($R^2$CHO) in acetic acid at reflux, or by coupling the derivatives (IIA) with carboxylic acid of general formula $R^2$COOH with HOBT, EDCl in dichloromethane in presence of triethylamine, followed by cyclisation in acetic acid at reflux, or by coupling with acid chloride of general formula $R^2$COCl in presence of triethylamine followed by cyclisation in acetic acid at reflux.

Compounds of formula (I) wherein $R^4$ represents H or alkyl, and A represents an imidazolone can be prepared as shown in Scheme 2 below.

Scheme 2

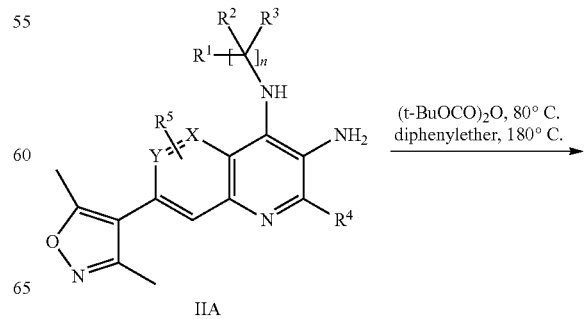

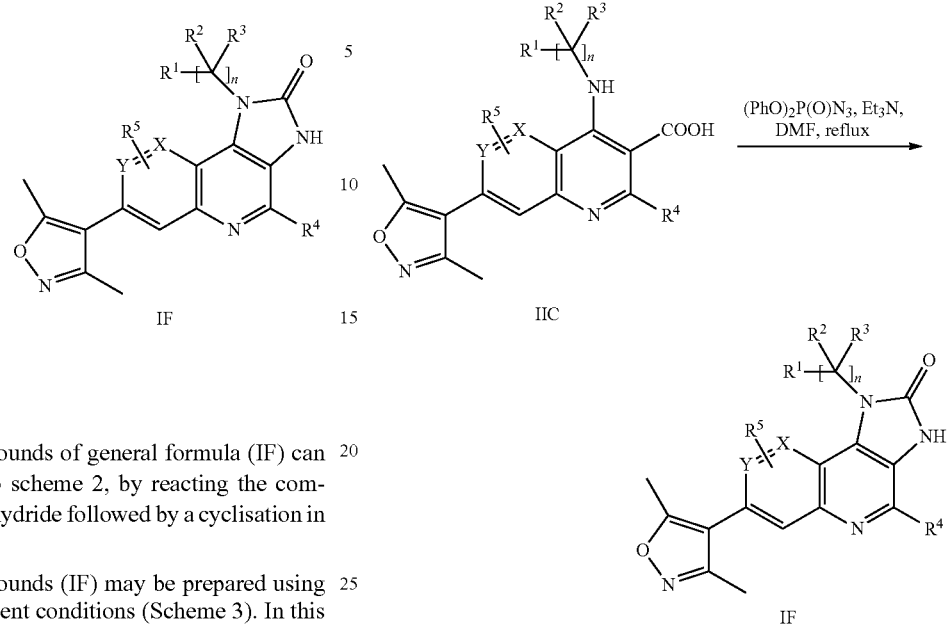

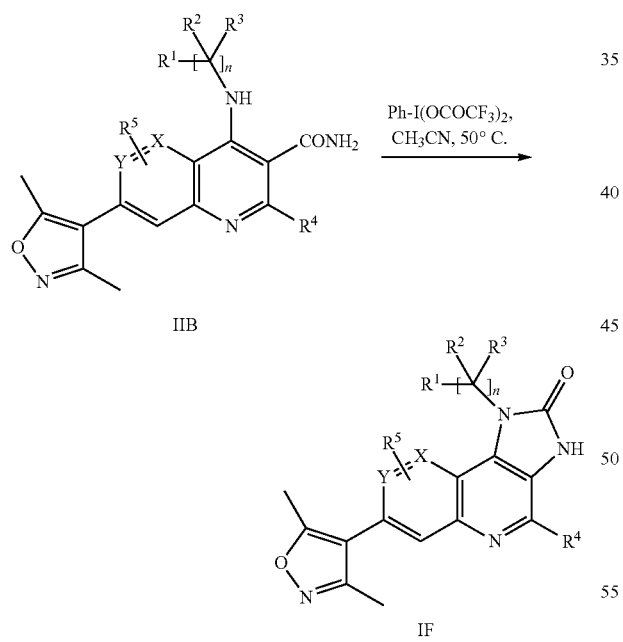

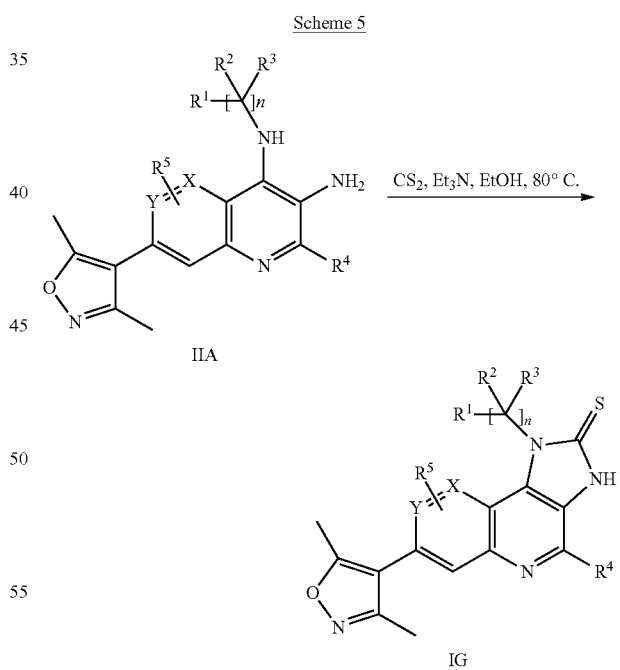

The imidazolone compounds of general formula (IF) can be prepared, according to scheme 2, by reacting the compounds (IIA) with Boc anhydride followed by a cyclisation in diphenyl ether at 180° C.

The imidazolone compounds (IF) may be prepared using Hoffman-type rearrangement conditions (Scheme 3). In this case the compounds (IIB) are reacted with bis(trifluoroacetoxy)iodo]benzene, to give after internal cyclisation the imidazolone compounds (IF).

Compounds of formula (I) wherein $R^4$ is H, and A is an imidazol-2-thione derivative can be prepared as shown in Scheme 5 below.

The imidazolone compounds (IF) may also be prepared using Curtius rearrangement conditions (Scheme 4). In this case the acid compounds (IIC) are reacted with diphenyl phosphoryl azide in the presence of triethylamine for a period of approximately 2 to 18 h to give the imidazolone compounds (IF).

The imidazol-2-thione derivatives of general formula (IG) can be prepared by reacting the compounds of general formula (IIA) with carbon disulfide in the presence of triethylamine in a solvent such as ethanol at 60°-80° C. for approximately 18 h.

Compounds of formula (I) wherein $R^4$ is H or alkyl, and A is a triazole derivative can be prepared as shown in Scheme 6 below. The amino derivative (IIA) is reacted at at 0° C. with sodium nitrite in water and acetic acid in a solvent as DMF. The reaction mixture is then stirred at room temperature for approximately 18 h.

Scheme 6

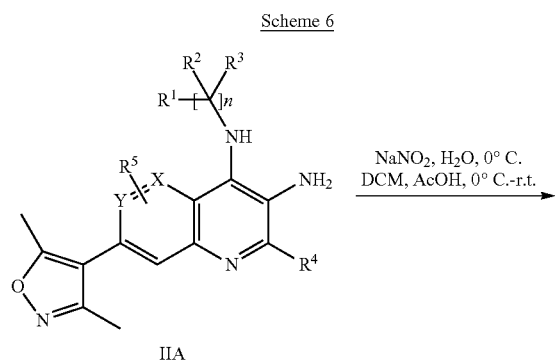

Compounds of formula (I) wherein $R^4$ is cyano and A is an imidazole derivative can be prepared as shown in Scheme 7 below, using modified a Reissert-Henze reaction (Harusawa, S et al., *Heterocycles*, 1981, 15, 981-984). Compound (IE) is reacted with m-chloroperbenzoic acid in dichloromethane at room temperature for approximately 2 h. The resulting N-oxide intermediate is then reacted with diethyl phosphorocyanidate in the presence of triethylamine in an amprotic solvent such as acetonitrile, the reaction mixture is then heated under reflux for 4 h.

Scheme 7

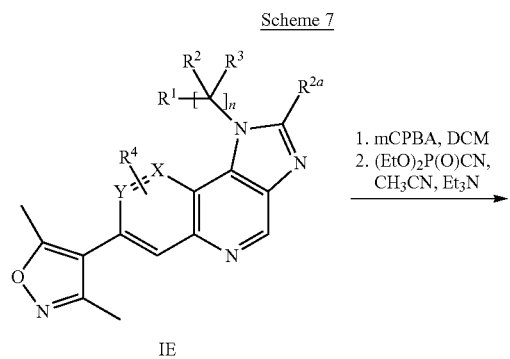

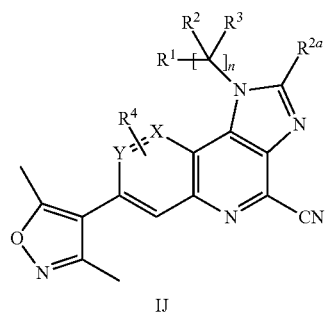

The starting material (1E) in Scheme 7 can be prepared by an analogous method to that described above in Scheme 1.

Compounds of general formula (IIA) wherein $R^4$ is hydrogen and alkyl may be prepared according to Scheme 8. Compounds (IIIA) are reacted with sodium hydroxide in ethanol under reflux for 5 h. After treatment with HCl N, the resulting compounds of general formula (VA) are de-carboxylated in diphenylether under reflux for 2 h. Nitration of compounds (VA) is preformed with nitric acid in propanoic acid at room temperature, followed by heating the reaction mixture to a range of temperature 100-125° C. for 1 to 2 h. Compounds (VIA) are reacted with $POCl_3$ in toluene under reflux for approximately 18 h. The chloro compounds (VIIA) are then reacted with amines of general formula $R^1(R^2R^3C)_nNH_2$ in a solvent such as acetonitrile at 60° C. for 2 h. The resulting compounds may then be reduced with $SnCl_2,2H_2O$ in ethanol/HCl or ethanol/THF at a temperature in the range 40° C. to reflux for approximately 1 to 3 h, to give compounds of general formula (IIA).

Scheme 8

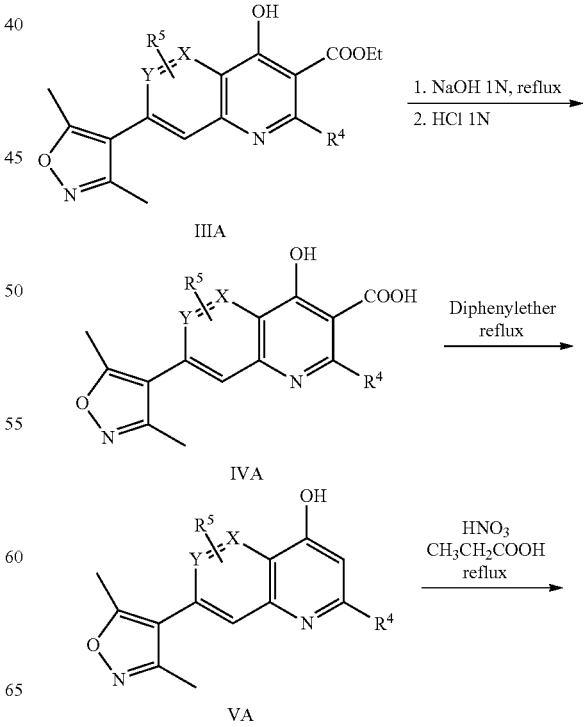

-continued

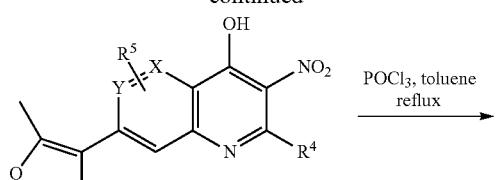

VIA

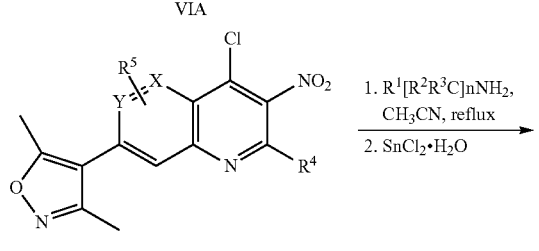

VIIA

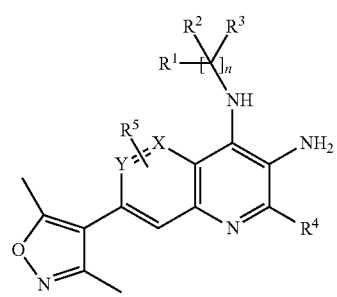

IIA

Compounds of general formula (VA) wherein X and Y are CH and R⁴ is hydrogen may be also prepared according to Scheme 9.

Scheme 9

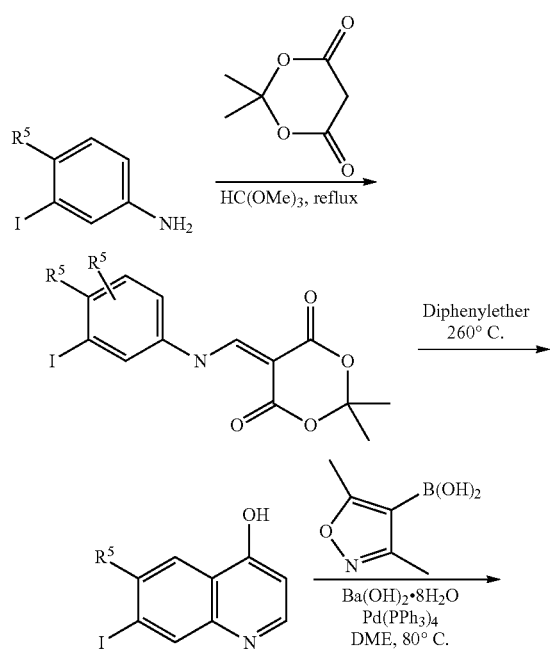

-continued

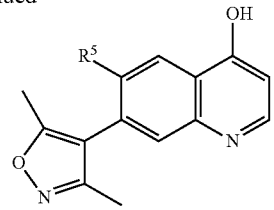

VA

The 3-iodo aniline derivatives are reacted meldrum's acid in presence of methyl orthoformate under reflux for approximately 1 h, followed by cyclisation in boiling diphenylether for approximately 10 minutes. Compounds of general formula (VA) wherein R⁴ is alkyl, for example methyl, may be prepared following the same synthetic route by replacing meldrum's acid by ethyl acetoacetate.

Compounds of formula VA wherein R⁵ is situated at a different position on the ring can be prepared by a method analogous to that set out in Scheme 8, starting from appropriate starting materials.

Compounds of general formula (IIB) wherein R⁴ is hydrogen or alkyl may be prepared according to Scheme 10. Compounds (IVA) are treated with POCl₃ with DMF under reflux. The corresponding 4-chloro-3-chloroacyl derivatives are then reacted with ammonia$_{(g)}$ at 0°-5° C. in a solvent such as dioxane to afford the carboxamide compounds (VIIIA). Coupling with the amine was performed as previously described for Scheme 8.

Scheme 10

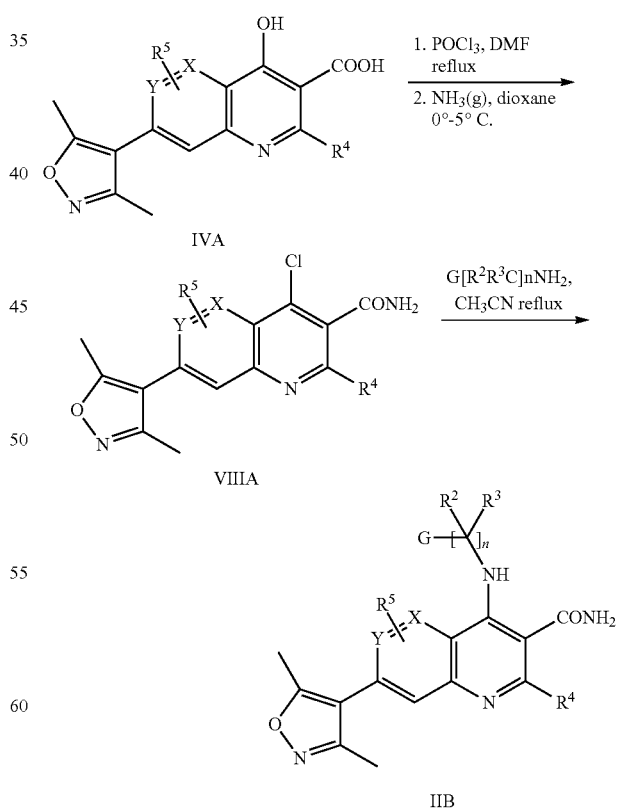

Compounds of general formula (IIIA), wherein R⁴ is hydrogen may be prepared according to Scheme 11.

Scheme 11

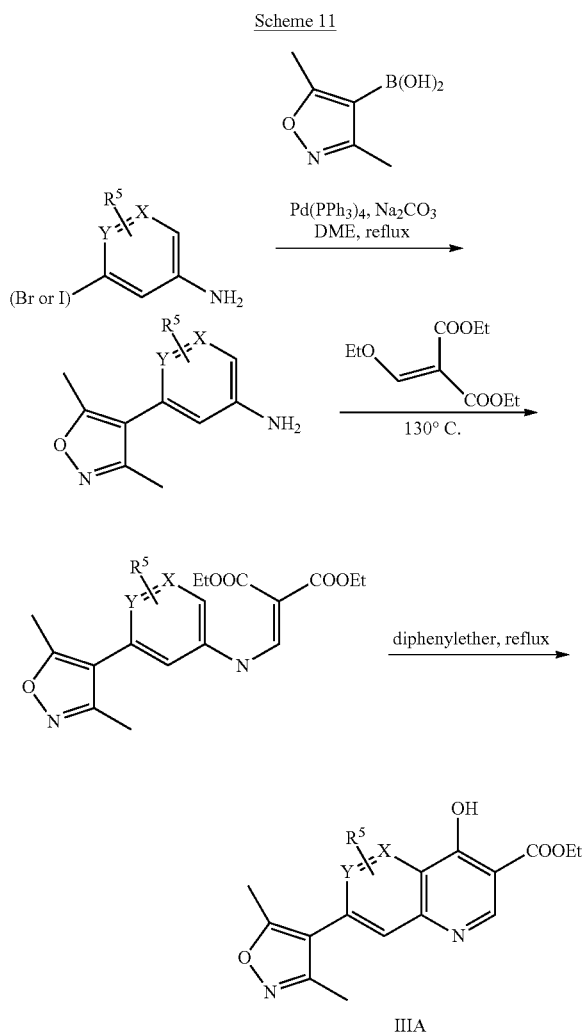

Scheme 12

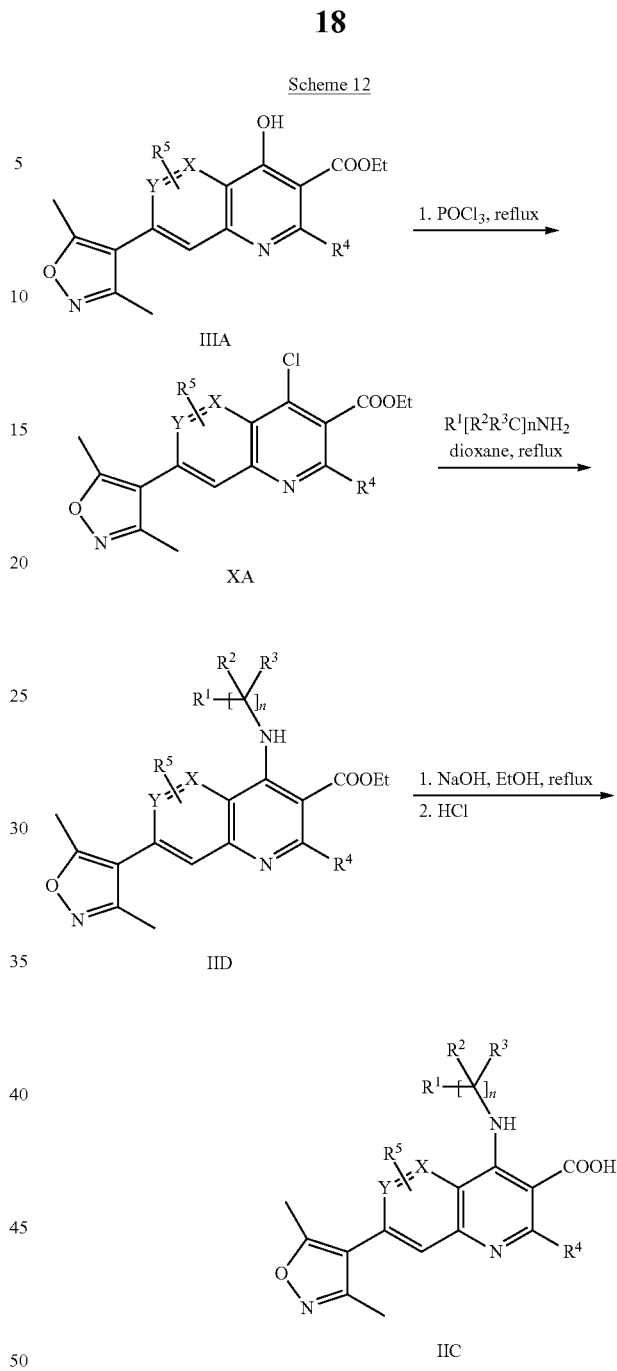

The 3,5-dimethylisoxazole boronic acid may be reacted with 3-iodo or 3-bromo derivatives using Suzuki coupling conditions to give the corresponding amino compounds. When X and Y are CH, the 3-(3,5-dimethyl-4-isoxazolyl) aniline may be reacted with diethyl ethoxymethylenemalonate at 130° C. of a period in the range 20 minutes to 1 h. The resulting diethyl ({[3-(3,5-dimethyl-4-isoxazolyl)phenyl]amino}methylidene)-propanedioate may be cyclised in diphenylether by refluxing for approximately 30 minutes to 1 h (according to the standard procedure described in J. Med. Chem., 1980, 23, 1358). The same procedure may be applied to aminopyridine compounds to prepare the 1,5- or 1,6-naphthyridine compounds.

Compounds of formula (I) wherein $R^4$ is alkyl, for example methyl, can be prepared by analogous methods to those described Scheme 11 replacing diethyl ethoxymethylenemalonate by diethyl acetylmalonate.

Compounds of general formula (IIC), wherein $R^4$ is hydrogen or alkyl may be prepared according to Scheme 12.

Compounds (IIIA) are refluxed in $POCl_3$ for approximately 18 h, and compounds (XA) are then coupled with amines of general formula $R^1(R^2R^3C)_nNH_2$ in a solvent such as acetonitrile or dioxane at a temperature in the range 60° to 110° C. for approximately 1 to 4 h. Saponification of compounds (IID) with NaOH(N) in Ethanol heated to reflux, for approximately 6 to 24 h, affords compounds of formula (IIC).

Compounds of formula (I) wherein Z represents NH (and in consequence $R^4$ represents hydrogen, A is a group selected from (i) or (ii) as defined above, and $R^x$ represents O) can be prepared according to processes as shown in Schemes 13 to 15 below.

Scheme 13
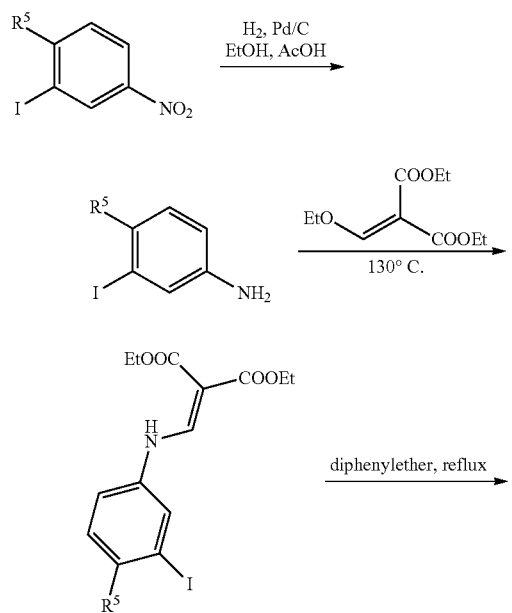
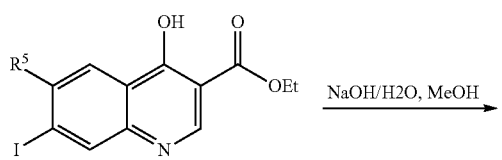
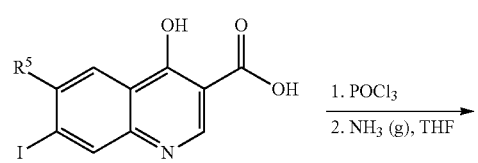
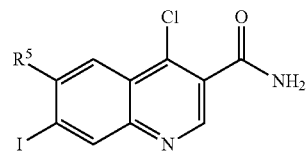
Scheme 14
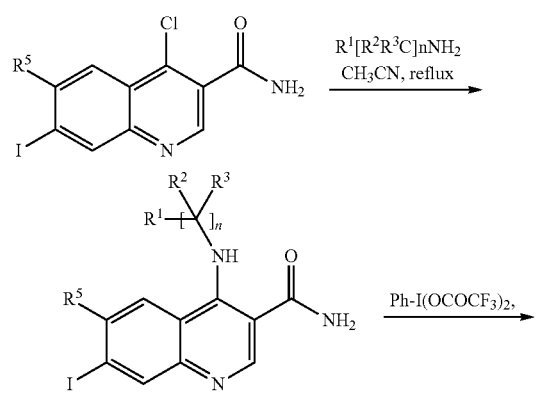
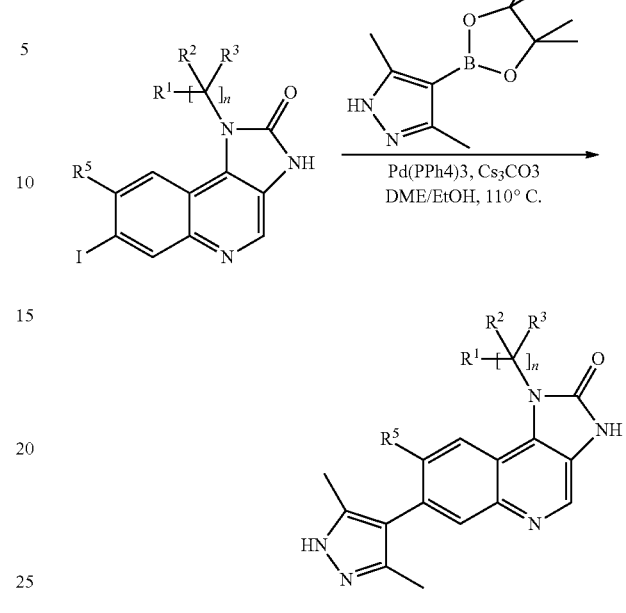
Scheme 15
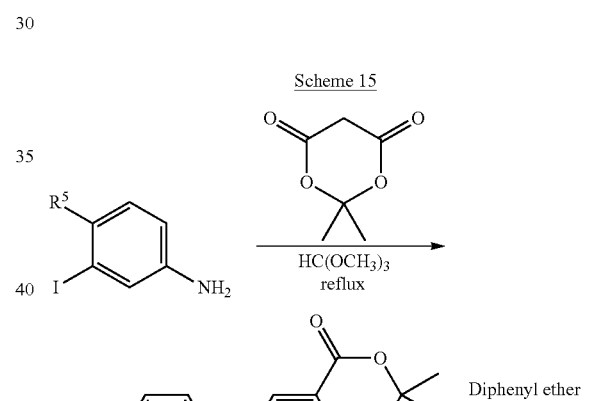
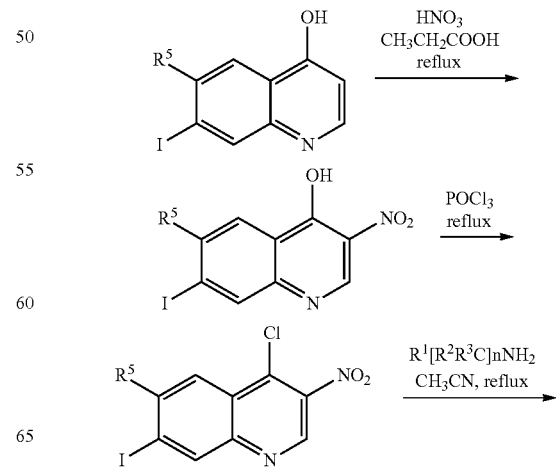

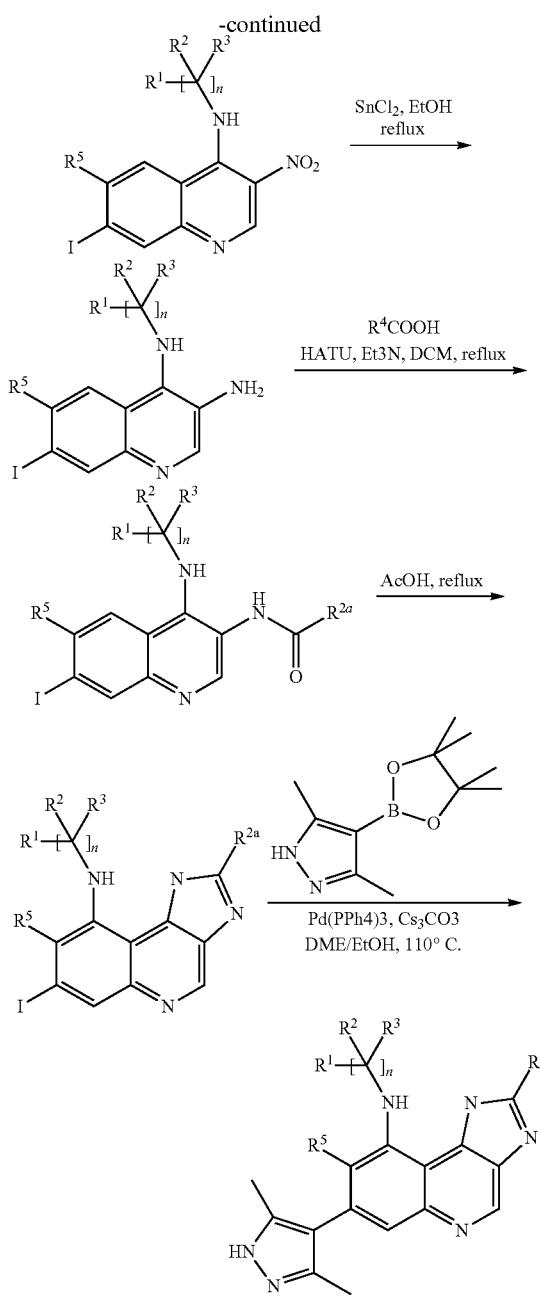

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. In one embodiment there is provided 7-(3,5-dimethyl-4-isoxazolyl)-8-(methyloxy)-1-[(1R)-1-(2-pyridinyl) ethyl]-1,3-dihydro-2H-imidazo[4,5-c]quinolin-2-one or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In another embodiment there is provided a compound or a pharmaceutically acceptable salt thereof for use in the treatment of chronic autoimmune and/or inflammatory conditions. In a further embodiment there is provided a compound or a pharmaceutically acceptable salt thereof for use in the treatment of cancer.

In one embodiment there is provided 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one or a pharmaceutically acceptable salt thereof for use in the treatment of diseases or conditions for which a bromodomain inhibitor indicated.

Also provided is the use of a compound of formula (I) or a pharmaceutically acceptable salt thereof in the manufacture of a medicament for the treatment of diseases or conditions for which a bromodomain inhibitor is indicated. In one embodiment there is provided 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating diseases or conditions for which a bromodomain inhibitor is indicated in a subject in need thereof which comprises administering a therapeutically effective amount of 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include each of or all of the above disease states.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

In one embodiment there is provided a pharmaceutical composition comprising 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one or a pharmaceutically acceptable salt and one or more or pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof, can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof, and may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof, and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other pharmaceutically active agent(s) and the relative timings of administration will be selected in order to achieve the desired combined therapeutic effect. Thus in a further aspect, there is provided a combination comprising a compound of formula (I) or a pharmaceutically acceptable salt thereof, and at least one other pharmaceutically active agent.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists and beta-2 agonists.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

INTERMEDIATES AND EXAMPLES

The following non-limiting Examples illustrate the present invention.

| Abbreviations | |
|---|---|
| TLC | thin layer chromatography |
| AcOH | acetic acid |
| DCM | dichloromethane |
| DME | 1,2-dimethoxyethane |
| DMF | N,N-dimethylformamide |
| HOBT | 1-(hydroxy)benzotriazole |
| EDCI | 1-ethyl-3-(3-dimethylaminopropyl)-carbodimide |
| diethyl ether | diethyl ether |
| EtOAc | ethyl acetate |
| i-Pr$_2$O | di-isopropyl ether |
| Config. | absolute configuration |
| CH$_3$CN | acetonitrile |
| MeOH | methanol |
| THF | tetrahydrofuran |
| RT | room temperature |
| Rt | retention time |
| DIEA | N,N-diisopropylethylamine |
| APCI MS | Atmospheric Pressure Chemical Ionization quadrupole Mass Spectrometer |
| CS$_2$ | carbon disulfide |
| Na$_2$CO$_3$ | sodium carbonate |
| NaHCO$_3$ | sodium hydrogen carbonate |
| NaNO$_2$ | sodium nitrite |
| NaOH | sodium hydroxide |
| Na$_2$SO$_4$ | sodium sulfate |
| POCl$_3$ | Phosphorus (III) oxychloride |
| Ba(OH)$_2$·8H$_2$O | Barium hydroxide octahydrate |

-continued

| Abbreviations | |
|---|---|
| SnCl$_2$, 2H$_2$O | Tin (II) chloride dihydrate |
| Pd/C | Palladium on carbon |
| mCPBA | m-chloroperbenzoic acid |
| CDCl$_3$ | deuterated chloroform |
| DMSO d6 | deuterated dimethylsulfoxide |
| BOC | tert-butyloxycarbonyl |
| N | 1 Normal (concentration) |
| PEPPSI ™ | Pyridine-Enhanced Precatalyst Preparation Stabilization and Initiation |

Analytical HPLC was conducted on two kinds of apparatus:
a) On a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 ml/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES−ve to give [M−H]− molecular ion] modes. Analytical data from this apparatus are given with the following format: [M+H]$^+$ or [M−H]$^−$.
b) On a Chromolith Performance RP 18 column (100×4.6 mm id) eluting with 0.01M ammonium acetate in water (solvent A) and 100% acetonitrile (solvent B), using the following elution gradient 0-4 minutes 0→100% B, 4-5 minutes 100% B at a flow rate of 5 ml/minute. The mass spectra (MS) were recorded on a micromass Platform-LC mass spectrometer using atmospheric pressure chemical positive ionisation [AP+ve to give MH$^+$ molecular ions] or atmospheric pressure chemical negative ionisation [AP−ve to give (M−H)$^−$ molecular ions] modes. Analytical data from this apparatus are given with the following format: [M+H]+ or [M−H]− preceded by the acronym APCI to specify between both mass spectrometry analyses sources.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 ml/minute. The mass spectra (MS) were recorded on a micromass LCT mass spectrometer using electrospray positive ionisation [ES+ve to give MH$^+$ molecular ions] or electrospray negative ionisation [ES−ve to give (M−H)− molecular ions] modes.

Mass directed auto-prep HPLC refers to the method where the material was purified by high performance liquid chromatography on a HPLCABZ+5 μm column (5 cm×10 mm i.d.) with 0.1% HCO$_2$H in water and 95% MeCN, 5% water (0.5% HCO$_2$H) utilising the following gradient elution conditions: 0-1.0 minutes 5% B, 1.0-8.0 minutes 5-30% B, 8.0-8.9 minutes 30% B, 8.9-9.0 minutes 30→95% B, 9.0-9.9 minutes 95% B, 9.9-10 minutes 95→0% B at a flow rate of 8 ml/minute. The Gilson 202-fraction collector was triggered by a VG Platform Mass Spectrometer on detecting the mass of interest.

TLC (thin layer chromatography) refers to the use of TLC plates sold by Merck coated with silica gel 60 F254.

LC/MS Method
Analytical HPLC was conducted on a X-Terra MS 018 column (2.5 μm 30×3 mm id) eluting with 0.01M ammonium acetate in water (solvent A) and 100% acetonitrile (solvent B), using the following elution gradient 0-4 minutes 0 to 100% B, 4-5 minutes 100% B at a flow rate of 1.1 ml/minute. The mass spectra (MS) were recorded on a micromass Platform-LC mass spectrometer using atmospheric pressure chemical positive ionisation [AP+ve to give MH$^+$ molecular ions] or atmospheric pressure chemical negative ionisation [AP−ve to give (M−H)− molecular ions] modes.

LC/HRMS

Analytical HPLC was conducted on a Uptisphere-hsc column (3 µm 33×3 mm id) eluting with 0.01M ammonium acetate in water (solvent A) and 100% acetonitrile (solvent B), using the following elution gradient 0-0.5 minutes 5% B, 0.5-3.75 minutes 5 to 100% B, 3.75-4.5 100% B, 4.5-5 100 to 5% B, 5-5.5 5% B at a flow rate of 1.3 ml/minute. The mass spectra (MS) were recorded on a micromass LCT mass spectrometer using electrospray positive ionisation [ES+ve to give MH$^+$ molecular ions] or electrospray negative ionisation [ES−ve to give (M−H)− molecular ions] modes.

LCMS a) Method Formate
LC Conditions

The HPLC analysis was conducted on an Acquity HPLC BEH C18 column (50 mm×2.1 mm, i.d. 1.7 µm packing diameter) at 40° C.

The solvents employed were:
A=0.1% v/v solution of formic acid in water
B=0.1% v/v solution of formic acid in acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions

| MS | Waters ZQ |
|---|---|
| Ionisation mode | Alternate-scan positive and negative electrospray |
| Scan range | 100 to 1000 AMU |
| Scan time | 0.27 sec |
| Inter scan delay | 0.10 sec | b) Method HpH
LC Conditions

The HPLC analysis was conducted on an Acquity HPLC BEH C18 column (50 mm×2.1 mm, i.d. 1.7 µm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions

| MS | Waters ZQ |
|---|---|
| Ionisation mode | Alternate-scan positive and negative electrospray |
| Scan range | 100 to 1000 AMU |
| Scan time | 0.27 sec |
| Inter scan delay | 0.10 sec |

MDAP Methodology
Method Formate
LC Conditions

The HPLC analysis was conducted on either a Sunfire C18 column (100 mm×19 mm, i.d 5 µm packing diameter) or a Sunfire C18 column (150 mm×30 mm, i.d. 5 µm packing diameter) at ambient temperature.

The solvents employed were:
A=0.1% v/v solution of formic acid in water
B=0.1% v/v solution of formic acid in acetonitrile Run as a gradient over either 15 or 25 min (extended run) with a flow rate of 20 ml/min (100 mm×19 mm, i.d 5 µm packing diameter) or 40 ml/min (150 mm×30 mm, i.d. 5 µm packing diameter).

The UV detection was a summed signal from wavelength of 210 nm to 350 nm.
MS Conditions

| MS | Waters ZQ |
|---|---|
| Ionisation mode | Alternate-scan positive and negative electrospray |
| Scan range | 100 to 1000 AMU |
| Scan time | 0.50 sec |
| Inter scan delay | 0.20 sec |

In the procedures that follow, after each starting material, reference to an Intermediate by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Intermediate 1: 4-iodo-3,5-Dimethylisoxazole

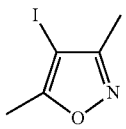

Nitric acid (13 ml) was added dropwise (exothermic reaction) to a mixture of 3,5-dimethylisoxazole (31.3 g, 320 mmol) and iodine (37.3 g, 150 mmol) and the mixture was stirred at room temperature for 1 h. The reaction mixture was hydrolysed with a mixture of ice and water and extracted with DCM. The organic phase was washed with a solution of $Na_2S_2O_3$, dried over $Na_2SO_4$ and concentrated under reduced pressure to afford the title compound as a yellow solid (60 g, 83%). [APCI MS] m/z: 224 MH$^+$, Rt 2.17 min.

Intermediate 2: 3-(3,5-Dimethyl-4-isoxazolyl)aniline

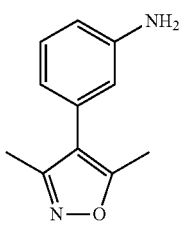

To a solution of 4-iodo-3,5-dimethylisoxazole (for a preparation see intermediate 1, 142 g, 640 mmol, 1 eq.) and (3-aminophenyl)boronic acid (100 g, 640 mmol, 1 eq.) in DME (600 ml) were added tetrakis(triphenylphosphine) palladium(0) (18.5 g, 16 mol) and a solution of $Na_2CO_3$ (203.5 g, 192 mmol, 3 eq.) in water (750 ml). The mixture was heated under reflux for 24 h. To complete the reaction intermediate 1 (0.2 eq.) and tetrakis(triphenylphosphine) palladium(0) (5 g) were added and the mixture was refluxed overnight. The cooled mixture was poured into water and extracted with DCM. The organic phase was washed with water, dried over $Na_2SO_4$ and filtered. Evaporation of the solvent in vacuo gave a crude oil which was precipitated with $iPr_2O$ to afford the title compound as a beige solid (102 g, 85%). [ES-MS] m/z: 189 MH$^+$, Rt 2.20 min.

Intermediate 3: 3,5-Dimethyl-4-[2-(methoxy)-5-nitrophenyl]isoxazole

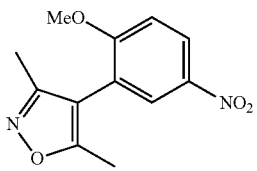 [SMILES: COc1ccc([N+](=O)[O-])cc1-c1c(C)noc1C]

To a solution of 2-iodo-1-(methoxy)-4-nitrobenzene (2 g, 7.17 mmol, 1 eq.) and (3,5-dimethylisoxazole)boronic acid (3.03 g, 21.5 mmol, 3 eq.) in DME (44 ml) and water (7 ml) were added tetrakis(triphenylphosphine) palladium(0) (0.415 g, 0.05 eq.) and $Ba(OH)_2 \cdot 8H_2O$ (4.52 g, 14.33 mmol, 2 eq.). The mixture was heated at 80° C. for 16 h. To complete the reaction (3,5-dimethylisoxazole)boronic acid (1 eq.) was added and the mixture was heated for 4 h. The cooled mixture was filtered and extracted with DCM. The organic phase was washed with saturated aqueous Sodium hydrogen carbonate and water, dried over $Na_2SO_4$ and filtered. Evaporation of the solvent in vacuo gave a crude oil which was precipitated with $iPr_2O$ to afford the title compound as a rust solid (1.735 g, 97%). GC/MS m/z: 248

Intermediate 4: 3-(3,5-Dimethyl-4-isoxazolyl)-4-(methoxy)aniline

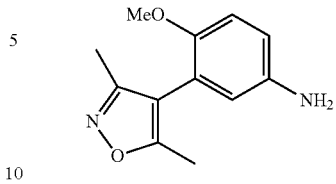

To a solution of 3,5-dimethyl-4-[2-(methoxy)-5-nitrophenyl]isoxazole (for a preparation see intermediate 3, 1.7 g, 6.85 mmol, 1 eq.) in ethanol (170 ml), was added Pd/C (10% on carbon, 85 mg) and the reaction was stirred under hydrogen for 4 h. AcOH (1.7 ml) was added and the reaction was hydrogenated for 20 h. After filtration, the solvent was evaporated in vacuo. The crude compound was dissolved into DCM and washed with saturated aqueous Sodium hydrogen carbonate, dried over $Na_2SO_4$, filtered and evaporated. The title compound was obtained as a red oil (1.38 g, 88%). GC/MS m/z: 218.

Intermediate 5: Diethyl ({[3-(3,5-dimethyl-4-isoxazolyl)phenyl]amino}methylidene)-propanedioate

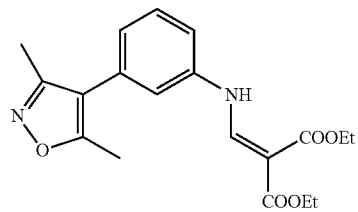 [SMILES: CCOC(=O)C(=CNc1cccc(-c2c(C)noc2C)c1)C(=O)OCC]

3-(3,5-Dimethyl-4-isoxazolyl)aniline (for a preparation see Intermediate 2, 80 g, 420 mmol) and diethyl ethoxymethylenemalonate (92 g, 425 mmol) were mixed together and heated to 130° C. for 20 minutes, liberating ethanol, which was evaporated under reduced pressure. The reaction mixture was poured into $iPr_2O$ (1 L) and the resulted precipitate filtered off and washed with $iPr_2O$. The resulting solid was recrystallised from acetonitrile to give the title compound as a brown solid (78 g, 52%).

$^1$H NMR (300 MHz, DMSO, ppm) δ: 10.8 (d, J=13.9 Hz, 1H), 8.50 (d, J=13.9 Hz, 1H), 7.62-7.41 (m, 3H), 7.26 (d, J=7.7 Hz, 1H), 4.3 (q, J=7.2 Hz, 2H), 4.21 (q, J=7.2 Hz, 2H), 2.51 (s, 3H), 2.34 (s, 3H), 1.35 (t, J=7.2 Hz, 3H), 1.33 (s, J=7.2 Hz, 3H).

The following intermediate was prepared in an analogous manner to intermediate 5:

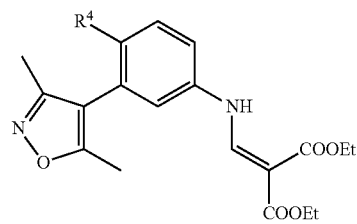

| Intermediate | R$^4$ | From | LC/MS |
|---|---|---|---|
| 6 | OCH$_3$ | Intermediate 4 | [APCI MS] m/z: 420 MH$^+$ |

Intermediate 7: Ethyl 7-(3,5-dimethyl-4-isoxazolyl)-4-hydroxy-3-quinolinecarboxylate

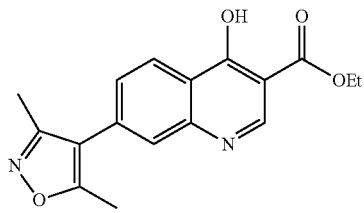 [SMILES: CCOC(=O)c1cnc2cc(-c3c(C)noc3C)ccc2c1O]

Diethyl ({[3-(3,5-dimethyl-4-isoxazolyl)phenyl]amino}methylidene)-propanedioate (for a preparation see Intermediate 5, 75 g, 210 mmol) was suspended in boiling diphenylether (1 L) and heated to reflux for 30 minutes. The reaction mixture was cooled and precipitated with iPr$_2$O to give the title compound as a brown powder (50 g, 76%). $^1$H NMR (300 MHz, DMSO-d6, ppm) δ: 12.45 (brs, 1H), 8.76 (s, 1H), 8.34 (d, J=8.6 Hz, 1H), 7.76 (s, 1H), 7.59 (d, J=8.6 Hz, 1H), 4.36 (q, J=7.1 Hz, 2H), 2.62 (s, 3H), 2.43 (s, 3H), 1.43 (s, J=7.1 Hz, 3H).

The following intermediate was prepared in an analogous manner to intermediate 7:

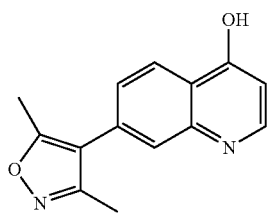

| Intermediate | R$^4$ | From | LC/HRMS (ES+) |
|---|---|---|---|
| 8 | OCH$_3$ | Intermediate 6 | Target Mass for C$_{18}$H$_{18}$N$_2$O$_5$: 343.1294 MH$^+$. Found: 343.1283; Rt: 2.02 min |

Intermediate 9: 7-(3,5-dimethyl-4-isoxazolyl)-4-hydroxy-3-quinolinecarboxylate

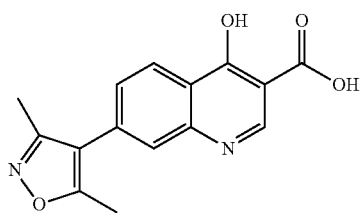 [SMILES: Cc1noc(C)c1-c1ccc2c(O)c(C(=O)O)cnc2c1]

A suspension of ethyl 7-(3,5-dimethyl-4-isoxazolyl)-4-hydroxy-3-quinolinecarboxylate (for a preparation see Intermediate 7, 5.5 g, 17.6 mmol) in a aqueous solution of sodium hydroxide 1N (80 ml) was heated to reflux for 5 h. The reaction mixture was treated with HCl 1N and the resulting white precipitate was filtered and taken up with MeOH, concentratred to dryness to give the title compound as a yellow powder (4.27 g, 85.3%).

$^1$H NMR (300 MHz, DMSO, ppm) δ: 8.81 (brs, 1H), 8.22 (d, J=8.5 Hz, 1H), 7.72 (brs, 1H), 7.52 (dd, J=8.5, 1.7 Hz, 1H), 2.36 (s, 3H), 2.16 (s, 3H).

The following intermediate was prepared in an analogous manner to intermediate 9:

| Intermediate | R$^4$ | From | LC/HRMS (ES+) |
|---|---|---|---|
| 10 | OCH$_3$ | Intermediate 8 | Target Mass for C$_{16}$H$_{14}$N$_2$O$_5$: 315.0981 MH$^+$. Found: 315.1002; Rt: 2.01 min |

Intermediate 11: 7-(3,5-dimethyl-4-isoxazolyl)-4-quinolinol 7-(3,5-dimethyl-4-isoxazolyl)-4-hydroxy-3-quinolinecarboxylate (for a preparation see Intermediate 9, 10 g, 35.21 mmol) was suspended by small portions to boiling diphenyl ether (200 ml) and allowed to reflux for 2 h. The reaction mixture was poured into hexane (500 ml) at 0° C., the precipitate was filtered and washed several times with hexane to give the title compound as a white solid (6.8 g, 86%). [APCI-MS] m/z: 240 MH$^+$, Rt 1.89 min. $^1$H NMR (300 MHz, CDCl$_3$, ppm) δ: 12.44 (brs, 1H), 8.67 (d, J=8.5 Hz, 1H), 8.10 (d, J=7.2 Hz, 1H), 7.80 (s, 1H), 7.62-7.55 (m, 1H), 7.25 (d, J=8.5 Hz, 1H), 6.61 (d, J=7.4 Hz, 1H), 2.64 (s, 3H), 2.49 (s, 3H).

Intermediate 12: 5-({[3-iodo-4-(methoxy)phenyl]amino}methylidene)-2,2-dimethyl-1,3-dioxane-4,6-dione

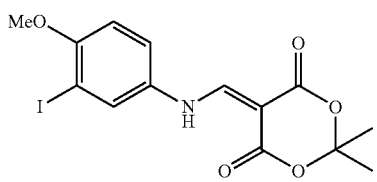 [SMILES: COc1ccc(NC=C2C(=O)OC(C)(C)OC2=O)cc1I]

A mixture of 2,2-dimethyl-1,3-dioxane-4,6-dione (203 g, 1.4 mol) and trimethoxymethane (1.5 l) was heated to reflux for 1 h, then the 3-iodo-4-methoxy-aniline (349.2 g, 1.402mol) was added portionwise. The reaction mixture was stirred at reflux for 1 h, then cooled to room temperature. The resulting precipitate was filtered off, washed with diisopropyl ether and dried to give the title compound as a beige powder (485 g, 85.9%)

$^1$H NMR (300 MHz, DMSO-d$_6$, ppm) δ: 11.2 (d, J=14.6 Hz, 1H), 8.50-8.39 (m, 1H), 8.05 (d, J=2.7 Hz, 1H), 7.60 (dd, J=8.9, 2.7 Hz, 1H), 7.05 (d, J=8.9 Hz, 1H), 3.84 (s, 3H), 1.67 (s, 6H).

Intermediate 13: 6-iodo-7-(methoxy)-1-quinolinol

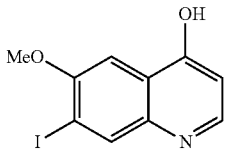 [SMILES: COc1cc2c(O)ccnc2cc1I]

5-({[3-iodo-4-(methoxy)phenyl]amino}methylidene)-2,2-dimethyl-1,3-dioxane-4,6-dione (for a preparation see Intermediate 12, 200 g, 0.496 mol) was added to diphenylether (2l) at 260° C. The reaction mixture was stirred at 260° C. for 10 minutes. The black solution was then cooled at 100° C. and poured into diisopropyl ether (8l) previously cooled at 0° C.

The precipitate was filtered off, poured into cyclohexane (1 l) and then heated to reflux for 1 h. The solid was filtered off, poured into methanol (250 ml) and heated at 45° C. for 15 minutes. The solid was then filtered off and dried over pallets pump to give the title compound (105 g, 70%).

$^1$H NMR (300 MHz, DMSO-d6, ppm) δ $^1$H NMR (300 MHz, D$_6$DMSO, ppm) δ: 8.07 (s, 1H), 7.88 (d, J=7.3 Hz, 1H), 7.45 (s, 1H), 6.06 (d, J=7.3 Hz, 1H), 3.90 (s, 3H).

Intermediate 14: 7-(3,5-dimethyl-4-isoxazolyl)-4-quinolinol

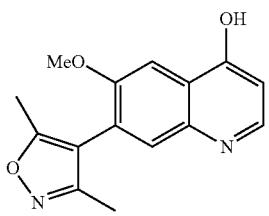 [SMILES: COc1cc2c(O)ccnc2cc1-c1c(C)noc1C]

3,5-dimethylisoxazole-4-boronic acid (49.2 g, 0.349 mol) and Ba(OH)$_2$.8H$_2$O (91.8 g, 0.291 mol, Acros) were added to a solution of intermediate 13 (35 g, 0.116 mol) in a mixture of water (180 ml)) and 1,2-dimethoxyethane (600 ml). The reaction was put under nitrogen for 15 minutes and tetrakis(triphenylphosphine)palladium (0) was added (4.1 g, 3.55 mmol, Aldrich). The reaction mixture was stirred at 105° C. overnight. After cooling at room temperature, the mixture was poured into water and extracted with ethyl acetate. The aqueous layer was acidified to pH 7 with concentrated HCl and extracted with ethyl acetate. The aqueous layer was basified to pH 10 with sodium hydroxide 5N and extracted with ethyl acetate. The organic layers were combined, washed with a saturated aqueous NaCl and dried. The crude brown oil was then purified by flash chromatography on silica gel eluting with DCM/MeOH (9:1) to give the title compound as a brown solid (31.4 g, 43.9%)

$^1$H NMR (300 MHz, DMSO-d6, ppm) δ: 11.72 (bs, 1H), 7.88 (d, J=7.7 Hz, 1H), 7.61 (s, 1H), 7.42 (s, 1H), 6.03 (d, J=7.3 Hz, 1H), 3.86 (s, 3H), 2.31 (s, 1H), 2.11 (s, 1H).

Intermediate 15: 7-(3,5-dimethyl-4-isoxazolyl)-3-nitro-4-quinolinol

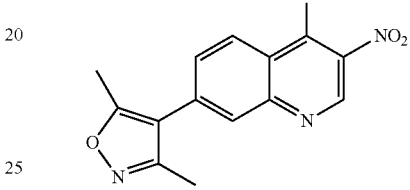

To a solution of 7-(3,5-dimethyl-4-isoxazolyl)-4-quinolinol (for a preparation see Intermediate 11, 8.5 g, 35 mmol) in propanoic acid (442 ml) was added nitric acid (7 ml) at room temperature, followed by heating the reaction mixture to 125° C. for 2 h. After cooling, the mixture was filtered, washed with isopropyl ether to give the title compound as a yellow solid (7.5 g, 75%). [APCI-MS] m/z: 283 [M−H]$^-$, Rt 2.41 min.

$^1$H NMR (300 MHz, DMSO-d$^6$, ppm) δ: 13.01 (brs, 1H), 9.28 (s, 1H), 8.33 (d, J=8.3 Hz 1H), 7.73 (s, 1H), 7.57 (d, J=8.3 Hz, 1H), 2.50 (s, 3H), 2.31 (s, 3H).

Intermediate 16: 4-chloro-7-(3,5-dimethyl-4-isoxazolyl)-3-nitroquinoline

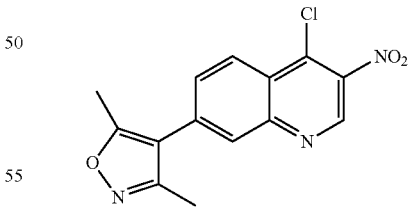

A suspension of 7-(3,5-dimethyl-4-isoxazolyl)-3-nitro-4-quinolinol (for a preparation see intermediate 15, 5 g, 17 mmol) in POCl$_3$ (50 ml) was refluxed overnight. After cooling the solvent was evaporated in vacuo. The resulting residue was poured over saturated aqueous Sodium hydrogen carbonate, extracted with DCM, washed with water, dried over Na$_2$SO$_4$. The solvent was evaporated under reduce pressure to give the title compound as a light brown solid (4 g, 75%).

$^1$H NMR (300 MHz, CDCl$_3$, ppm) δ: 9.23 (s, 1H), 8.45 (d,

J=8.9 Hz, 1H), 8.04 (d, J=1.5 Hz, 1H), 7.67 (dd, J=8.9, 1.5 Hz, 1H), 2.47 (s, 3H), 2.32 (s, 3H).

Intermediate 17: 7-(3,5-dimethyl-4-isoxazolyl)-6-(methoxy)-3-nitro-4-quinolinol

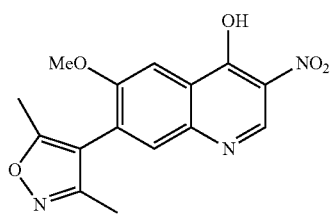 [SMILES: COc1cc2c(O)c([N+](=O)[O-])cnc2cc1-c1c(C)noc1C]

Nitric acid (10 ml) was added slowly to a solution of 7-(3,5-dimethyl-4-isoxazolyl)-4-quinolinol (for a preparation see Intermediate 14 (28 g, 104 mmol) in propanoic acid (450 ml) at room temperature, followed by heating the reaction mixture to 100° C. for 1 h. After cooling with an ice bath, the precipitate was filtered off, washed with pentane to give the title compound as a yellow powder (27 g, 82%). [APCI-MS] m/z: 314 [M−H]$^-$, Rt 2.12 min. $^1$H NMR (300 MHz, DMSO-d6, ppm) δ: 13.06 (s, 1H), 9.26 (s, 1H), 7.84 (s, 1H), 7.67 (s, 1H), 3.98 (s, 3H), 2.39 (s, 3H), 2.19 (s, 3H).

Intermediate 18: 4-chloro-7-(3,5-dimethyl-4-isoxazolyl)-6-(methoxy)-3-nitroquinoline

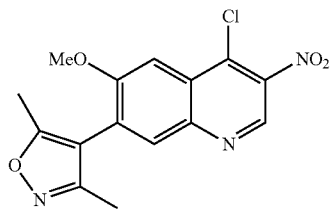

A suspension of 7-(3,5-dimethyl-4-isoxazolyl)-6-(methoxy)-3-nitro-4-quinolinol (for a preparation see Intermediate 17, 5 g, 16 mmol) in POCl$_3$ (20 ml) was refluxed overnight. After cooling, the mixture was evaporated to dryness. The resulting residue was poured over saturated aqueous Sodium hydrogen carbonate and extracted with DCM. The organic layer was washed with water, dried over Na$_2$SO$_4$. The solvent was evaporated under reduce pressure to give the title compound as a light brown powder (5 g, 94%). $^1$H NMR (300 MHz, DMSO-d6, ppm) δ: 9.27 (s, 1H), 8.15 (s, 1H), 7.73 (s, 1H), 4.05 (s, 3H), 2.36 (s, 3H), 2.16 (s, 3H).

Intermediate 19: N-[2-(tert-butyl)phenyl]-7-(3,5-dimethyl-4-isoxazolyl)-3-nitro-4-quinolinamine

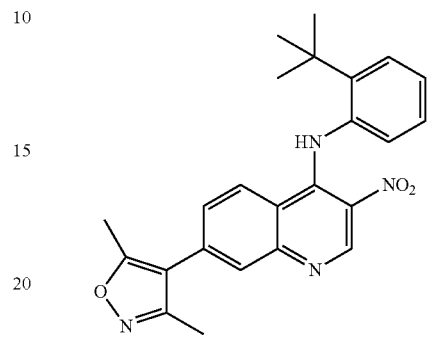

A mixture of 4-chloro-7-(3,5-dimethyl-4-isoxazolyl)-3-nitroquinoline (for a preparation see Intermediate 16) (2.2 g, 7.2 mmol) and 2-tert-butylaniline (1.2 g, 8 mmol) in CH$_3$CN (20 ml) was refluxed for 1 h. The solvent was evaporated in vacuo and the residue treated with an aqueous solution of sodium hydroxide N, extracted with DCM, washed with water and dried over Na$_2$SO$_4$. The residue was purified by chromatography on silica gel eluting with DCM/MeOH (99:1) to give the title compound as a yellow solid (2.4 g, 80%). [APCI-MS] m/z: 417 MH$^+$, Rt 3.73 min. NMR (300 MHz, DMSO-d6, ppm) δ: 9.87 (brs, 1H), 8.92 (s, 1H), 8.34 (d, J=8.7 Hz, 1H), 7.82 (s, 1H), 7.50 (d, J=8.9 Hz, 1H), 7.25-6.91 (m, 4H), 2.32 (s, 3H), 2.15 (s, 3H).

The following intermediates were prepared in an analogous manner to intermediate 19:

| Intermediate | R$^1$ | LC/MS or NMR |
| --- | --- | --- |
| 20 | ![Cl-phenyl] | APCI-MS: m/z 409 MH$^+$, Rt = 3.34 min |
| 21 | ![phenyl] | APCI-MS: m/z 375 MH$^+$, Rt 3.26 min |

-continued

| Intermediate | R¹ | LC/MS or NMR |
|---|---|---|
| 22 | cyclohexylmethyl | APCI-MS: m/z 381 MH⁺, Rt 3.65 min |
| 23 | neopentyl (tert-butylmethyl) | APCI-MS: m/z 355 MH⁺, Rt 3.40 min |
| 24 | 2-(trifluoromethoxy)benzyl | NMR (300 MHz, DMSO-d6, ppm) δ: 9.32 (brs, 1H), 8.48 (d, J = 8.7 Hz, 1H), 8.15 (brs, 1H), 7.80 (d, J = 8.5 Hz, 1H), 7.60 (d, J = 8.1 Hz, 1H), 7.55-7.37 (m, 2H), 2.66 (s, 3H), 2.49 (s, 3H). |
| 25 | 1-phenylethyl (rac) | APCI-MS: m/z 389 MH⁺, Rt = 3.35 min |
| 26 | 4-fluorobenzyl | APCI-MS: m/z 393 MH⁺, Rt = 3.26 min |
| 27 | 2-pyridylmethyl | APCI-MS: m/z 376 MH⁺, Rt = 2.94 min |

Intermediate 28: 7-(3,5-dimethyl-4-isoxazolyl)-N⁴-(phenylmethyl)-3,4-quinolinediamine

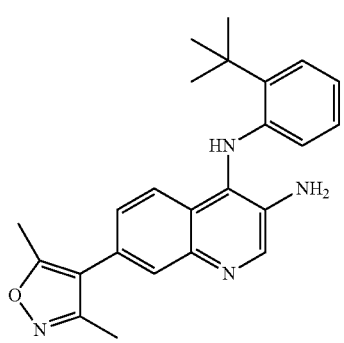 [SMILES: Cc1noc(C)c1-c1ccc2c(Nc3ccccc3C(C)(C)C)c([N+](=O)[O-])cnc2c1]

To a solution of N-[2-(tert-butyl)phenyl]-7-(3,5-dimethyl-4-isoxazolyl)-3-nitro-4-quinolinamine (see Intermediate 19, 2.4 g, 5.77 mmol) in a mixture of ethanol (60 ml) and THF (20 ml), was added SnCl₂,2H₂O (7.81 g, 34.6 mmol). The reaction mixture was refluxed for 3 h and then concentrated to dryness. The resulting residue was poured into aqueous sodium hydroxide. The organic phase was extracted with EtOAc, washed with water, dried and concentrated to give the title compound as a yellow solid (2 g, 71%). [APCI-MS] m/z: 387 MH⁺, Rt 3.37 min.

The following intermediates were prepared in an analogous manner to intermediate 28 from the corresponding nitro derivatives:

| Intermediate | R¹ | LC-MS or ¹H NMR |
|---|---|---|
| 29 | 2-chlorobenzyl | APCI-MS: m/z 379 MH⁺, Rt 2.97 min |
| 30 | benzyl | APCI-MS: m/z 345 MH⁺, Rt 2.79 min |
| 31 | cyclohexylmethyl | APCI-MS: m/z 351 MH⁺, Rt 3.16 min |
| 32 | neopentyl | APCI-MS: m/z 325 MH⁺, Rt 2.98 min |
| 33 | 2-(trifluoromethoxy)benzyl | APCI-MS: m/z 415 MH⁺, Rt 3.20 min |
| 34 | 1-phenylethyl (rac) | DMSO-d6, δ: 8.24 (s, 1H), 7.98 (d, J = 8.7 Hz, 1H), 7.52 (d, J = 1.7 Hz, 1H), 7.32-7.25 (m, 2H), 7.18 (d, J = 8.9, 1.9 Hz, 1H), 7.14-6.96 (m, 3H), 4.63-4.50 (m, 1H), 2.28 (s, 3H), 2.11 (s, 3H), 1.36 (d, J = 6.6 Hz, 3H). |
| 35 | 4-fluorobenzyl | APCI-MS: m/z 363 MH⁺, Rt 2.86 min |
| 36 | 2-pyridylmethyl | APCI-MS: m/z 346 MH⁺, Rt 2.44 min |

Intermediate 37: 7-(3,5-dimethyl-4-isoxazolyl)-6-(methoxy)-N$^4$-[(1R)-1-(2-pyridinyl)ethyl]-3,4-quinolinediamine

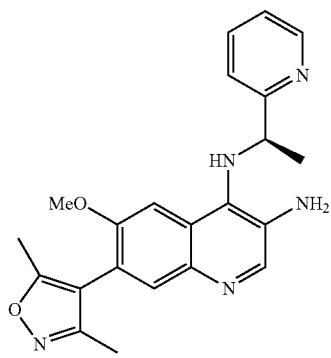 [SMILES: COc1cc2c(N[C@H](C)c3ccccn3)c(N)cnc2cc1-c1c(C)noc1C]

A mixture of 4-chloro-7-(3,5-dimethyl-4-isoxazolyl)-6-(methoxy)-3-nitroquinoline (for a preparation see Intermediate 18, 0.4 g, 1.2 mmol) and (1R)-1-(2-pyridinyl)ethanamine (2 eq, 0.293 g) in CH$_3$CN (20 ml) was heated at 60° C. for 2 h. The mixture was extracted with DCM. The organic phase washed with saturated aqueous Sodium hydrogen carbonate and dried over Na$_2$SO$_4$. The solvent was evaporated under reduced pressure and the residue taken up in diethyl ether. The precipitate was filtered off and dried in vacuo to give 7-(3,5-dimethyl-4-isoxazolyl)-6-(methoxy)-3-nitro-N-[(1R)-1-(2-pyridinyl)ethyl]-4-quinolinamine (0.4 g) which was used without purification in the next step.

To a solution of this intermediate (0.4 g, 0.95 mmol) in a mixture of ethanol (20 ml) and HCl (3.8 ml), was added SnCl$_2$.2H$_2$O (0.89 g, 3.96 mmol). The reaction mixture was heated to 40° C. for 1 h, then hydrolysed with sodium hydroxide N and extracted with DCM. The organic phase was washed with water, dried and concentrated. The residue was purified by flash chromatography on silica gel (DCM/MeOH, 95:5), the resulting compound was triturated in diisopropyl ether to give the title compound as a brown powder (0.25 g, 53.5%). [APCI-MS] m/z: 390 MH$^+$, Rt 2.62 min. $^1$H NMR (300 MHz, DMSO-d6, ppm) δ: 8.54 (d, J=4.7 Hz, 1H), 8.30 (s, 1H), 7.73 (dd, J=7.8, 7.6 Hz, 1H), 7.52 (s, 1H), 7.52-7.48 (m, 1H), 7.33 (s, 1H), 7.27-7.21 (m, 1H), 5.29-5.10 (m, 3H), 3.81 (s, 3H), 2.28 (s, 3H), 2.08 (s, 3H), 1.56 (d, J=6 Hz, 3H)

Intermediate 38: 7-(3,5-dimethyl-4-isoxazolyl)-6-(methoxy)-N$^4$-(2-pyridinylmethyl)-3,4-quinolinediamine

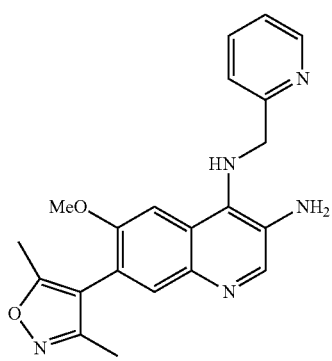 [SMILES: COc1cc2c(NCc3ccccn3)c(N)cnc2cc1-c1c(C)noc1C]

A mixture of 4-chloro-7-(3,5-dimethyl-4-isoxazolyl)-6-(methoxy)-3-nitroquinoline (for a preparation see Intermediate 18, 2.5 g, 7.5 mmol) and 2-aminomethylpyridine (2 eq, 1.41 g) in CH$_3$CN (30 ml) was heated at 60° C. for 2 h. The mixture was extracted with DCM. The organic phase washed with saturated aqueous sodium hydrogen carbonate and dried over Na$_2$SO$_4$. The solvent was evaporated under reduced pressure and the residue taken up in diethyl ether. The precipitate was filtered off and dried in vacuo to give 7-(3,5-dimethyl-4-isoxazolyl)-6-(methoxy)-3-nitro-N-(2-pyridinylmethyl)-4-quinolinamine (2.5 g) which was used without purification in the next step.

To a solution of this nitro intermediate (2.5 g, 24.82 mmol) in a mixture of ethanol (20 ml) and HCl (3.8 ml), was added portionwise SnCl$_2$.2H$_2$O (5.6 g, 24.82 mmol). The reaction mixture was heated to 40° C. for 1 h, then hydrolysed with sodium hydroxide N and extracted with DCM. The organic phase was washed with water, dried and concentrated to give the title compound as a brown powder (0.5 g, 17.8%). (APCI-MS) m/z: 376 MH$^+$, Rt 2.46 min. $^1$H NMR (300 MHz, DMSO-d6, ppm) δ: 8.56 (d, 1H), 8.29 (s, 1H), 7.77 (dd, J=7.8, 7.6 Hz, 1H), 7.54 (s, 1H), 7.53-7.51 (m, 1H), 7.31-7.25 (m, 1H), 5.31 (s, 2H), 4.46 (d, J=7.2 Hz, 2H), 3.78 (s, 3H), 2.28 (s, 3H), 2.09 (s, 3H).

Intermediate 39: 7-(3,5-dimethyl-4-isoxazolyl)-6-(methoxy)-N⁴-[(1R)-1-phenylethyl]-3,4-quinolinediamine

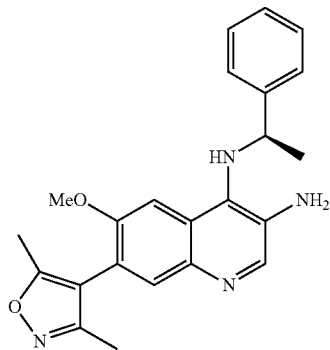 [SMILES: COc1cc2c(N[C@H](C)c3ccccc3)c(N)cnc2cc1-c1c(C)noc1C]

A mixture of 4-chloro-7-(3,5-dimethyl-4-isoxazolyl)-6-(methoxy)-3-nitroquinoline (for a preparation see Intermediate 18, 2.5 g, 7.5 mmol) and (R)-(+)-alpha-methylbenzylamine (2 eq, 1.82 g, Aldrich) in CH₃CN (30 ml) was heated at 60° C. for 2 h. The mixture was extracted with DCM. The organic phase washed with saturated aqueous sodium hydrogen carbonate and dried over Na₂SO₄. The solvent was evaporated under reduced pressure and the residue taken up in diethyl ether. The precipitate was filtered off and dried under vacuum to give 7-(3,5-dimethyl-4-isoxazolyl)-6-(methoxy)-3-nitro-N-[(1R)-1-phenylethyl]-4-quinolinamine (2.5 g) which was used without purification in the next step.

To a solution of this nitro intermediate (2.5 g, 24.82 mmol) in a mixture of ethanol (20 ml) and HCl (3.8 ml), was added portionwise SnCl₂.2H₂O (5.6 g, 24.82 mmol). The reaction mixture was heated to 40° C. for 1 h, then hydrolysed with sodium hydroxide N and extracted with DCM. The organic phase was washed with water, dried and concentrated to give the title compound as a brown powder (0.5 g, 17%). (APCI-MS) m/z: 389 MH⁺, Rt 2.95 min.

Intermediate 40: 4-chloro-7-(3,5-dimethyl-4-isoxazolyl)-6-(methoxy)-3-quinolinecarboxamide

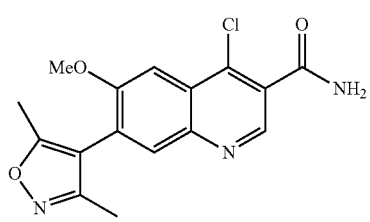 [SMILES: COc1cc2c(Cl)c(C(N)=O)cnc2cc1-c1c(C)noc1C]

A mixture of intermediate 10 (27.7 g, 0.079 mol) and 10 drops of anhydrous DMF in POCl₃ (250 ml) was refluxed for 5 h. Then, the mixture was concentrated to dryness under vacuum. The residue was treated twice with 100 ml of toluene and evaporated to dryness to remove the last traces of POCl₃. The dry foam obtained is added portionwise to an aqueous solution of ammonia (25%, 300 ml) cooled to 0/5° C. with an ice bath. After the end of the addition, the vigourous stirring was maintained for 1 h at this temperature. Then, the brown solid material was filtered off and washed respectively with water (3×200 ml), diisopropyl ether (2×200 ml) and pentane (100 ml) to give after drying the crude product. This material was purified by a flash chromatography on silica gel (eluant =CH₂Cl₂/MeOH, 95/5) to give the title compound (16.8 g, 64.7%).

¹H NMR (300 MHz, CDCl3, ppm) δ: 8.96 (s, 1H), 7.86 (s, 1H), 7.54 (s, 1H), 3.95 (s, 3H), 2.30 (s, 3H), 2.15 (s, 3H).

Intermediate 41: Ethyl 7-(3,5-dimethyl-4-isoxazolyl)-4-chloro-3-quinolinecarboxylate

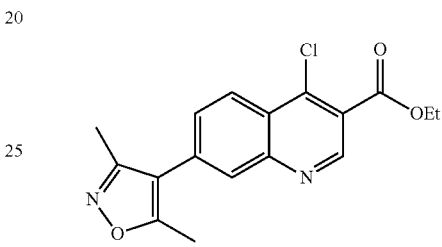

Ethyl 7-(3,5-dimethyl-4-isoxazolyl)-4-hydroxy-3-quinolinecarboxylate (for a preparation see Intermediate 7, 20 g, 64.04 mmol) was reacted with thionyl chloride (326 ml) and heated to reflux overnight. Excess thionyl chloride was co-evaporated with toluene. The crude product was triturated with iPr₂O and filtered to give the title compound as a brown powder (20.15 g, 95%).

¹H NMR (300 MHz, DMSO, ppm) δ: 9 (s, 1H), 8.2 (d, 1H), 8.0 (s, 1H), 7.8 (d, 1H), 4.25 (q, 2H), 2.2 (s, 3H), 2.1 (s, 3H), 1.2 (t, 3H).

Intermediate 42: Ethyl 4-chloro-7-(3,5-dimethyl-4-isoxazolyl)-6-(methoxy)-3-quinolinecarboxylate

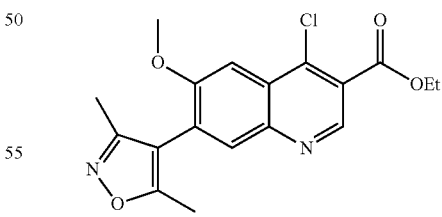

Intermediate 8 (5 g, 14.62 mmol) was reacted with phosphorus oxychloride (50 ml) and heated to reflux overnight. Excess phosphorus oxychloride was evaporated with toluene. The crude product was washed with 1N sodium hydroxide solution and extracted with DCM. The organic phase was dried over Na₂SO₄ and evaporated under reduced pressure to give the title compound as a brown solid (5.1 g, 96.9%).

APCI-MS: m/z 361 MH⁺, Rt=3.31 min

Intermediate 43: Ethyl 4-{[2-(1,1-di methylethyl) phenyl]amino}-7-(3,5-dimethyl-4-isoxazolyl)-6-(methoxy)-3-quinolinecarboxylate

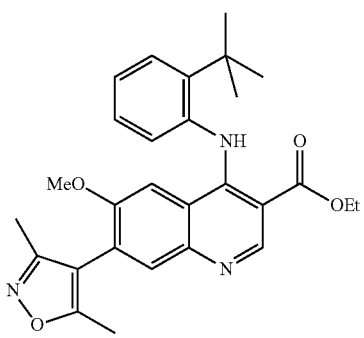 [SMILES: CCOC(=O)c1cnc2cc(-c3c(C)noc3C)c(OC)cc2c1Nc1ccccc1C(C)(C)C]

A mixture of ethyl 4-chloro-7-(3,5-dimethyl-4-isoxazolyl)-6-(methoxy)-3-quinolinecarboxylate (for a preparation see Intermediate 42 (3.3 g, 9.2 mmol) and 2-tert-butylaniline (2.7 ml, 18.4 mmol) in dioxane (50 ml) was refluxed for 2 days. After cooling, the reaction mixture was evaporated under reduced pressure and the precipitate was purified by chromatography on silica gel eluting with DCM/MeOH (95/5) to give the title compound as a solid (1.2 g, 27.7%).

HRMS Target Mass: 474.2393 MH$^+$. Found: 474.2379; Rt 3.82 min

The following intermediates were prepared in an analogous manner to intermediate 43 from intermediate 42:

| Intermediate | R$^1$ | LC-MS or $^1$H NMR |
|---|---|---|
| 44 | OCF$_3$ | APCI-MS: m/z 502 MH$^+$, Rt 3.78 min |
| 45 | F | APCI-MS: m/z 436 MH$^+$, Rt 3.53 min |
| 46 |  | APCI-MS: m/z 431 MH$^+$, Rt 3.52 min |
| 47 | F, F | APCI-MS: m/z 468 MH$^+$, Rt 3.61 min |
| 48 | Cl, F | APCI-MS: m/z 484 MH$^+$, Rt 3.77 min |

Intermediate 49: 4-{[2-(1,1-dimethylethyl)phenyl]amino}-7-(3,5-dimethyl-4-isoxazolyl)-6-(methoxy)-3-quinolinecarboxylic acid hydrochloride

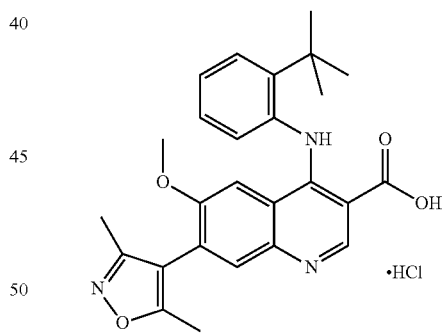

A mixture of ethyl 4-{[2-(1,1-dimethylethyl)phenyl]amino}-7-(3,5-dimethyl-4-isoxazolyl)-6-(methoxy)-3-quinolinecarboxylate (for a preparation see Intermediate 43, 1.2 g, 2.54 mmol) and 1N sodium hydroxide (3 ml) in Ethanol was heated to reflux for 1 day. The reaction mixture was concentrated, taken up in water and neutralised with 1N HCl. The precipitate was filtered, and dried to give the title compound as a yellow powder (0.96 g, 85%). LC/HRMS Target Mass calculated for $C_{26}H_{27}N_3O_4$: 446.2080 MH$^+$. Found: 446.2038; Rt 2.39 min The following intermediates were prepared in an analogous manner to intermediate 49 from the corresponding ester derivatives:

| Intermediate | R¹ | LC-MS, LC/HRMS or ¹H NMR |
|---|---|---|
| 50 | ![F₃CO-phenyl] | Target Mass for C₂₃H₁₈F₃N₃O₅: 474.1277 MH⁺. Found: 474.1241, Rt 2.20 min |
| 51 | ![2-F-phenyl] | APCI-MS m/z: 408 MH⁺, Rt 2.42 min |
| 52 | ![benzyl] | Target Mass for C₂₃H₂₂N₃O₄: 404.1610 MH⁺. Found: 404.1578, Rt 2.16 min |
| 53 | ![2,4-diF-benzyl] | APCI-MS m/z: 440 MH⁺, Rt 2.60 min |
| 54 | ![2-Cl-4-F-benzyl] | APCI-MS m/z: 456 MH⁺, Rt 2.70 min |

Intermediate 55: 7-(3,5-dimethyl-4-isoxazolyl)-6-(methyloxy)-4-{[(1R)-1-(2-pyridinyl)ethyl]amino}-3-quinolinecarboxamide

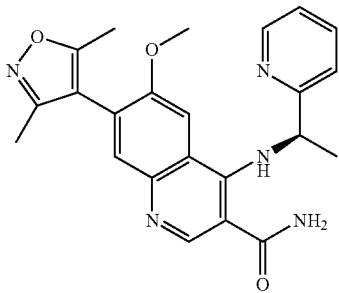 [SMILES: COc1cc2c(N[C@H](C)c3ccccn3)c(C(N)=O)cnc2cc1-c1c(C)noc1C]

4-Chloro-7-(3,5-dimethyl-4-isoxazolyl)-6-(methyloxy)-3-quinolinecarboxamide (for a preparation see Intermediate 56, 50 g, 151 mmol,) and [(1R)-1-(2-pyridinyl)ethyl]amine (35.3 g, 181 mmol, NetChem) were dissolved in N-methyl-2-pyrrolidone (NMP, 250 ml). DIPEA (79 ml, 452 mmol) was added, the solution was heated at 120° C. overnight, cooled and diluted with ethyl acetate (1 l). The solution was washed with water (2×1 l), brine (500 ml), dried (sodium sulphate) and the solvent evaporated to give a dark brown gum. The aqueous washings were extracted with DCM (2×600 ml). The combined extracts were washed with a mixture of saturated brine (300 ml) and water (1 l) giving a dense emulsion which took around 2 h to separate. The organic layer was dried (sodium sulphate) and evaporated to leave a brown liquid. This liquid was dissolved in ethyl acetate (200 ml), washed with water (2×200 ml), dried (sodium sulphate) and evaporated to give a brown gum. This material was combined with the previous brown gum, dissolved in DCM (150 ml) and loaded onto a silica column (750 g), which was eluted with a 2M ammonia in methanol/DCM gradient (0-12%) to give, after evaporation of the solvents in vacuo 7-(3,5-dimethyl-4-isoxazolyl)-6-(methyloxy)-4-{[(1R)-1-(2-pyridinyl)ethyl]amino}-3-quinolinecarboxamide as beige foam (45.1 g). Used in the subsequent step (Example 36) without further purification.

1H NMR CDCl₃: δH 9.44 (1H, d), 8.71 (1H, s), 8.62 (1H, d), 7.74 (1H, m), 7.68 (1H, s), 7.65 (1H, d), 7.34 (1H, s), 7.23 (1H, m), 6.06 (2H, b), 5.36 (1H, m), 3.51 (3H, s), 2.32 (3H, s), 2.17 (3H, s), 1.73 (3H, d, partially obscured by water).

The mixed fractions from the column were collected and evaporated to give a brown gum. This was dissolved in DCM (20 ml) loaded onto a silica column (330 g) and eluted with an 2M ammonia in methanol/DCM gradient (0-10%) to give after evaporation of solvents 7-(3,5-dimethyl-4-isoxazolyl)-6-(methyloxy)-4-{[(1R)-1-(2-pyridinyl)ethyl]amino}-3-quinolinecarboxamide as beige gum (3.4 g).

1H NMR CDCl₃: δH 9.44 (1H, d), 8.71 (1H, s), 8.62 (1H, d), 7.74 (1H, m), 7.68 (1H, s), 7.65 (1H, d), 7.34 (1H, s), 7.23 (1H, m), 6.07 (2H, b), 5.36 (1H, m), 3.51 (3H, s), 2.32 (3H, s), 2.17 (3H, s), 1.73 (3H, d, partially obscured by water).

LCMS (Method HpH): MH⁺418, Rt 0.87 min.

Intermediate 56: 4-Chloro-7-(3,5-dimethyl-4-isoxazolyl)-6-(methyloxy)-3-quinolinecarboxamide

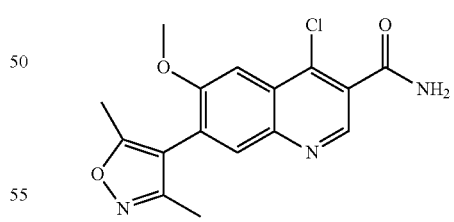

7-(3,5-Dimethyl-4-isoxazolyl)-6-(methyloxy)-4-oxo-1,4-dihydro-3-quinolinecarboxylic acid (for a preparation see intermediate 57, 54 g, 172 mmol) was heated in phosphorous oxychloride (80 ml, 859 mmol) for 4 h, then allowed to cool to room temperature and to stand overnight. The mixture was reduced to dryness in vacuo and the brown residue azeotroped with toluene (2×300 ml). The resulting dark brown gum was dissolved in THF (300 ml) with heating and sonication and the resulting solution added dropwise to ammonium hydroxide (33% w/w, 500 ml) with ice bath cooling. The mixture was stirred for 30 min, then concentrated to half volume, diluted with water (100 ml) and the resulting dark brown solid collected by filtration. The solid was washed with water (100 ml) and dried under vacuum at 50° C. for 3 days to give 4-chloro-7-(3,5-dimethyl-4-isoxazolyl)-6-(methyloxy)-3-quinolinecarboxamide as brown solid (50.8 g).

1H NMR D$_6$-DMSO: δH 8.75 (1H, s), 8.19 (1H, bs), 8.01 (1H, s), 7.98 (1H, bs), 7.62 (1H, s), 4.00 (3H, s), 2.34 (3H, s), 2.14 (3H, s).

LCMS (Method Formate): MH$^+$332/334, Rt 0.76 min.

Intermediate 57: 7-(3,5-Dimethyl-4-isoxazolyl)-6-(methyloxy)-4-oxo-1,4-dihydro-3-quinolinecarboxylic acid

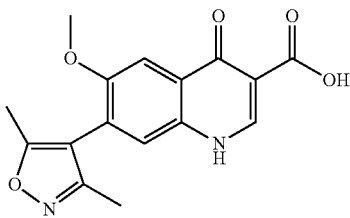 [SMILES: COc1cc2c(=O)c(C(=O)O)c[nH]c2cc1-c1c(C)noc1C]

Ethyl 7-(3,5-dimethyl-4-isoxazolyl)-4-hydroxy-6-(methyloxy)-3-quinolinecarboxylate (for a preparation see Intermediate 58, 70.2 g, 205 mmol,) was suspended in a mixture of ethanol (200 ml) and sodium hydroxide (2M, 308 ml, 615 mmol) and the mixture was heated at reflux overnight. The reaction was concentrated to ca 200 ml in vacuo, diluted with water (500 ml) and the resulting solution washed with ethyl acetate (200 ml). The aqueous phase was acidified to pH4 with hydrochloric acid (1M), the resulting suspension stirred vigorously for 10 min. The solid was collected by filtration, washed with water (200 ml) and dried overnight at 40° C. in vacuo to give 7-(3,5-dimethyl-4-isoxazolyl)-4-hydroxy-6-(methyloxy)-3-quinolinecarboxylic acid as a beige solid (54.7 g). Used without further purification.

1H NMR D$_6$-DMSO: δH 15.51 (1H, s), 13.36 (1H, b), 8.88 (1H, s), 7.77 (1H, s), 7.71 (1H, s), 3.94 (3H, s), 2.33 (3H, s), 2.13 (3H, s).

LCMS (Method Formate): MH$^+$315, Rt 0.80 min.

Intermediate 58: Ethyl 7-(3,5-dimethyl-4-isoxazolyl)-4-hydroxy-6-(methyloxy)-3-quinolinecarboxylate

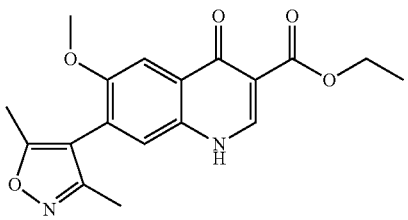 [SMILES: CCOC(=O)c1c[nH]c2cc(-c3c(C)noc3C)c(OC)cc2c1=O]

Diethyl({[3-(3,5-dimethyl-4-isoxazolyl)-4-(methyloxy)phenyl]amino}methylidene) propanedioate (for a preparation see Intermediate 59, 50 g, 129 mmol) was added in small portions over 15 min to boiling diphenyl ether (300 ml) (temperature ca 255° C.). The mixture was heated for a further 30 min and the mixture was allowed to cool to 50° C. The reaction was diluted with cyclohexane (300 ml) and cooled further, giving a thick tarry residue. The supernatant solvent was decanted and the residue was heated at reflux in ethyl acetate (300 ml) for 20 min, then diluted with cyclohexane (200 ml) and cooled to room temperature. The solid residue was collected by filtration, washed with diethyl ether (200 ml) and dried in vacuo at 40° C. to give ethyl 7-(3,5-dimethyl-4-isoxazolyl)-4-hydroxy-6-(methyloxy)-3-quinolinecarboxylate as brown powder (28.1 g). Used without further purification in the subsequent reaction (Intermediate 57).

1H NMR D$_6$-DMSO: δH 12.28 (1H, s), 8.55 (1H, s), 7.69 (1H, s), 7.51 (1H, s), 4.22 (2H, q), 3.88 (3H, s), 2.31 (3H, s), 2.11 (3H, s), 1.29 (3H, t).

Intermediate 59: Diethyl ({[3-(3,5-dimethyl-4-isoxazolyl)-4-(methyloxy)phenyl]amino}methylidene) propanedioate

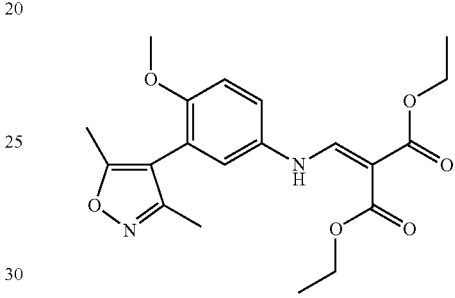

[3-(3,5-Dimethyl-4-isoxazolyl)-4-(methyloxy)phenyl] amine (for a preparation see Intermediate 60, 27.4 g, 126 mmol) was dissolved in diethyl [(ethyloxy)methylidene]propanedioate (27.1 g, 126 mmol) and heated to 130° C. The solution was heated for 1 h, then cooled to room temperature and reduced to dryness in vacuo to give diethyl ({[3-(3,5-dimethyl-4-isoxazolyl)-4-(methyloxy)phenyl] amino}methylidene)propanedioate (50.1 g), which after standing overnight became as a brown crystalline solid.

1H NMR CDCl$_3$: δH 11.02 (1H, d), 8.44 (1H, d), 7.16 (1H, dd), 6.98 (1H, d), 6.91 (1H, d), 4.34-4.22 (4H, m), 3.81 (3H, s), 2.32 (3H, s), 2.17 (3H, s), 1.40-1.31 (6H, m).

LCMS (Method Formate): MH$^+$389, Rt 1.17 min.

Intermediate 60: [3-(3,5-Dimethyl-4-isoxazolyl)-4-(methyloxy)phenyl]amine

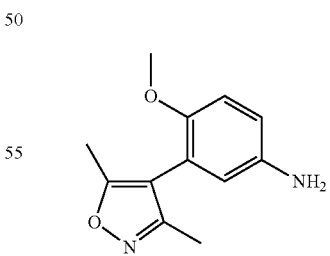

3,5-Dimethyl-4-[2-(methyloxy)-5-nitrophenyl]isoxazole (for a preparation see Intermediate 61, 68 g, 274 mmol) was dissolved in ethyl acetate (1 l) and the solution washed with sodium sulphite solution (5%, 500 ml). The organic layer was dried (sodium sulphate) and filtered through a 3 cm pad of silica gel. The filtrate was diluted with ethanol (1 l) and added to Pd/C (E101 type NO/W, 10 g) in a 5 l nitrogen/vacuum purged hydrogenation flask under vacuum, The mixture was stirred for 24 h. The mixture was purged with vacuum/nitrogen cycles (×3), filtered through Celite under nitrogen and the filtrate evaporated in vacuo to give [3-(3,5-dimethyl-4-isoxazolyl)-4-(methyloxy)phenyl]amine 3-(3,5-dimethyl-4-isoxazolyl)-4-(methyloxy)aniline (62.3 g).

1H NMR CDCl3: δH 6.82 (1H, d), 6.71 (1H, dd), 6.50 (1H, d), 3.71 (3H, s), 3.46 (2H, b), 2.31 (3H, s), 2.18 (3H, s).

LCMS (Method Formate): MH+219, Rt 0.48 min.

Intermediate 61: 3,5-Dimethyl-4-[2-(methyloxy)-5-nitrophenyl]isoxazole

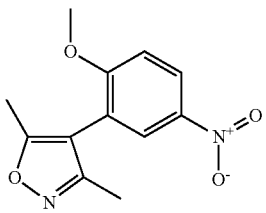 [SMILES: COc1ccc([N+](=O)[O-])cc1-c1c(C)noc1C]

3-Iodo-4-(methoxy) nitrobenzene (65 g, 233 mmol, Matrix Scientific), (3,5-dimethyl-4-isoxazolyl)boronic acid (36.1 g, 256 mmol) and cesium carbonate (152 g, 466 mmol) were combined with DME (80 ml) and water (40 ml) and the mixture was degassed with nitrogen for 10 min, then PEPPSI™ catalyst (3.96 g, 5.82 mmol) was added and the mixture heated at 90° C. for 4 h, then cooled and diluted with ethyl acetate (800 ml). The resulting suspension was filtered through Celite and the filtrate washed with water (2×500 ml). The solvent was dried (sodium sulphate), filtered and evaporated to give a brown solid which was triturated with ether (30 ml). The solid product was washed with ether (100 ml) to give 3,5-dimethyl-4-[2-(methyloxy)-5-nitrophenyl]isoxazole as beige solid (48.2 g).

1H NMR CDCl3: δH 8.30 (1H, dd), 8.06 (1H, d), 7.07 (1H, d), 3.94 (3H, s), 2.33 (3H, s), 2.17 (3H, s). LCMS (Method Formate): MH+249, Rt 1.01 min.

Intermediate 62: 7-(3,5-Dimethyl-4-isoxazolyl)-6-(methyloxy)-4-{[1-(1-methyl-1H-pyrazol-4-yl)ethyl]amino}-3-quinolinecarboxamide

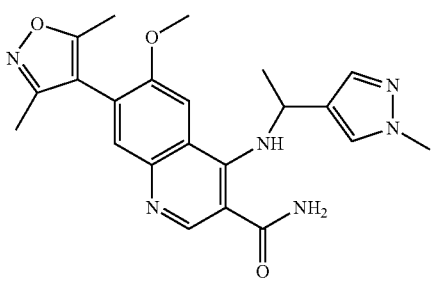 [SMILES: COc1cc2c(NC(C)c3cnn(C)c3)c(C(N)=O)cnc2cc1-c1c(C)noc1C]

4-Chloro-7-(3,5-dimethyl-4-isoxazolyl)-6-(methyloxy)-3-quinolinecarboxamide (for a preparation see Intermediate 56, 200 mg, 0.603 mmol) and [1-(1-methyl-1H-pyrazol-4-yl)ethyl]amine (113 mg) and DIPEA (0.326 ml, 1.869 mmol) and N-Methyl-2-pyrrolidone (NMP) (15 ml) at 120° C. for 4 h. The reaction mixture was cooled to room temperature, diluted with water (300 ml) and extracted with ethyl acetate (2×200 ml). The combined organics were washed with water (300 ml) and brine (200 ml), dried (sodium sulphate) and evaporated. The resulting gum was dissolved in DCM (3 ml) loaded onto a loaded onto a silica cartridge (100 g), which was then eluted with a 2M methanolic ammonia/DCM gradient (0-12%) to give, after evaporation of the product containing fractions in vacuo 7-(3,5-dimethyl-4-isoxazolyl)-6-(methyloxy)-4-{[1-(1-methyl-1H-pyrazol-4-yl)ethyl]amino}-3-quinolinecarboxamide (110 mg).

LCMS (Method Formate): MH+ 421, Rt 0.62 min

Intermediate 63: 7-(3,5-dimethylisoxazol-4-yl)-6-methoxy-N4-(pyridin-2-ylmethyl)quinoline-3,4-diamine

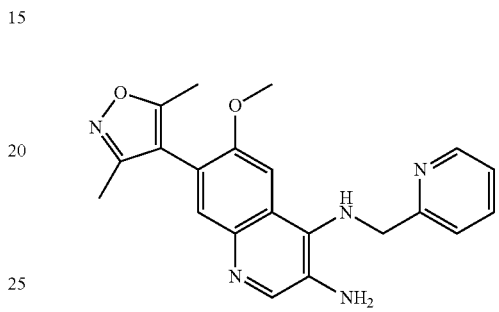

A solution of 4-chloro-7-(3,5-dimethyl-4-isoxazolyl)-6-(methoxy)-3-nitroquinoline (for a preparation see intermediate 18, 2.5 g,) and (2-pyridinylmethyl)amine (1.41 g) in acetonitrile (30 ml) were heated at 80° C. for 2 h. The mixture was extracted with DCM and the organic washed with a saturated solution of sodium hydrogen carbonate, dried over Na2SO4, filtered and concentrated to dryness. The residue was taken-up in diethyl ether, filtered and dried under vacuum. The residue was dissolved in ethanol (20 ml) and HCl (3.8 ml, conc.). Tin (II) chloride dihydrate (5.6 g) was then added in four portions and the reaction mixture was stirred for 1 h at 40° C. The mixture was hydrolysed using sodium hydroxide (1N), extracted with DCM and the organic were dried over Na2SO4. The mixture was filtered through Celite and concentrated to dryness. The crude product was purified by chromatography on silica gel eluting with DCM/methanol (56.5/3.5) to give 7-(3,5-dimethylisoxazol-4-yl)-6-methoxy-N4-(pyridin-2-ylmethyl)quinoline-3,4-diamine (500 mg) as a clear brown foam.

Intermediate 64: 7-(3,5-dimethyl-4-isoxazolyl)-6-(methyloxy)-N4-[(1R)-1-(2-pyridinyl)ethyl]-3,4-quinolinediamine

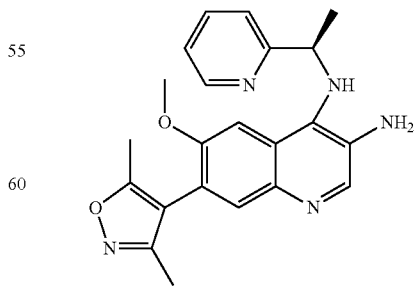

A solution of 4-chloro-7-(3,5-dimethyl-4-isoxazolyl)-6-(methoxy)-3-nitroquinoline (for a preparation see Intermediate 18, 400 mg,) and (R)-1-(pyridin-2-yl)ethanamine (293 mg) in acetonitrile (30 ml) was heated at 60° C. for 2 h. The reaction mixture was extracted with DCM and washed with a saturated solution of sodium hydrogen carbonate. The organic was dried over Na$_2$SO$_4$, filtered and concentrated to dryness. The resulting compound was taken-up in ether, filtered and dried in vacuo. The residue was dissolved in ethanol (20 ml) and HCl (3.8 ml). Tin (II) chloride dihydrate (0.89 g) was then added in four portions and the reaction mixture was stirred for 1 h at 40° C. The reaction mixture was hydrolysed using a solution of sodium hydroxide (1N). The mixture was extracted with DCM, the organic dried over Na$_2$SO$_4$, filtered over Celite and concentrated to dryness. The crude product was purified via flash column chromatography on silica gel eluting with DCM/MeOH (95/5) and the obtained product was taken-up in diisopropylether to give 7-(3,5-dimethyl-4-isoxazolyl)-6-(methyloxy)-N$^4$-[(1R)-1-(2-pyridinyl)ethyl]-3,4-quinolinediamine (250 mg) as a brown powder. LC/MS: Rt 2.62 min.

Intermediate 65: 7-(3,5-dimethyl-4-isoxazolyl)-4-{[(2,4-dimethyl-1,3-thiazol-5-yl)methyl]amino}-6-(methyloxy)-3-quinolinecarboxamide

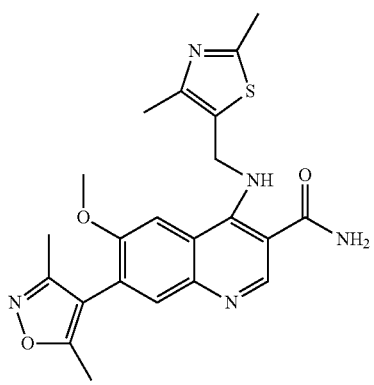 [SMILES: COc1cc2c(NCc3sc(C)nc3C)c(C(N)=O)cnc2cc1-c1c(C)noc1C]

To a solution of 4-chloro-7-(3,5-dimethyl-4-isoxazolyl)-6-(methyloxy)-3-quinolinecarboxamide (for a preparation see Intermediate 56, 0.5 g,) in acetonitrile (50 ml) was added a solution of [(2,4-dimethyl-1,3-thiazol-5-yl)methyl]amine (0.64 g, dihydrochloride available from Matrix Scientific) in acetonitrile (10 ml). The reaction mixture was heated at reflux for 3 h, whereupon another portion of amine (0.5 g) was added. The reaction mixture was refluxed overnight and was then poured into water. The mixture phase was extracted with DCM and the organic dried over Na$_2$SO$_4$ and concentrated to dryness to give a yellow sticky solid. The latter was recrystallised in acetonitrile to give 7-(3,5-dimethyl-4-isoxazolyl)-4-{[(2,4-dimethyl-1,3-thiazol-5-yl)methyl]amino}-6-(methyloxy)-3-quinolinecarboxamide (0.33 g) as white crystals.
LC/MS: MH$^+$438.06, [M−H]$^-$ 436.13

Intermediate 66: 7-(3,5-dimethyl-4-isoxazolyl)-6-(methyloxy)-N$^4$-[1-(2-pyridinyl)ethyl]-3,4-quinolinediamine

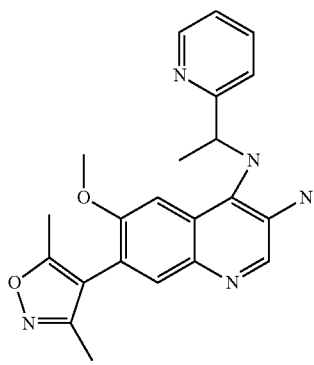 [SMILES: COc1cc2c(NC(C)c3ccccn3)c(N)cnc2cc1-c1c(C)noc1C]

A solution of 4-chloro-7-(3,5-dimethyl-4-isoxazolyl)-6-(methoxy)-3-nitroquinoline (for a preparation see Intermediate 18, 1 g,) and (2-pyridinylmethyl)amine (810 mg) in acetonitrile (30 ml) was heated at 80° C. for 2 h. The mixture was extracted with DCM, washed with a saturated solution of sodium hydrogen carbonate, dried over Na$_2$SO$_4$, filtered and concentrated to dryness. The crude compound was taken-up in diethyl ether, filtered and the fitrate dried under vacuum.

The solid was dissolved in ethanol (20 ml) and hydrochloric acid (3.8 ml, conc). Tin (II) chloride dehydrate (5.6 g) was added in 4 portions and the reaction heated at 40° C. for 1 h. The reaction was hydrolysed with sodium hydroxide (1N) and extracted with DCM. The organic was dried over Na$_2$SO$_4$, filtered through Celite and evaporated to dryness. The residue which was purified by chromatography on silica gel, eluting with DCM/methanol (95:5) to yield 7-(3,5-dimethyl-4-isoxazolyl)-6-(methyloxy)-N$^4$-[1-(2-pyridinyl)ethyl]-3,4-quinolinediamine (600 mg) as a orange oil.

Intermediate 67: 7-(3,5-dimethyl-4-isoxazolyl)-4-{[(5-methyl-3-isoxazolyl)methyl]amino}-6-(methyloxy)-3-quinolinecarboxamide

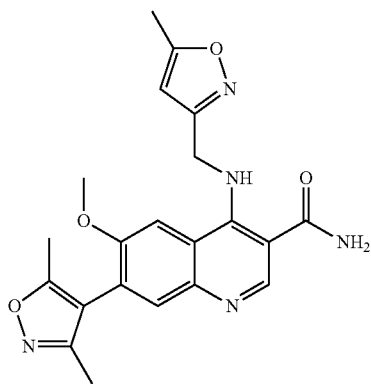 [SMILES: COc1cc2c(NCc3cc(C)on3)c(C(N)=O)cnc2cc1-c1c(C)noc1C]

A solution of 4-chloro-7-(3,5-dimethyl-4-isoxazolyl)-6-(methyloxy)-3-quinolinecarboxamide (for a preparation see Intermediate 56, 331 mg) and [(5-methyl-3-isoxazolyl)methyl]amine (2.5 eq) in butanol (20 ml) was heated to 110° C. for 4 h. The reaction mixture was evaporated to dryness and hydrolysed with water. The mixture was extracted with DCM and the organic dried over Na$_2$SO$_4$, filtered and concentrated to dryness (280 mg). Used without purification in the subsequent reaction (Example 52).

Intermediate 68: 7-(3,5-dimethyl-4-isoxazolyl)-6-(methyloxy)-N$^4$-(2-thienylmethyl)-3,4-quinolinediamine

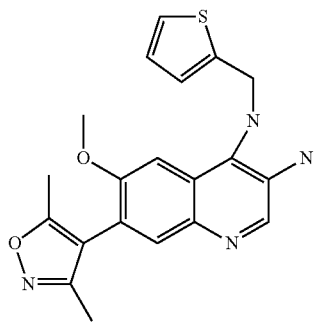 [SMILES: COc1cc2c(NCc3cccs3)c(N)cnc2cc1-c1c(C)noc1C]

To a magnetically stirred solution 4-chloro-7-(3,5-dimethyl-4-isoxazolyl)-6-(methyloxy)-3-quinolinecarboxamide (for a preparation see Intermediate 56, 1.5 g) in acetonitrile (10 ml) in a Shlenk tube was added (2-thienylmethyl)amine (1.53 g). The Shlenk tube was sealed and the reaction mixture heated at 80° C. for 24 h. The water was added to the reaction followed by an aqueous saturated solution of sodium hydrogen carbonate. The mixture was extracted with DCM and the organic phase dried over Na$_2$SO$_4$, filtered and concentrated to dryness. The resulting crude compound was purified by chromatography on silica gel (25 g) eluting with DCM/methanol (95:5) to give 7-(3,5-dimethyl-4-isoxazolyl)-6-(methyloxy)-N$^4$-(2-thienylmethyl)-3,4-quinolinediamine (1.493 g) as a cream coloured powder. LC/MS: MH$^+$409.12, [M–H]$^-$ 407.17, Rt 2.70 min Intermediate 69: 7-(3,5-dimethyl-4-isoxazolyl)-N-[(2,4-dimethyl-1,3-thiazol-5-yl)methyl]-6-(methyloxy)-3-nitro-4-quinolinamine

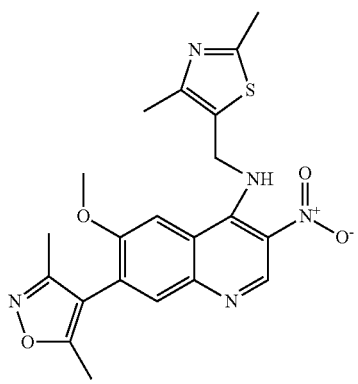 [SMILES: COc1cc2c(NCc3sc(C)nc3C)c([N+](=O)[O-])cnc2cc1-c1c(C)noc1C]

To a solution of 4-chloro-7-(3,5-dimethyl-4-isoxazolyl)-6-(methyloxy)-3-nitroquinoline (for a preparation see Intermediate 18, 1.5 g) in acetonitrile was added [(2,4-dimethyl-1,3-thiazol-5-yl)methyl]amine (1.6 g) and the resulting mixture was stirred overnight at 80° C. Another portion of amine (0.64 g) was added and the mixture was stirred at 80° C. for 6 h. The reaction mixture was diluted with water, extracted with DCM and the organic phase were dried over Na$_2$SO$_4$, and concentrated to dryness to give a dark red oil. The residue was purified by flash chromatography on silica gel, eluting with DCM/methanol (99:1 then 95:5) to give 7-(3,5-dimethyl-4-isoxazolyl)-N-[(2,4-dimethyl-1,3-thiazol-5-yl)methyl]-6-(methyloxy)-3-nitro-4-quinolinamine (1.13 g) as an orange oil.

LC/MS: MH$^+$440.05, [M–H]$^-$ 438.11

Intermediate 70: 7-(3,5-dimethyl-4-isoxazolyl)-N$^4$-[(2,4-dimethyl-1,3-thiazol-5-yl)methyl]-6-(methyloxy)-3,4-quinolinediamine

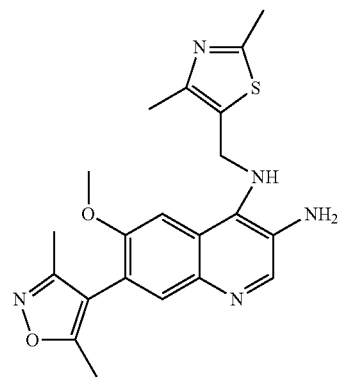 [SMILES: COc1cc2c(NCc3sc(C)nc3C)c(N)cnc2cc1-c1c(C)noc1C]

To a solution of 7-(3,5-dimethyl-4-isoxazolyl)-N-[(2,4-dimethyl-1,3-thiazol-5-yl)methyl]-6-(methyloxy)-3-nitro-4-quinolinamine (for a preparation see intermediate 69, 1.13 g) in ethanol was added hydrochloric acid (2 ml, conc). Tin (II) chloride dihydrate (2.32 g) was added and the mixture was stirred at 40° C. for 1 h. The reaction mixture was cooled, diluted with water and basified using sodium hydroxide solution (1N). The formed precipitate was filtered through Celite and rinsed with DCM. The filtrate was washed with water and the organic was dried over Na$_2$SO$_4$ and evaporated to dryness. The residue was purified by flash chromatography on silica gel eluting with DCM/methanol (98:2 then 93:7) to give 7-(3,5-dimethyl-4-isoxazolyl)-N$^4$-[(2,4-dimethyl-1,3-thiazol-5-yl)methyl]-6-(methyloxy)-3,4-quinolinediamine (0.6 g) as a beige foam.

LC/MS: MH$^+$410.10, [M–H]$^-$ 408.18.

Intermediate 71: N-[7-(3,5-dimethyl-4-isoxazolyl)-4-{[(2,4-dimethyl-1,3-thiazol-5-yl)methyl]amino}-6-(methyloxy)-3-quinolinyl]tetrahydro-2H-pyran-4-carboxamide

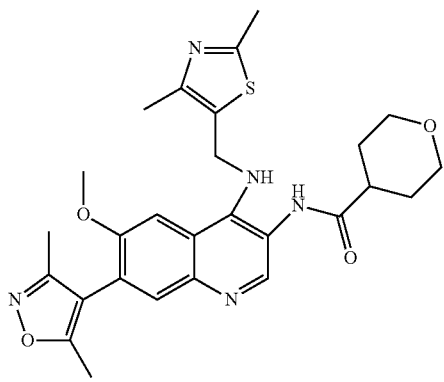 [SMILES: COc1cc2c(NCc3sc(C)nc3C)c(NC(=O)C3CCOCC3)cnc2cc1-c1c(C)noc1C]

To a solution of tetrahydro-2H-pyran-4-carboxylic acid (0.381 g, intermediate 69) in DCM (60 ml) were successively added triethylamine (0.41 ml) then HATU (1.115 g) and the resulting mixture was stirred for 20 min room temperature. 7-(3,5-dimethyl-4-isoxazolyl)-$N^4$-[(2,4-dimethyl-1,3-thiazol-5-yl)methyl]-6-(methyloxy)-3,4-quinolinediamine (0.6 g, intermediate 69) was added and the mixture stirred at ambient temperature overnight. The reaction mixture was poured into water and extracted with DCM. The organic phase was washed with a dilute sodium hydroxide solution and then with water. The organic phase was dried over $Na_2SO_4$ and concentrated to dryness. The crude residue was purified by flash silica gel chromatography eluting DCM/methanol (99:1 then 95:5) to give the desired product as a beige sticky solid (0.71 g). The solid was triturated with hot diisopropylether to give N-[7-(3,5-dimethyl-4-isoxazolyl)-4-{[(2,4-dimethyl-1,3-thiazol-5-yl)methyl]amino}-6-(methyloxy)-3-quinolinyl]tetrahydro-2H-pyran-4-carboxamide (0.6 g) as cream coloured crystals.

LC-HRMS: $ES^+$ exact mass calculated for $C_{27}H_{32}N_5O_4S_1$ 522.2175 $MH^+$, found: 522.2225

Intermediate 72: 7-(3,5-dimethyl-4-isoxazolyl)-4-{[(5-methyl-2-furanyl)methyl]amino}-6-(methyloxy)-3-quinolinecarboxamide

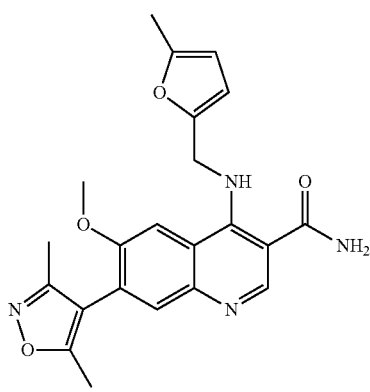 [SMILES: COc1cc2c(NCc3ccc(C)o3)c(C(N)=O)cnc2cc1-c1c(C)noc1C]

A mixture of 4-chloro-7-(3,5-dimethyl-4-isoxazolyl)-6-(methyloxy)-3-quinolinecarboxamide (for a preparation see Intermediate 56, 200 mg,) and [(5-methyl-2-furanyl)methyl]amine (200 mg) in 1,4-dioxane was heated to reflux overnight. The reaction mixture was evaporated to dryness and the residue was taken-up in DCM and washed with a saturated solution of sodium hydrogen carbonate. The organic was dried over $Na_2SO_4$, filtered and concentrated. The residue was purified by chromatography to give 7-(3,5-dimethyl-4-isoxazolyl)-4-{[(5-methyl-2-furanyl)methyl]amino}-6-(methyloxy)-3-quinolinecarboxamide (177 mg) as a beige powder.

LC/MS: Rt 2.75, $MH^+$406.99, $[M-H]^-$ 405.05

Example 1

1-[2-(tert-butyl)phenyl]-7-(3,5-dimethyl-4-isoxazolyl)-1,3-dihydro-2H-imidazo[4,5-c]quinolin-2-one

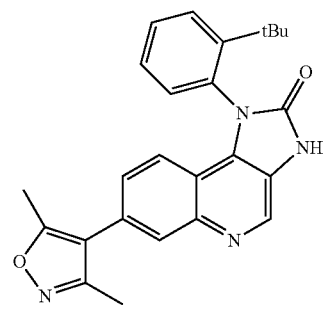 [SMILES: Cc1noc(C)c1-c1ccc2c(c1)ncc1[nH]c(=O)n(-c3ccccc3C(C)(C)C)c12]

A mixture of 7-(3,5-dimethyl-4-isoxazolyl)-$N^4$-(phenylmethyl)-3,4-quinolinediamine (for a preparation see Intermediate 28, 0.2 g, 0.52 mmol), Boc anhydride (2 g, 9.17 mmol) and triethyl amine (0.1 g) was heated at 80° C. for 2 h. Diphenylether (3 g) was then added and the reaction mixture was heated to 180° C. for 3 h. After cooling, the mixture was treated with aqueous sodium hydroxide and washed with DCM. The aqueous phase was acidified with acetic acid and extracted with DCM, washed with water, dried over $Na_2SO_4$ and concentrated. The resulting residue was precipitated with a mixture of DCM/hexane to give the title compound (0.044 g, 20%). $^1$H NMR (300 MHz, $CDCl_3$, ppm) δ: 10.47 (brs, 1H), 8.85 (s, 1H), 7.93 (s, 1H), 7.78 (d, J=8.3 Hz, 1H), 7.58 (dd, J=8.3 7.4 Hz, 1H), 7.39 (dd, J=7.7, 7.4 Hz, 1H), 7.17 (d, J=8.9 Hz, 1H), 7.05 (d, J=8.9 Hz, 1H), 6.82 (d, J=8.7 Hz, 1H), 2.37 (s, 3H), 2.24 (s, 3H), 1.24 (s, 9H). (APCI-MS) m/z 413 MH+, Rt 2.92 min. LC-HRMS $ES^+$ exact mass calculated for $C_{25}H_{24}N_4O_2$ 413.1978 $MH^+$, found: 413.2018, Rt 2.67 min.

The following examples were prepared in an analogous manner to Example 1:

| Ex | R¹ | Intermediate | LC-HRMS | NMR ¹H NMR (300 MHz), |
|---|---|---|---|---|
| 2 | 2-chlorobenzyl | 29 | Target Mass for C₂₂H₁₇N₄O₂Cl: 405.1118 MH⁺. Found: 405.1132; Rt 3.06 min | CDCl3, δ: 9.81 (s, 1H), 8.08 (brs, 1H), 7.69 (d, J = 8.9 Hz, 1H), 7.48 (d, J = 8.9 Hz, 1H), 7.35-7.20 (m, 2H), 7.10 (dd, J = 7.7, 7.3 Hz, 1H), 6.84 (d, J = 7.5 Hz, 1H), 5.61 (s, 2H), 2.40 (s, 3H), 2.26 (s, 3H). |
| 3 | benzyl | 30 | Target Mass for C₂₂H₁₈N₄O₂: 371.1508 MH⁺ Found: 371.1507; Rt 2.37 min | CDCl3, δ: 8.86 (s, 1H), 7.97 (s, 1H), 7.92 (d, J = 8.8 Hz, 1H), 7.35-7.31 (m, 6H), 5.58 (s, 2H), 2.38 (s, 3H), 2.24 (s, 3H). |
| 4 | cyclohexylmethyl | 31 | Target Mass for C₂₂H₂₄N₄O₂: 377.1978 MH⁺ Found: 377.1996; Rt 2.66 min | CDCl3, δ: 11.04 (brs, 1H), 8.84 (s, 1H), 8.07 (d, J = 8.9 Hz, 1H), 8.02 (d, J = 1.7 Hz, 1H), 7.47 (dd, J = 7.7, 7.4 Hz, 1H), 4.18 (d, J = 7.5 Hz, 2H), 2.45 (s, 3H), 2.32 (s, 3H), 2.03-1.08 (m, 11H).) HH) |
| 5 | neopentyl | 32 | Target Mass for C₂₀H₂₂N₄O₂: 351.1821 MH⁺ Found: 351.1797; Rt 2.43 min | CDCl3, δ: 10.92 (brs, 1H), 9.02 (s, 1H), 8.52 (d, J = 9 Hz, 1H), 8.20 (s, 1H), 7.62 (dd, J = 8.9, 1.7 Hz, 1H), 4.49 (s, 2H), 2.66 (s, 3H), 2.52 (s, 3H), 1.29 (s, 9H). |
| 6 | 2-OCF₃-benzyl | 33 | Target Mass for C₂₂H₁₅F₃N₄O₃: 441.1174 MH⁺ Found: 441.1259; Rt 2.47 min | DMSO-d6, δ: 11.68 (brs, 1H), 8.62 (s, 1H), 7.80 (s, 1H), 7.70 (dd, J = 7.7, 1.7 Hz, 1H), 7.66-7.46 (m, 3H), 6.81 (d, J = 8.9 Hz, 1H), 2.21 (s, 3H), 2.03 (s, 3H). |
| 7 | 1-phenylethyl | 34 | Target Mass for C₂₃H₂₀N₄O₂ 385.1664 MH⁺ Found: 385.1690; Rt 2.48 min | DMSO-d6, δ: 11.7 (brs, 1H), 8.66 (s, 1H), 7.84 (d, J = 1.7 Hz, 1H), 7.37-7.09 (m, 7H), 6.15 (q, J = 7 Hz, 1H), 2.30 (s, 3H), 2.12 (s, 3H), 1.86 (d, J = 7.2 Hz, 3H). |
| 8 | 4-fluorobenzyl | 35 | Target Mass for C₂₂H₁₇FN₄O₂: 389.1414 MH⁺ Found: 389.1379; Rt 2.40 min | CDCl3, δ: 8.88 (s, 1H), 7.98 (d, J = 1.5 Hz, 1H), 7.89 (d, J = 8.9 Hz, 1H), 7.31-7.27 (dd, J = 8.1, 1.7 Hz 1H), 7.26-7.21 (m, 3H), 7.00 (t, J = 8.5 Hz, 2H), 5.55 (s, 2H), 2.40 (s, 3H), 2.26 (s, 3H). |
| 9 | 2-pyridinylmethyl | 36 | Target Mass for C₂₁H₁₇N₅O₂: 372.1460 MH⁺ Found: 372.1472; Rt 2.06 min | DMSO-d6, δ: 8.80 (s, 1H), 8.51 (m, 1H), 8.08 (d, J = 8.8 Hz 1H), 7.99 (d, J = 1.7 Hz, 1H), 7.81 (dd, J = 7.8, 1.9 Hz, 1H), 7.48 (dd, J = 8.7, 1.7 Hz, 1H), 7.38 (d, J = 7.9 Hz 1H), 7.33 (m, 1H), 5.66 (s, 2H), 2.46 (s, 3H), 2.28 (s, 3H). |

Example 10

7-(3,5-dimethyl-4-isoxazolyl)-8-(methoxy)-1-(2-pyridinylmethyl)-1,3-dihydro-2H imidazo[4,5-c]quinolin-2-one The mixture of 4-chloro-7-(3,5-dimethyl-4-isoxazolyl)-6-(methoxy)-3-quinolinecarboxamide (for a preparation see Intermediate 40, 6 g, 18 mmol) was reacted with 2-aminomethylpyridine (2.5 eq, 4.23 g, 45 mmol) in CH₃CN (100 ml) was stirred at 110° C. for 4 h. The reaction mixture was concentrated in vacuo. The residue was partitioned between water and DCM. The organic layer was dried over Na₂SO₄ and concentrated to dryness to give 7-(3,5-dimethyl-4-isoxazolyl)-6-(methoxy)-4-[(2-pyridinylmethyl)amino]-3-quinoline carboxamide (5.84 g) which was used in the next step without purification.

An excess of [bis(trifluoroacetoxy)iodo]benzene (19.35 g, 45 mmol) was added to a solution of the previous carboxamide intermediate (5.84 g, 15 mmol). The mixture was stirred at 50° C. for 12 h and then concentrated. The residue was partitioned between DCM and water, the organic layer was dried over Na$_2$SO$_4$, filtered and concentrated in vacuo. The crude product was purified by flash chromatography on silica gel (DCM/MeOH, 95:5), then triturated with diethylether to give the title compound as a beige powder (3.9 g, 53.7%).

LC-HRMS ES$^+$ exact mass calculated for C22H19N5O3: 402.1566 MH$^+$. Found 402.1574, Rt=2.14 min. (APCI-MS) m/z 402.10 MH$^+$, Rt 2.39 min.

Example 11

7-(3,5-dimethyl-4-isoxazolyl)-8-(methoxy)-1-[(1R)-1-(2-pyridinyl)ethyl]-1,3-dihydro-2H-imidazo[4,5-c]quinolin-2-one

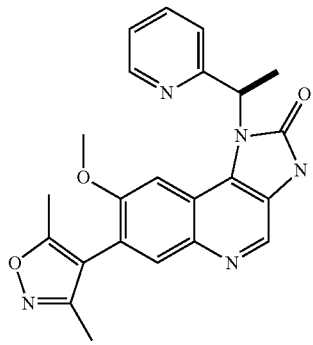 [SMILES: COc1cc2c(cc1-c1c(C)noc1C)ncc1[nH]c(=O)n([C@H](C)c3ccccn3)c12]

The mixture of 4-chloro-7-(3,5-dimethyl-4-isoxazolyl)-6-(methoxy)-3-quinolinecarboxamide (for a preparation see intermediate 40, 6 g, 18 mmol) was reacted with (1R)-1-(2-pyridinyl)ethanamine (2 eq., 4.43 g, 36 mmol) in CH$_3$CN (100 ml) and was stirred at 110° C. for 4 h. The reaction mixture was concentrated in vacuo. The residue was partitioned between water and DCM. The organic layer was dried over Na$_2$SO$_4$ and concentrated to dryness to give 7-(3,5-dimethyl-4-isoxazolyl)-6-(methoxy)-4-{[(1R)-1-(2-pyridinyl)ethyl]-amino}-3-quinolinecarboxamide which was used in the next step without purification. The carboxamide intermediate (6 g) was treated with an excess of [bis(trifluoroacetoxy)iodo]benzene (19.35 g, 45 mmol) in CH$_3$CN (100 ml), the mixture was stirred at room temperature overnight. The reaction mixture was concentrated in vacuo, the resulting residue was dissolved in DCM and washed with water. The crude product was purified by flash chromatography on silica gel (DCM/MeOH, 95:5), the resulting compound was dissolved in DCM and precipitated from diethylether to give the title compound as an off-white powder (2.5 g, 33%)

LC-HRMS ES$^+$ exact mass calculated for C$_{23}$H$_{21}$N$_5$O$_3$: 416.1722 MH$^+$. Found 416.1736, Rt=2.22 min. (APCI-MS) m/z 415.97 MH$^+$, Rt 2.5 min.

For an alternative preparation of this compound see Example 36.

Example 12

7-(3,5-dimethyl-4-isoxazolyl)-8-(methoxy)-1-{2-[(trifluoromethyl)oxy]phenyl}-1,3-dihydro-2H-imidazo[4,5-c]quinolin-2-one

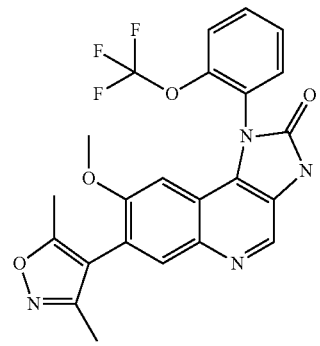 [SMILES: COc1cc2c(cc1-c1c(C)noc1C)ncc1[nH]c(=O)n(-c3ccccc3OC(F)(F)F)c12]

A mixture of intermediate 50 (0.1 g, 0.2 mmol) and diphenyl phosphoryl azide (0.065 g, 0.24 mmol) in DMF (10 ml) was heated at 110° C. for 2 h. The reaction mixture was concentrated to dryness. The crude product was purified by flash chromatography on silica gel eluting with DCM/MeOH (98:2), the resulting compound was re-crystallised from diisopropyl ether to give the title compound as a yellow solid (0.02, %).

$^1$H NMR (300 MHz, DMSO-d6, ppm) δ: 8.74 (s, 1H), 7.99 (dd, J=1.5, 7.7 Hz, 1H), 7.92 (s, 1H), 7.89 (m, 2H), 7.84-7.77 (m, 1H), 6.33 (s, 1H), 3.37 (s, 3H), 2.33 (s, 3H), 2.12 (s, 3H).

LC-HRMS Target Mass calculated for C$_{23}$H$_{17}$F$_3$N$_4$O$_4$: 471.1280 MH$^+$, Found: 471.1250; Rt 2.47 min.

The following examples were prepared in an analogous manner to example 12:

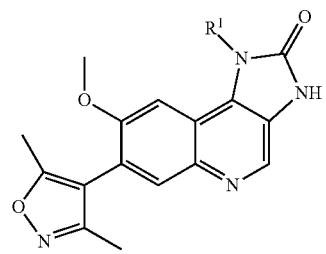

| Ex | R$^1$ | Intermediate | LC-HRMS | NMR $^1$H NMR (300 MHz), |
|---|---|---|---|---|
| 13 | | 49 | Target Mass for C$_{26}$H$_{26}$N$_4$O$_3$: 443.2083 MH$^+$. Found: 443.2067; Rt 2.63 min | DMSO-d6, δ: 8.66 (s, 1H), 7.85 (s, 1H), 7.82 (s, 1H), 7.62 (dd, J = 7.0-7.0 Hz, 1H), 7.47 (dd, J = 7.1-7.1 Hz, 1H), 7.35 (d, J = 7.0, 1H), 6.06 (s, 1H), 3.24 (s, 3H), 2.26 (s, 3H), 2.04 (s, 3H), 1.23 (s, 9H). |

-continued

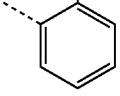

| Ex | R¹ | Inter- medi- ate | LC-HRMS | NMR ¹H NMR (300 MHz), |
|---|---|---|---|---|
| 14 | 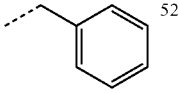 F | 51 | Target Mass for $C_{22}H_{17}FN_4O_3$: 405.1363 MH⁺. Found: 405.1377; Rt 2.32 min | DMSO-d6, δ: 8.54 (s, 1H), 7.73 (brs, 2H), 7.63-7.60 (m, 1H), 7.53-7.50 (m, 1H), 7.40-7.41 (m, 1H), 6.23 (s, 1H), 3.21 (s, 3H), 2.41 (s, 3H), 1.93 (s, 3H). |
| 15 | 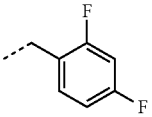 | 52 | Target Mass for $C_{23}H_{20}N_4O_3$: 401.1613 MH⁺. Found: 401.1595; Rt 2.39 min | DMSO-d6, δ: 8.42 (s, 1H), 7.60 (s, 1H), 7.20-7.09 (m, 5H), 6.98 (s, 1H), 5.40 (s, 2H), 3.40 (s, 3H), 2.05 (s, 3H), 1.85 (s, 3H). |
| 16 | 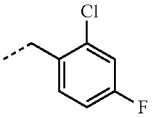 F F | 53 | Target Mass for $C_{23}H_{18}F_2N_4O_3$: 437.1425 MH⁺. Found: 437.1373; Rt 2.47 min | DMSO-d6, δ: 8.56 (s, 1H), 7.76 (s, 1H), 7.34 (dd, J = 9.3, 9.3 Hz, 1H), 7.15-6.87 (m, 3H), 5.53 (s, 2H), 3.60 (s, 3H), 2.20 (s, 3H), 2.00 (s, 3H). |
| 17 | Cl F | 54 | Target Mass for $C_{23}H_{18}ClFN_4O_3$: 453.1129 MH⁺. Found: 453.1119; Rt 2.62 min | CDCl₃, δ: 8.76 (s, 1H), 7.81 (s, 1H), 7.22 (d, J = 7.7 Hz, 1H), 6.85 (d, J = 6.8 Hz, 1H), 6.79 (s, 1H), 5.60 (s, 2H), 3.51 (s, 3H), 2.22 (s, 3H), 2.07 (s, 3H). |

Example 18

1-[2-(tert-butyl)phenyl]-7-(3,5-dimethyl-4-isoxazolyl)-1H-imidazo[4,5-c]quinoline

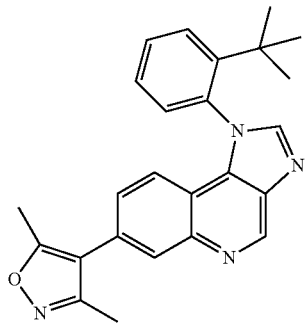 [SMILES: Cc1noc(C)c1-c1ccc2c(c1)ncc1ncn(-c3ccccc3C(C)(C)C)c12]

To a solution of 7-(3,5-dimethyl-4-isoxazolyl)-N⁴-(phenylmethyl)-3,4-quinolinediamine (for aq preparation see Intermediate 28, 0.2 g, 0.52 mmol) in DCM (10 ml) were added HOBT (0.081 g, 0.62 mmol), EDCI (0.118 g, 0.62 mmol), Et₃N (0.062 g, 0.62 mmol) and formic acid (0.025 g, 0.52 mmol). The reaction mixture was stirred at room temperature overnight, then poured into water and extracted with DCM. The organic phase was washed with water, dried over Na₂SO₄ and concentrated. The crude solid was re-crystallized from EtOAc to give the title compound as off-white crystals (0.1 g, 48%). M.p: 216° C. ¹H NMR (300 MHz, CDCl3, ppm) δ: 9.36 (s, 1H), 8.06 (s, 1H), 8.01 (s, 1H), 7.73 (d, J=7.2 Hz, 1H), 7.56 (dd, J=8.1, 8.1 Hz, 1H), 7.34 (dd, J=7.7, 7.7 Hz, 1H), 7.15-7.06 (m, 2H), 2.36 (s, 3H), 2.23 (s, 3H), 1.07 (s, 9H). LC-HRMS: ES⁺ exact mass calculated for $C_{25}H_{24}N_4O$: 397.2028 MH⁺, found: 397.2021, Rt 3.03 min.

The following examples were prepared in an analogous manner to example 18 from the corresponding intermediates:

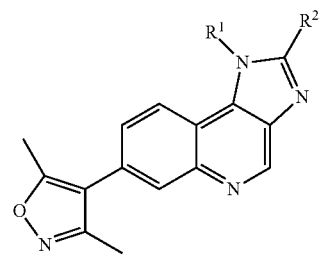

| Ex | R¹ | R² | Inter- medi- ate | TOF-MS | ¹H NMR (300 MHz), |
|---|---|---|---|---|---|
| 19 | tBu 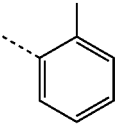 | CH₃ | 28 | Exact mass calculated for $C_{26}H_{26}N_4O$: 411.2185 MH⁺ Found: 411.2154, Rt 3.08 min | CDCl3, δ: 9.33 (s, 1H), 8.13 (brs, 1H), 7.83 (d, J = 8.3 Hz, 1H), 7.65 (dd, J = 8.3, 7.4 Hz, 1H), 7.44 (dd, J = 7.7, 7.5 Hz, 1H), 7.16 (dd, J = 8.7, 1.7 Hz, 1H), 7.09 (dd, J = 7.7, 1.3 Hz, 1H), 7.00 (d, J = 8.5 Hz, 1H), 2.48 (s, 3H), 2.43 (s, 3H), 2.29 (s, 3H), 1.08 (s, 9H). |

-continued

| Ex | R¹ | R² | Intermediate | TOF-MS | ¹H NMR (300 MHz), |
|---|---|---|---|---|---|
| 20 | tBu (phenyl) | —(CH$_2$)$_2$OCH$_3$ | 28 | Exact Mass calculated for C$_{28}$H$_{30}$N$_4$O$_2$: 455.2447 MH⁺. Found: 455.2455; Rt 3.04 min | CDCl3, δ: 9.22 (s, 1H), 7.94 (brs, 1H), 7.66 (d, J = 7.9 Hz, 1H), 7.49 (dd, J = 7.4, 7.2 Hz, 1H), 7.28 (dd, J = 7.4, 7.2 Hz, 1H), 6.99 (dd, J = 7.4, 7.2 Hz, 2H), 6.82 (d, J = 8.7 Hz, 1H), 3.86-3.70 (m, 2H), 3.19 (s, 3H), 2.98-2.68 (m, 2H), 2.27 (s, 3H), 2.14 (s, 3H), 0.91 (s, 9H). |
| 21 | tBu (phenyl) | benzyl | 28 | Exact Mass calculated for C$_{32}$H$_{30}$N$_4$O: 487.2498 MH⁺. Found: 487.2532; Rt 3.46 min | CDCl3, δ: 9.48 (s, 1H), 8.17 (brs, 1H), 7.92 (d, J = 8.3 Hz, 1H), 7.70 (dd, J = 8.3, 8.3 Hz, 1H), 7.39-7.26 (m, 4H), 7.25-7.15 (m, 3H), 7.05 (d, J = 8.7 Hz, 1H), 6.88 (d, J = 7.9 Hz, 1H), 4.39 (d, J = 15.4 Hz, 1H), 4.00 (d, J = 15.4 Hz, 1H), 2.50 (s, 3H), 2.37 (s, 3H), 1.17 (s, 9H). |
| 22 | tBu (phenyl) | iso-propyl | 28 | Exact Mass calculated for C$_{28}$H$_{30}$N$_4$O: 439.2498 MH⁺. Found: 439.2526; Rt 3.36 min | CDCl3, δ: 9.34 (s, 1H), 8.08 (brs, 1H), 7.80 (d, J = 8.1 Hz, 1H), 7.61 (dd, J = 7.2, 7.2 Hz, 1H), 7.39 (dd, J = 7.2, 7.2 Hz, 1H), 7.15-7.06 (m, 2H), 6.89 (d, J = 8.5 Hz, 1H), 2.86 (q, J = 7 Hz, 1H), 2.38 (s, 3H), 2.24 (s, 3H), 1.51 (d, J = 7 Hz, 3H), 1.20 (d, J = 7 Hz, 3H). |
| 23 | benzyl | CH3 | 30 | Exact Mass calculated for C$_{23}$H$_{20}$N$_4$O: 369.1715 MH⁺. Found: 369.1679; Rt 2.55 min | CDCl3, δ: 9.28 (s, 1H), 8.09 (brs, 1H), 7.94 (d, J = 8.7 Hz, 1H), 7.35-7.24 (m, 4H), 7.02 (d, J = 7.9 Hz, 2H), 5.76 (s, 2H), 2.65 (s, 3H), 2.40 (s, 3H), 2.26 (s, 3H). |
| 24 | benzyl | iso-propyl | 30 | Exact Mass calculated for C$_{25}$H$_{24}$N$_4$O: 397.2028 MH⁺. Found: 397.2035; Rt 2.77 min | CDCl3, δ: 9.33 (s, 1H), 8.22 (brs, 1H), 7.92 (d, J = 8.8 Hz, 1H), 7.34-7.24 (m, 4H), 6.99 (d, J = 7.9 Hz, 2H), 5.81 (s, 2H), 3.23 (q, J = 7 Hz, 1H), 2.40 (s, 3H), 2.26 (s, 3H), 1.41 (d, J = 7 Hz, 6H). |
| 25 | benzyl | tert-butyl | 30 | Exact Mass calculated for C$_{26}$H$_{26}$N$_4$O: 411.2185 MH⁺. Found: 411.2146; Rt 2.93 min | CDCl3, δ: 9.24 (s, 1H), 8.15 (brs, 1H), 7.73 (d, J = 8.9 Hz, 1H), 7.25-7.12 (m, 4H), 6.86 (J = 7.4 Hz, 2H), 5.94 (s, 2H), 2.30 (s, 3H), 2.16 (s, 3H), 1.44 (s, 9H). |
| 26 | benzyl | —(CH$_2$)$_2$OCH$_3$ | 30 | Exact Mass calculated for C$_{25}$H$_{24}$N$_4$O$_2$: 413.1978 MH⁺. Found: 413.1940; Rt 2.59 min | DMSO-d6, δ: 9.35 (s, 1H), 8.29 (d, J = 8.7 Hz, 1H), 8.21 (d, J = 1.7 Hz, 1H), 7.64 (dd, J = 8.7, 1.7 Hz, 1H), 7.49-7.28 (m, 2H), 7.17 (d, J = 7.2 Hz, 1H), 6.13 (s, 2H), 3.93 (t, J = 6.6 Hz, 2H), 3.35 (t, J = 6.6 Hz, 2H), 2.55 (s, 3H), 2.37 (s, 3H). |

Example 27

7-(3,5-dimethyl-4-isoxazolyl)-8-(methoxy)-1-(2-pyridinylmethyl)-2-(tetrahydro-2H-pyran-4-yl)-1H-imidazo[4,5-c]quinoline

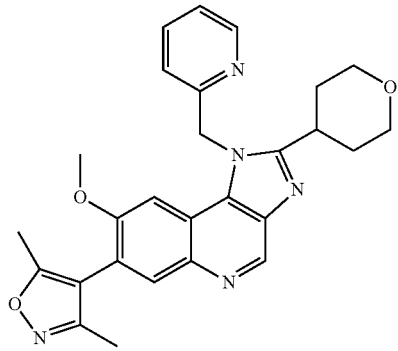 [SMILES: COc1cc2c(cc1-c1c(C)noc1C)ncc1nc(C3CCOCC3)n(Cc3ccccn3)c12]

To a solution of 7-(3,5-dimethyl-4-isoxazolyl)-6-(methoxy)-$N^4$-(2-pyridinylmethyl)-3,4-quinolinediamine (for a preparation see Intermediate 38, 0.5 g, 1.33 mmol) in DCM (20 ml) was added tetrahydro-2H-pyran-4-carbonyl chloride (1.1 eq., 1.46 mmol, 0.15 g, Apollo Scientific) at 0° C., the mixture was stirred at 0° C. for 30 minutes. The reaction mixture was hydrolysed with saturated aqueous Sodium hydrogen carbonate and extracted with DCM. The organic phase was dried over $Na_2SO_4$ and concentrated to give the crude product which was used in the next step without purification. AcOH (5 ml) was added to the crude product and the mixture was stirred at 100° C. overnight. The reaction mixture was concentrated under reduce pressure, hydrolised with sodium hydroxide 1N and extracted with DCM. The organic phase was dried over over $Na_2SO_4$, evaporated under reduce pressure. The residue was purified by flash chromatography on silica gel (DCM/MeOH, 95:5) and the compound was re-crystallised from acetonitrile to give the title compound as an off-white powder (0.13 g, 21%)

LC-HRMS: $ES^+$ exact mass calculated for $C_{27}H_{27}N_5O_3$: 470.2192 ($MH^+$). Found: 470.2153, Rt=2.18 min. (APCI-MS) m/z: 471.01 $MH^+$, Rt=2.51 min The following examples were prepared in an analogous manner to example 27:

| Ex | $R^1$ | $R^{2a}$ | LC-HRMS | $^1$H NMR (300 MHz) or LC/MS |
|---|---|---|---|---|
| 28 | benzyl | tetrahydropyran-4-yl | exact mass calculated for $C_{28}H_{28}N_4O_3$: 469.2240 $MH^+$. Found: 469.2265, Rt = 2.54 min. | DMSO-d6, δ: 9.12 (s, 1H), 7.92 (s, 1H), 7.45-7.23 (m, 4H), 7.12 (d, J = 7.2 Hz, 2H), 6.11 (s, 2H), 4.02-3.87 (m, 2H), 3.59 (s, 3H), 3.58-3.45 (m, 2H), 2.26 (s, 3H), 2.06 (s, 3H), 2.04-1.92 (m, 2H), 1.91-1.80 (m, 2H). |
| 29 | 1-phenylethyl | tetrahydropyran-4-yl | exact mass calculated for $C_{29}H_{30}N_4O_3$: 483.2396 $MH^+$. Found: 483.2368, Rt = 2.62. (APCI-MS) m/z: 482.93 (M + H)$^+$, Rt = 2.62 min | (APCI-MS) m/z: 482.93 (M + H)$^+$, Rt = 2.92 min |
| 30 | 1-phenylethyl | —CH2OCH$_3$ | exact mass calculated for $C_{26}H_{26}N_4O_3$: 443.2083 $MH^+$. Found: 443.2109, Rt = 2.71. LCMS AP+ Found 442.94, Rt = 2.93 min. | DMSO-d6, δ: 9.16 (s, 1H), 7.93 (s, 1H), 7.49-7.21 (m, 5H), 6.77 (bs, 1H), 6.52-6.34 (m, 1H), 5.05-4.79 (m, 2H), 3.36 (s, 6H), 2.26 (s, 3H), 2.08 (d, J = 7 Hz, 3H), 2.05 (s, 3H). |

Example 31

7-(3,5-dimethyl-4-isoxazolyl)-8-(methoxy)-1-[(1R)-1-phenylethyl]-2-(tetrahydro-2H-pyran-4-yl)-1H-imidazo[4,5-c]quinoline

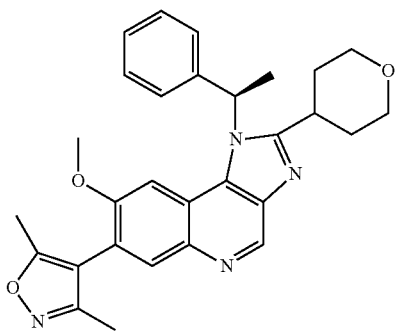 [SMILES: COc1cc2c(cc1-c1c(C)noc1C)ncc1nc(C3CCOCC3)n([C@H](C)c3ccccc3)c12]

To a solution of intermediate 39 (0.5 g, 1.28 mmol) in DCM (25 ml) at 0° C. was added tetrahydro-2H-pyran-4-carbonyl chloride (1.05 eq., 1.4 mmol, 0.15 g, Apollo Scientific), the mixture was then stirred at 0° C. for 15 minutes. The reaction mixture was hydrolysed with saturated aqueous Sodium hydrogen carbonate and extracted with DCM. The organic phase was dried over $Na_2SO_4$ and concentrated to give the crude product which was used in the next step without purification. AcOH was added to the crude product and the mixture was stirred at 100° C. overnight. The reaction mixture was concentrated under reduce pressure, hydrolised with sodium hydroxide 1N and extracted with DCM. The organic phase was dried over over $Na_2SO_4$, evaporated under reduce pressure. The residue was purified by flash chromatography on silica gel (DCM/MeOH, 95:5) to give the title compound as a white powder (0.16 g, 26%).

(APCI-MS) m/z 483 MH$^+$, Rt 2.93 min. $[\alpha]_D^{20}$=−38.7° (c=0.8005 g/100 ml, CHCl$_3$).

$^1$H NMR (300 MHz, DMSO-d6, ppm) δ: 9.13 (s, 1H), 7.90 (s, 1H), 7.51-7.21 (m, 5H), 6.73 (bs, 1H), 6.51 (s, 1H), 4.09-3.85 (m, 2H), 3.69-3.45 (m, 2H), 3.31 (s, 3H), 2.27 (s, 3H), 2.07 (d, J=7 Hz, 3H), 2.06 (s, 3H), 2.04-1.92 (m, 2H), 1.91-1.80 (m, 2H).

Example 32

7-(3,5-dimethyl-4-isoxazolyl)-8-(methoxy)-1-[(1R)-1-phenylethyl]-1H-[1,2,3]triazolo[4,5-c]quinoline

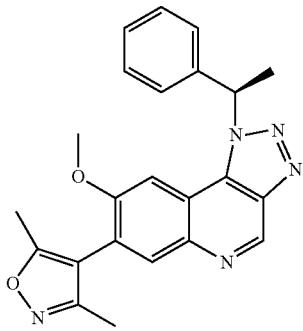 [SMILES: COc1cc2c(cc1-c1c(C)noc1C)ncc1nnn([C@H](C)c3ccccc3)c12]

To a solution of 7-(3,5-dimethyl-4-isoxazolyl)-6-(methoxy)-N$^4$-[(1R)-1-phenylethyl]-3,4-quinolinediamine (for a preparation see Intermediate 39, 0.2 g, 0.515 mmol) in DCM (10 ml) cooled at 0° C., were added AcOH (0.5 ml) and a solution of sodium nitrite (0.07 g) in water (1 ml). The mixture was stirred at room temperature overnight. The reaction mixture was treated with saturated aqueous Sodium hydrogen carbonate and extracted with DCM. The organic phase was dried over $Na_2SO_4$, evaporated under reduced pressure. The residue was purified by flash chromatography on silica gel (DCM/MeOH, 95:5). The solid was triturated in diisopropyl ether to give the title compound as a green powder (0.18 g, 87.5%).

LC-HRMS: ES$^+$ exact mass calculated for $C_{23}H_{21}N_5O_2$: 400.1773 MH$^+$. Found: 400.1785, Rt=3.04 min. (APCI-MS) m/z: 400 MH$^+$, Rt 3.15 min.

The following examples were prepared in an analogous manner to example 32:

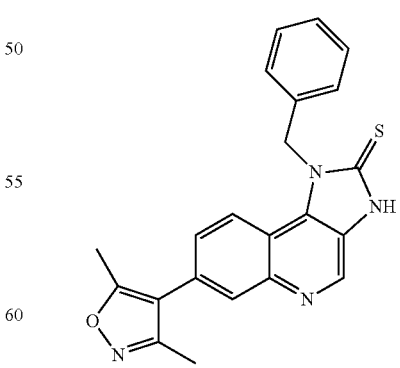

| Example | R$^1$ | Intermediate | LC-HRMS | LC/MS |
|---|---|---|---|---|
| 33 | | 30 | exact mass calculated for $C_{22}H_{19}N_5O_2$: 388.1617 MH$^+$. Found: 388.1645, Rt = 2.83 min. | m/z: 400 (M + H)$^+$, Rt = 3.04 min. |

Example 34

7-(3,5-dimethyl-4-isoxazolyl)-1-(benzyl)-1,3-dihydro-2H-imidazo[4,5-c]quinoline-2-thione A mixture of intermediate 30 (0.5 g, 1.45 mmol), CS$_2$ (1.6 ml) and triethylamine (0.3 ml) in Ethanol (10 ml) was stirred at 60° C. overnight. The reaction mixture was hydrolysed with water and extracted with CH$_2$Cl$_2$. The organic layer was dried over Na₂SO₄ and concentrated. The crude solid was purified by chromatography on silica gel eluting with CH₂Cl₂/MeOH (95/5) to give the title compound as a brown powder (0.1 g, 17.9%). $^1$H NMR (300 MHz, DMSO-d6, ppm) δ: 13.93 (s, 1H), 9.01 (s, 1H), 8.22 (d, J=8.7 Hz, 1H), 8.15 (d, J=1.7 Hz, 1H), 7.66 (dd, J=8.7, 1.7 Hz, 1H), 7.48-7.27 (m, 5H), 6.17 (s, 2H), 2.52 (s, 3H), 2.34 (s, 3H).

TOF MS ES⁺ exact Mass calculated for C₂₂H₁₈N₄OS: 387.1280 MH⁺, Found: 387.1308; Rt 2.59 min The following example was prepared in an analogous manner to example 34:

| Ex | R¹ | Intermediate | TOF-MS | $^1$H NMR (300 MHz), |
|---|---|---|---|---|
| 35 | OCF₃ (phenyl) | 33 | Exact Mass calculated for C22H15F3N4O2S: 457.0946 MH⁺, Found: 457.0914; Rt 2.59 min | DMSO-d6, δ: 13.77 (s, 1H), 8.89 (s, 1H), 8.03 (s, 1H), 7.91-7.62 (m, 5H), 7.43 (d, J = 8.7 Hz, 1H), 6.92 (d, J = 8.7 Hz, 1H), 6.17 (s, 2H), 2.37 (s, 3H), 2.19 (s, 3H). |

The following examples were prepared from the appropriate intermediate compounds by a method analogous to those described earlier:

Example 36

7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one

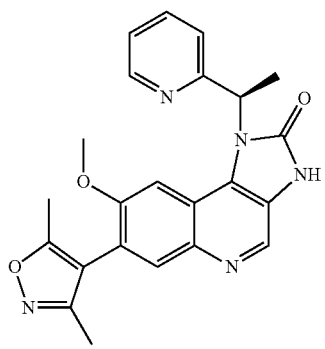

7-(3,5-Dimethyl-4-isoxazolyl)-6-(methyloxy)-4-{[(1R)-1-(2-pyridinyl)ethyl]amino}-3-quinolinecarboxamide (for a preparation see Intermediate 55, 45 g, 102 mmol) was dissolved in methanol (500 ml) and potassium hydroxide (7.47 g, 133 mmol) was added. The mixture was stirred in an ice bath, then iodobenzene diacetate (39.6 g, 123 mmol) was added in small portions over 20 min and the mixture stirred for a further 1 h. The solvent was evaporated in vacuo, the residue diluted with water (1l), and the resulting gummy suspension extracted with DCM (2×300 ml). The solvent was dried (sodium sulphate) and loaded directly onto a silica column (750 g), which was then eluted with a 2M ammonia in methanol/DCM gradient (0-10%). After evaporation of solvents in vacuo 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one (32.7 g) was obtained as a beige solid.

1H NMR CDCl₃: δH 11.02 (1H, bs), 8.80 (1H, s), 8.70 (1H, d), 7.85 (1H, s), 7.67 (1H, m), 7.36 (1H, b), 7.29-7.26 (1H, m, partially obscured by chloroform), 6.84 (1H, b), 6.52 (1H, m), 3.55 (3H, bs), 2.32 (3H, s), 2.22 (3H, d), 2.16 (3H, s).

LCMS (Method HpH): MH⁺416, Rt 0.85 min.

Example 37

7-(3,5-dimethyl-4-isoxazolyl)-8-(methyloxy)-3-[2-(methyloxy)ethyl]-1-[(1R)-1-(2-pyridinyl)ethyl]-1,3-dihydro-2H-imidazo[4,5-c]quinolin-2-one

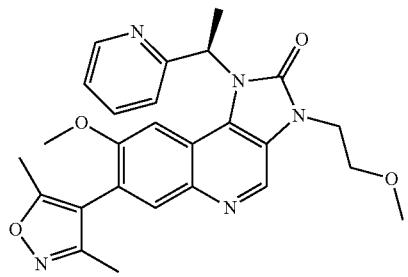 [SMILES: COCCn1c(=O)n([C@H](C)c2ccccn2)c2c3cc(OC)c(-c4c(C)noc4C)cc3ncc21]

7-(3,5-Dimethyl-4-isoxazolyl)-8-(methyloxy)-1-[(1R)-1-(2-pyridinyl)ethyl]-1,3-dihydro-2H-imidazo[4,5-c]quinolin-2-one (for a preparation see Example 36, 100 mg) in DMF (5 ml) was treated with 2-tert-butylimino-2-diethylamino-1,3-dimethylperhydro-1,3,2-diazaphosphorine, polymer bound (300 mg) and a solution of 2-bromoethyl methyl ether (40 mg) in DMF (0.5 ml). The reaction was stirred at ambient temperature, air atm for ~3 h and then left at ambient temperature overnight. The reaction was filtered and the resin washed with methanol. The solvents were evaporated under a stream of nitrogen to leave a yellow gum which was dissolved in DMSO (1 ml) and purified by MDAP (Method formate). The product fractions were combined and reduced to dryness in vacuo to give 7-(3,5-dimethyl-4-isoxazolyl)-8-(methyloxy)-3-[2-(methyloxy)ethyl]-1-[(1R)-1-(2-pyridinyl)ethyl]-1,3-dihydro-2H-imidazo[4,5-c]quinolin-2-one as a pale yellow gum (56 mg)

LCMS (Method Formate): MH⁺474, Rt 0.80 min.

Example 38

7-(3,5-dimethyl-4-isoxazolyl)-8-(methyloxy)-1-[1-(2-pyridinyl)ethyl]-1,3-dihydro-2H-imidazo[4,5-c]quinolin-2-one

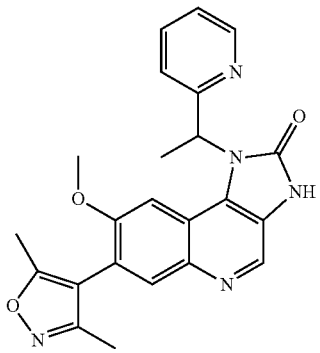 [SMILES: COc1cc2c(cc1-c1c(C)noc1C)ncc1[nH]c(=O)n(C(C)c3ccccn3)c12]

7-(3,5-Dimethyl-4-isoxazolyl)-6-(methyloxy)-4-{[1-(2-pyridinyl)ethyl]amino}-3-quinolinecarboxamide (0.39 g, 0.794 mmol) was dissolved in methanol (10 ml) and potassium hydroxide (0.089 g, 1.588 mmol) was added, the mixture was stirred in an ice-bath, bis(acetyloxy)(phenyl)-I³-iodane (0.307 g, 0.953 mmol) was added in small portions over 20 min and the mixture stirred for a further 1 h. The mixture was acidified with acetic acid (0.2 ml), evaporated in vacuo and the residue partitioned between ethyl acetate (20 ml) and water (20 ml). The solvent was dried (sodium sulphate) and evaporated and the residue dissolved in DCM (5 ml), applied to a silica cartridge (50 g), which was eluted with a methanol/ethyl acetate gradient (0-20%). Appropriate fractions were reduced to dryness in vacuo to give a beige solid. This solid was triturated with hot ethyl acetate (5 ml) and cooled and the solid collected by filtration to give 7-(3,5-dimethyl-4-isoxazolyl)-8-(methyloxy)-1-[1-(2-pyridinyl)ethyl]-1,3-dihydro-2H-imidazo[4,5-c]quinolin-2-one as pale cream powder (0.20 g).

1H NMR CDCl$_3$: δH 8.82 (1H, s), 8.70 (1H, d), 7.87 (1H, s), 7.67 (1H, m), 7.36 (1H, b), 7.29-7.26 (1H, m, partially obscured by chloroform), 6.87 (1H, b), 6.51 (1H, m), 3.56 (3H, s), 2.32 (3H, s), 2.22 (3H, d), 2.16 (3H, s).

LCMS (Method Formate): MH⁺416, Rt 0.69 min.

Example 39

7-(3,5-dimethyl-4-isoxazolyl)-8-(methyloxy)-1-[(1S)-1-(2-pyridinyl)ethyl]-1,3-dihydro-2H-imidazo[4,5-c]quinolin-2-one

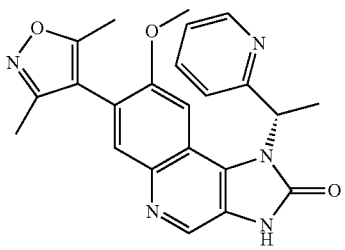 [SMILES: COc1cc2c(cc1-c1c(C)noc1C)ncc1[nH]c(=O)n([C@@H](C)c3ccccn3)c12]

7-(3,5-Dimethyl-4-isoxazolyl)-8-(methyloxy)-1-[1-(2-pyridinyl)ethyl]-1,3-dihydro-2H-imidazo[4,5-c]quinolin-2-one (for a preparation see Example 38, ~50 mg) was dissolved in 3 ml of ethanol (3 ml) and heptanes (3 ml) with warming (×3). The solutions were purified by chiral HPLC using 6× injection (3 ml) of the above solution onto a Chiralpak IA column (20 um, 5 cm×25 cm) and elution with ethanol/heptanes (30%, flow rate 50 ml/min, wavelength 215 nm). The mixed fractions were reduced to dryness in vacuo and reprocessed as described in the method above. The bulked fractions of the first eluting enantiomer were reduced to dryness in vacuo to give 7-(3,5-dimethyl-4-isoxazolyl)-8-(methyloxy)-1-[(1S)-1-(2-pyridinyl)ethyl]-1,3-dihydro-2H-imidazo[4,5-c]quinolin-2-one (61 mg).

1H NMR CDCl$_3$: δH 8.86 (1H, s), 8.68 (1H, d), 7.91 (1H, s), 7.67 (1H, m), 7.37 (1H, b), 7.29-7.26 (1H, m, partially obscured by chloroform), 6.90 (1H, b), 6.49 (1H, m), 3.58 (3H, s), 2.32 (3H, s), 2.20 (3H, d), 2.16 (3H, s).

LCMS (Method Formate): MH⁺416, Rt 0.71 min

Example 40

7-(3,5-dimethyl-4-isoxazolyl)-8-(methyloxy)-1-[1-(1-methyl-1H-pyrazol-4-yl)ethyl]-1,3-dihydro-2H-imidazo[4,5-c]quinolin-2-one

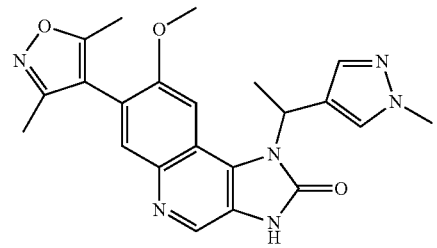 [SMILES: COc1cc2c(cc1-c1c(C)noc1C)ncc1[nH]c(=O)n(C(C)c3cnn(C)c3)c12]

7-(3,5-Dimethyl-4-isoxazolyl)-6-(methyloxy)-4-{[1-(1-methyl-1H-pyrazol-4-yl)ethyl]amino}-3-quinolinecarboxamide (110 mg, 0.262 mmol, intermediate 61) was dissolved in methanol (10 ml) and cooled to 0° C. in an ice bath, potassium hydroxide (19 mg, 0.340 mmol) was added and the solution stirred for 10 min. Iodobenzene diacetate (110 mg, 0.340 mmol) was added and the mixture stirred for a further 2 h. The solution was diluted with ethyl acetate (50 ml), washed with water, dried (sodium sulphate) and evaporated. The residue was and the residue was dissolved in DCM (4 ml), applied to a silica cartridge (25 g) and the cartridge eluted with a 2M ammonia in methanol/DCM gradient (0-10%) to give, after evaporation in vacuo of the product-containing fractions, 7-(3,5-dimethyl-4-isoxazolyl)-8-(methyloxy)-1-[1-(1-methyl-1H-pyrazol-4-yl)ethyl]-1,3-dihydro-2H-imidazo[4,5-c]quinolin-2-one as beige solid (46 mg).

LCMS (Method Formate): MH⁺ 419, Rt 0.62 min

Example 41

7-(3,5-dimethyl-4-isoxazolyl)-8-(methyloxy)-1-(2-pyridinylmethyl)-2-(tetrahydro-2H-pyran-4-yl)-1H-imidazo[4,5-c]quinoline

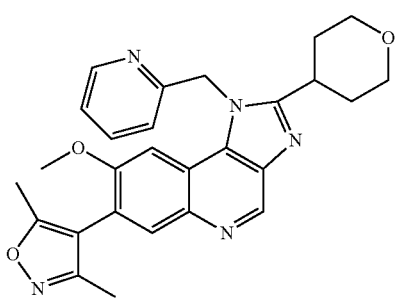 [SMILES: COc1cc2c(cc1-c1c(C)noc1C)ncc1nc(C3CCOCC3)n(Cc3ccccn3)c12]

To a solution of 4-chloro-7-(3,5-dimethyl-4-isoxazolyl)-6-(methoxy)-3-nitroquinoline (for a preparation see intermediate 18, 7 g) in acetonitrile (100 ml) was added (2-pyridinylmethyl)amine (6.8 g) and the resulting mixture was heated at 60° C. for 1 h. The reaction mixture was then hydrolysed, extracted with DCM and the combined organic phases were dried ($Na_2SO_4$), filtered and evaporated to dryness. A portion of this material (2 g) was dissolved in Ethanol (80 ml) and HCl (1 ml, conc.). Tin (II) chloride dihydrate (1 g) was then added in two portions and the reaction mixture was stirred for 2 h at room temperature. The reaction mixture was hydrolysed using a saturated solution of sodium hydrogen carbonate. The m was extracted with DCM and the combined organic layers were filtered over Celite. The filtrate was dried ($Na_2SO_4$), filtered and concentrated to dryness to give, after chromatography, 3 g of material. The latter was dissolved in DCM (100 ml) and to this mixture were added HATU (3.65 g) and tetrahydro-2H-pyran-4-carboxylic acid (1.25 g). The resulting reaction mixture was stirred overnight at room temperature and hydrolysed by adding a solution of sodium hydrogen carbonate. The reaction mixture was extracted with DCM, dried ($Na_2SO_4$), filtered and concentrated to dryness to give the crude intermediate (2.9 g). This was dissolved on acetic acid (30 ml) and the resulting mixture was heated to 90° C. for 6 h. The reaction mixture was concentrated to dryness. A saturated aqueous solution of Sodium hydrogen carbonate was added and the mixture was extracted with DCM, dried ($Na_2SO_4$), filtered and concentrated to dryness. The crude compound was purified by chromatography on silica gel, eluting with DCM/methanol (95:5), then recrystallised from ethanol and was dried under vacuum to give 7-(3,5-dimethyl-4-isoxazolyl)-8-(methyloxy)-1-(2-pyridinylmethyl)-2-(tetrahydro-2H-pyran-4-yl)-1H-imidazo[4,5-c]quinoline as a beige powder (1.88 g).

LC-HRMS: $ES^+$ exact mass calculated for $C_{27}H_{28}N_5O_3$ 470.2192 $MH^+$, found: 470.2115, Rt 2.25 min.

Example 43

4-(8-methoxy-2-(methoxymethyl)-1-(pyridin-2-ylmethyl)-1H-imidazo[4,5-c]quinolin-7-yl)-3,5-dimethylisoxazole

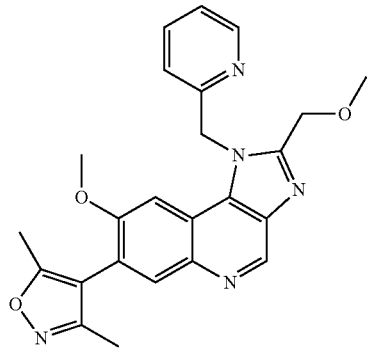 [SMILES: COCc1nc2cnc3cc(-c4c(C)noc4C)c(OC)cc3c2n1Cc1ccccn1]

7-(3,5-dimethylisoxazol-4-yl)-6-methoxy-N4-(pyridin-2-ylmethyl)quinoline-3,4-diamine (for a preparation see Intermediate 63, 500 mg) was dissolved in DCM (20 ml) and the reaction mixture was cooled to 0° C. 2-Methoxyacetyl chloride (1.1 eq) was added dropwise and the reaction mixture was stirred at room temperature for 30 min. The mixture was hydrolysed using a solution of sodium hydrogen carbonate and extracted with DCM. The organic was dried over $Na_2SO_4$, filtered and concentrated to dryness. The obtained residue was dissolved in acetic acid (5 ml) and the reaction mixture was heated to 130° C. for 16 h. The reaction mixture was treated with sodium hydroxide (1M) and extracted with DCM. The organic was dried over $Na_2SO_4$, filtered and concentrated to dryness. The residue was purified by chromatography on silica gel, eluting with DCM/methanol (95:5). The resulting compound was recrystallised from acetonitrile and dried under vacuum to give 4-(8-methoxy-2-(methoxymethyl)-1-(pyridin-2-ylmethyl)-1H-imidazo[4,5-c]quinolin-7-yl)-3,5-dimethylisoxazole (50 mg) as a cream-coloured powder.

LC-HRMS: $ES^+$ exact mass calculated for $C_{22}H_{19}N_5O_3$ 430.1879 $MH^+$, found: 430.1833, Rt 2.23 min.

Example 44

7-(3,5-dimethyl-4-isoxazolyl)-8-(methyloxy)-1-[1-(2-pyridinyl)ethyl]-2-(tetrahydro-2H-pyran-4-yl)-1H-imidazo[4,5-c]quinoline

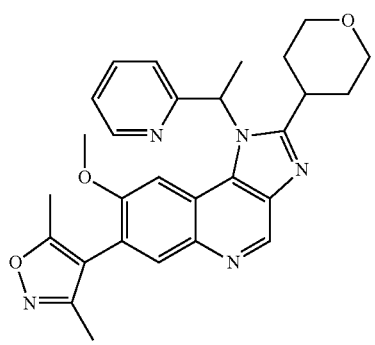 [SMILES: COc1cc2c(cc1-c1c(C)noc1C)ncc1nc(C3CCOCC3)n(C(C)c3ccccn3)c12]

To a solution of 7-(3,5-dimethyl-4-isoxazolyl)-6-(methyloxy)-$N^4$-[(1R)-1-(2-pyridinyl)ethyl]-3,4-quinolinediamine (for a preparation see Intermediate 64, 380 mg) in DCM (20 ml) was added tetrahydro-2H-pyran-4-carboxylic acid (240 mg) followed by HATU (1.2 equiv) and triethylamine (1.5 equiv). The reaction mixture was stirred at room temperature for 1 h, and then hydrolysed using a saturated solution of sodium hydrogen carbonate. The mixture was extracted with DCM and the organic was dried over $Na_2SO_4$, filtered and concentrated to dryness. The resulting crude product was diluted in acetic acid (5 ml) and heated at 100° C. overnight. The reaction mixture was then taken-up in a 1:1 mixture of sodium hydroxide (1N) and water (total 100 ml), extracted with DCM and the resulting crude product was purified by chromatography on silica gel eluting with DCM/methanol (95:5). The resulting product was taken-up in diethyl ether and dried under vacuum to give racemic 7-(3,5-dimethyl-4-isoxazolyl)-8-(methyloxy)-1-[1-(2-pyridinyl)ethyl]-2-(tetrahydro-2H-pyran-4-yl)-1H-imidazo[4,5-c]quinoline (400 mg) as a grey powder.

LC-HRMS: $ES^+$ exact mass calculated for $C_{28}H_{30}N_5O_3$ 484.2349 $MH^+$, found: 484.2382, Rt 2.30 min.

Example 45

7-(3,5-dimethyl-4-isoxazolyl)-8-(methyloxy)-1-[(1R)-1-(2-pyridinyl)ethyl]-2-(tetrahydro-2H-pyran-4-yl)-1H-imidazo[4,5-c]quinoline and Example 46

7-(3,5-dimethyl-4-isoxazolyl)-8-(methyloxy)-1-[(1S)-1-(2-pyridinyl)ethyl]-2-(tetrahydro-2H-pyran-4-yl)-1H-imidazo[4,5-c]quinoline

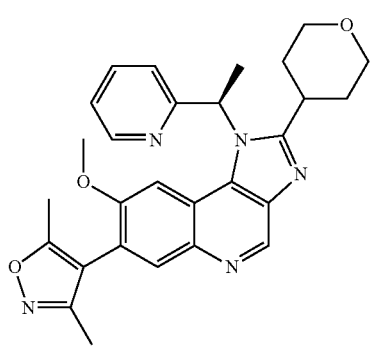

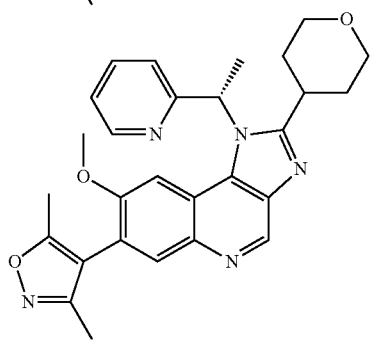

The racemic mixture of 7-(3,5-dimethyl-4-isoxazolyl)-8-(methyloxy)-1-[1-(2-pyridinyl)ethyl]-2-(tetrahydro-2H-pyran-4-yl)-1H-imidazo[4,5-c]quinoline (400 mg) was separated using a semi-preparative column: Chiracel OD, 250×20 nm. 10 µm, eluting with hexane/ethanol (85:15) [Flow rate: 18 ml/min; rt; UV detection: 254 nm; Injection volume 900 µL] to give:

Isomer 1: 7-(3,5-dimethyl-4-isoxazolyl)-8-(methyloxy)-1-[(1R*)-1-(2-pyridinyl)ethyl]-2-(tetrahydro-2H-pyran-4-yl)-1H-imidazo[4,5-c]quinoline (55 mg) as a white powder. LC-HRMS: $ES^+$ exact mass calculated for $C_{28}H_{30}N_5O_3$ 484.2349 $MH^+$, found: 484.2393, Rt 2.46 min. Analytical HPLC (Chiracel OD column, 250× 4.6 nm. 10 µm, eluting with hexane/ethanol (60/40): Rt 7.868

Isomer 2: 7-(3,5-dimethyl-4-isoxazolyl)-8-(methyloxy)-1-[(1S*)-1-(2-pyridinyl)ethyl]-2-(tetrahydro-2H-pyran-4-yl)-1H-imidazo[4,5-c]quinoline (55 mg) as a white powder. LC-HRMS $ES^+$ exact mass calculated for $C_{28}H_{30}N_5O_3$ 484.2349 $MH^+$, found: 484.2394, Rt 2.43 min. Analytical HPLC (Chiracel OD column, 250× 4.6 nm. 10 µm, eluting with hexane/ethanol (60:40): Rt 9.377

Example 47

7-(3,5-dimethyl-4-isoxazolyl)-8-(methyloxy)-1-(2-pyrimidinylmethyl)-1,3-dihydro-2H-imidazo[4,5-c]quinolin-2-one

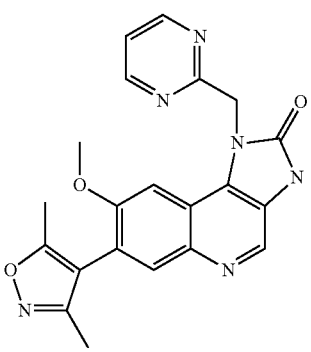 [SMILES: COc1cc2c(cc1-c1c(C)noc1C)ncc1[nH]c(=O)n(Cc3ncccn3)c12]

In a 100 ml flask a mixture of 4-chloro-7-(3,5-dimethyl-4-isoxazolyl)-6-(methyloxy)-3-quinolinecarboxamide (for a preparation see Intermediate 56, 331 mg) and (2-pyrimidinylmethyl)amine (273 mg) in acetonitrile was heated at 100° C. for 2 h. The reaction mixture was hydrolyzed with a solution of sodium hydrogen carbonate, extracted with DCM and the organic dried over $Na_2SO_4$, filtered and concentrated to dryness to give 350 mg of crude intermediate. The residue was dissolved in acetonitrile (15 ml), bis(trifluoroacetoxy) iodo]benzene (0.5 g) was added and the reaction mixture was stirred for 3 h at room temperature. The reaction mixture was washed with water, extracted with DCM and the organic dried over $Na_2SO_4$, filtered and concentrated to dryness. The resulting crude compound was purified by chromatography on silica gel eluting with DCM/methanol (95:5) and the resulting residue was recrystallised from acetonitrile and dried in vacuo to give 7-(3,5-dimethyl-4-isoxazolyl)-8-(methyloxy)-1-(2-pyrimidinylmethyl)-1,3-dihydro-2H-imidazo[4,5-c] quinolin-2-one (70 mg) as a beige powder.

LC-HRMS: $ES^+$ exact mass calculated for $C_{21}H_{19}N_6O_3$ 403.1519 $MH^+$, found: 403.1516, Rt 2.04 min.

Example 48

7-(3,5-dimethyl-4-isoxazolyl)-8-(methyloxy)-1-(2-pyrazinylmethyl)-1,3-dihydro-2H-imidazo[4,5-c]quinolin-2-one

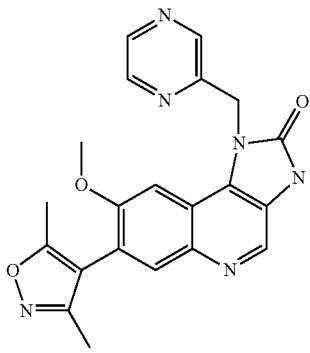 [SMILES: COc1cc2c(cc1-c1c(C)noc1C)ncc1[nH]c(=O)n(Cc3cnccn3)c12]

In a 100 ml flask a mixture of 4-chloro-7-(3,5-dimethyl-4-isoxazolyl)-6-(methyloxy)-3-quinolinecarboxamide (for a preparation see Intermediate 56, 331 mg,) and (2-pyrazinylmethyl)amine (2.5 eq) in acetonitrile was heated at 100° C. for 2 h. The reaction mixture was hydrolyzed with a solution of sodium hydrogen carbonate, extracted with DCM and the organic dried over $Na_2SO_4$, filtered and concentrated to dryness to give the crude intermediate. The residue was dissolved in acetonitrile (15 ml), bis(trifluoroacetoxy)iodo]benzene (0.5 g) was added and the reaction mixture was stirred for 3 h at room temperature. The reaction mixture was washed with water, extracted with DCM and the organic were dried over $Na_2SO_4$, filtered and concentrated to dryness. The resulting crude compound was purified by chromatography on silica gel eluting with DCM/methanol (95:5) and the resulting residue was recrystallised from acetonitrile and dried in vacuo to give 7-(3,5-dimethyl-4-isoxazolyl)-8-(methyloxy)-1-(2-pyrimidinylmethyl)-1,3-dihydro-2H-imidazo[4,5-c]quinolin-2-one (100 mg) as a beige powder.

LC-HRMS: ES+ exact mass calculated for $C_{21}H_{19}N_6O_3$ 403.1519 MH$^+$, found: 403.1550, Rt 2.06 min.

Example 49

7-(3,5-dimethyl-4-isoxazolyl)-8-(methyloxy)-1-(3-pyridinylmethyl)-1,3-dihydro-2H-imidazo[4,5-c]quinolin-2-one

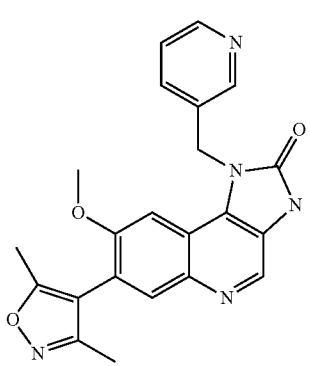 [SMILES: COc1cc2c(cc1-c1c(C)noc1C)ncc1[nH]c(=O)n(Cc3cccnc3)c12]

A solution of 4-chloro-7-(3,5-dimethyl-4-isoxazolyl)-6-(methyloxy)-3-quinolinecarboxamide (for a preparation see intermediate 56, 332 mg,) and (3-pyridinylmethyl)amine (2.5 equiv in acetonitrile was heated for 4 h. The reaction mixture was then concentrated to dryness and hydrolyzed with water. The mixture extracted with DCM and the organic was dried over $Na_2SO_4$, filtered and concentrated to dryness to give the crude intermediate. The residue was partially dissolved in acetonitrile (30 ml) and bis(trifluoroacetoxy)iodo]benzene (800 mg) was added. The resulting mixture was stirred at room temperature for 24 h. The reaction mixture was then concentrated to dryness and hydrolysed with water. The mixture was extracted with DCM and the organic dried over $Na_2SO_4$, filtered and concentrated to dryness. The residue was purified by chromatography on silica gel, eluting with DCM/methanol (95/5). The purified residue was taken-up in diethyl ether to give 7-(3,5-dimethyl-4-isoxazolyl)-8-(methyloxy)-1-(3-pyridinyl methyl)-1,3-dihydro-2H-imidazo[4,5-c]quinolin-2-one (70 mg) as a brown powder.

LC-HRMS: ES$^+$ exact mass calculated for $C_{22}H_{20}N_5O_3$ 402.1566 MH$^+$, found: 402.1576, Rt 1.96 min.

Example 50

7-(3,5-dimethyl-4-isoxazolyl)-1-[(2,4-dimethyl-1,3-thiazol-5-yl)methyl]-8-(methyloxy)-1,3-dihydro-2H-imidazo[4,5-c]quinolin-2-one

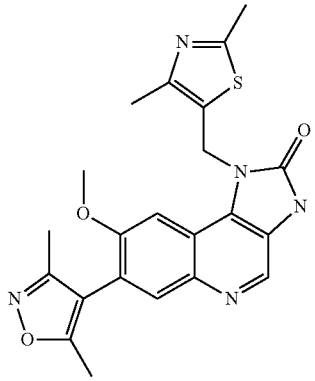 [SMILES: COc1cc2c(cc1-c1c(C)noc1C)ncc1[nH]c(=O)n(Cc3sc(C)nc3C)c12]

To a solution of 7-(3,5-dimethyl-4-isoxazolyl)-4-{[(2,4-dimethyl-1,3-thiazol-5-yl)methyl]amino}-6-(methyloxy)-3-quinolinecarboxamide (for a preparation see intermediate 65, 0.3 g) in acetonitrile (50 ml) was added bis(trifluoroacetoxy) iodo]benzene (0.443 g) and the reaction mixture was stirred at room temperature overnight. The reaction mixture was then poured into water and extracted with DCM. The organic phase was dried over $Na_2SO_4$ and concentrated to dryness to give an orange oil. The residue was purified by flash chromatography on silica gel eluting with DCM/methanol (98: 2 then 97:3) give a sticky pale yellow solid, which was triturated in hot diisopropylether to give 7-(3,5-dimethyl-4-isoxazolyl)-1-[(2,4-dimethyl-1,3-thiazol-5-yl)methyl]-8-(methyloxy)-1,3-dihydro-2H-imidazo[4,5-c]quinolin-2-one (0.21 g) as a cream coloured solid.

LC/MS: MH$^+$ 436.06, [M–H]$^-$ 434.12

Example 51

7-(3,5-dimethyl-4-isoxazolyl)-8-(methyloxy)-2-[(methyloxy)methyl]-1-[1-(2-pyridinyl)ethyl]-1H-imidazo[4,5-c]quinoline

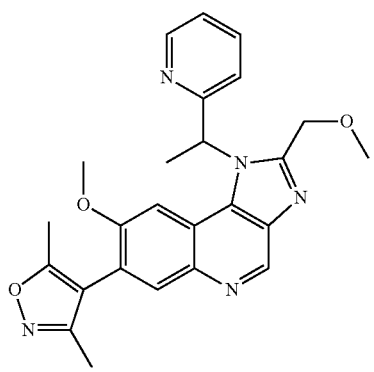 [SMILES: COCc1nc2cnc3cc(-c4c(C)noc4C)c(OC)cc3c2n1C(C)c1ccccn1]

To a solution of 7-(3,5-dimethyl-4-isoxazolyl)-6-(methyloxy)-N⁴-[1-(2-pyridinyl)ethyl]-3,4-quinolinediamine (for a preparation see Intermediate 65, 250 mg) in DCM (20 ml) was added (methyloxy)acetic acid (116 mg) followed by HATU (1.2 equiv) and triethylamine (1.5 equiv). The reaction mixture was stirred at room temperature for 1 h, and was then hydrolysed using a saturated solution of sodium hydrogen carbonate. The mixture was extracted with DCM and the organic dried over Na₂SO₄, filtered and concentrated to dryness. The resulting product was dissolved in ethanol (60 ml) and a solution of sodium hydroxide (1N, 15 ml) was added. The reaction mixture was heated to 90° C. for 16 h and was then allowed to cool to room temperature. DCM (150 ml) and water (100 ml) were added. The phases were separated and the organic phase was dried over Na₂SO₄, filtered and evaporated to dryness. The residue was purified by silica gel chromatography eluting with DCM/methanol (95:5). The resulting residue was taken-up in acetonitrile, washed with diethyl ether and dried in vacuo to give 7-(3,5-dimethyl-4-isoxazolyl)-8-(methyloxy)-2-[(methyloxy)methyl]-1-[1-(2-pyridinyl)ethyl]-1H-imidazo[4,5-c]quinoline (90 mg) as a beige powder.

LC-HRMS: ES⁺ exact mass calculated for $C_{28}H_{30}N_5O_3$ 444.2036 MH⁺, found: 444.2072, Rt 2.39 min.

Example 52

7-(3,5-dimethyl-4-isoxazolyl)-1-[(5-methyl-3-isoxazolyl)methyl]-8-(methyloxy)-1,3-dihydro-2H-imidazo[4,5-c]quinolin-2-one

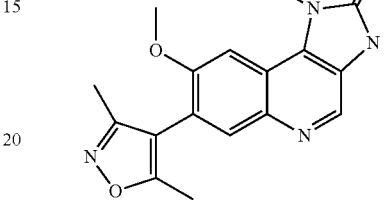

7-(3,5-Dimethyl-4-isoxazolyl)-4-{[(5-methyl-3-isoxazolyl)methyl]amino}-6-(methyloxy)-3-quinolinecarboxamide (for a preparation see Intermediate 67, 280 mg) was partially dissolved in acetonitrile (30 ml) and bis(trifluoroacetoxy)iodo]benzene (800 mg) was added. The reaction mixture was stirred at 50° C. for 12 h and was then concentrated to dryness. The crude was taken-up in water and extracted with DCM. The organic was dried over Na₂SO₄, filtered and evaporated to dryness. The residue was purified by silica gel chromatography eluting with DCM/methanol (95:5), and the obtained product was subsequently taken-up in diethyl ether to give 7-(3,5-dimethyl-4-isoxazolyl)-1-[(5-methyl-3-isoxazolyl)methyl]-8-(methyloxy)-1,3-dihydro-2H-imidazo[4,5-c]quinolin-2-one (200 mg). LC/MS: Rt 2.52 min.

Example 53

7-(3,5-dimethyl-4-isoxazolyl)-8-(methyloxy)-1-(2-thienylmethyl)-1,3-dihydro-2H-imidazo[4,5-c]quinolin-2-one

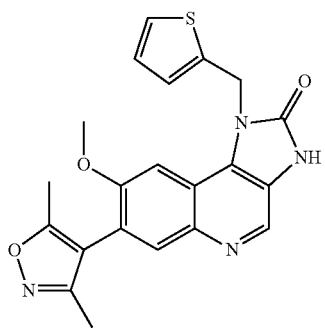 [SMILES: COc1cc2c(cc1-c1c(C)noc1C)ncc1[nH]c(=O)n(Cc3cccs3)c12]

To a magnetically stirred solution of 7-(3,5-dimethyl-4-isoxazolyl)-6-(methyloxy)-N⁴-(2-thienylmethyl)-3,4-quinolinediamine (for a preparation see intermediate 68, 1.5 g,) in acetonitrile (50 ml) in a 250 ml flask equipped with a reflux condenser was added bis(trifluoroacetoxy)iodo]benzene (2.37 g). The reaction mixture was stirred at 20° C. for 2 h then heated at 50° C. for 1 h. Water was added to the reaction and the mixture extracted with DCM. The organic phase was dried over $Na_2SO_4$, filtered and concentrated to dryness. The residue was purified by chromatography on silica gel (25 g, BP-SUP silica) eluting with DCM and then DCM/methanol (95:5). The resulting residue was triturated in hot isopropyl ether, filtered and dried to give 7-(3,5-dimethyl-4-isoxazolyl)-8-(methyloxy)-1-(2-thienylmethyl)-1,3-dihydro-2H-imidazo[4,5-c]quinolin-2-one in 2 batches (1.114 g total) as a brown powder.

LC-HRMS: $ES^+$ exact mass calculated for $C_{21}H_{18}N_4O_3S$ 407.1178 $MH^+$, found: 407.1215; Rt 2.38 min.

Example 54

7-(3,5-dimethyl-4-isoxazolyl)-1-[(2,4-dimethyl-1,3-thiazol-5-yl)methyl]-8-(methyloxy)-2-(tetrahydro-2H-pyran-4-yl)-1H-imidazo[4,5-c]quinoline

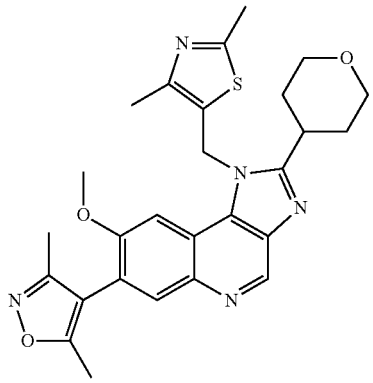 [SMILES: COc1cc2c(cc1-c1c(C)noc1C)ncc1nc(C3CCOCC3)n(Cc3sc(C)nc3C)c12]

A solution of N-[7-(3,5-dimethyl-4-isoxazolyl)-4-{[(2,4-dimethyl-1,3-thiazol-5-yl)methyl]amino}-6-(methyloxy)-3-quinolinyl]tetrahydro-2H-pyran-4-carboxamide (for a preparation see Intermediate 71, 0.37 g) in acetic acid was stirred for 2 h at 100° C. The reaction mixture was then evaporated to dryness and the residue was then taken-up in a saturated solution of sodium hydrogen carbonate. The mixture was extracted with DCM and the organic phase dried over $Na_2SO_4$ and evaporated to dryness. The residue was purified by flash chromatography on silica gel, eluting with DCM/methanol ((8:2 then 94:6) to give a sticky beige solid (0.3 g). The latter was triturated with hot diisopropylether to give 7-(3,5-dimethyl-4-isoxazolyl)-1-[(2,4-dimethyl-1,3-thiazol-5-yl)methyl]-8-(methyloxy)-2-(tetrahydro-2H-pyran-4-yl)-1H-imidazo[4,5-c]quinoline (0.22 g) as a white solid.

LC-HRMS: $ES^+$ exact mass calculated for $C_{27}H_{30}N_5O_3S_1$ 504.2069 $MH^+$, found: 504.2021.

Example 55

7-(3,5-dimethyl-4-isoxazolyl)-1-[(5-methyl-2-furanyl)methyl]-8-(methyloxy)-1,3-dihydro-2H-imidazo[4,5-c]quinolin-2-one

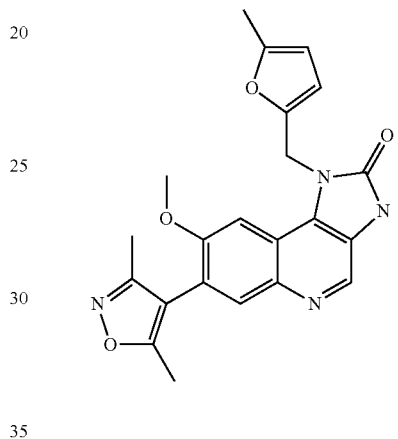

A mixture of 7-(3,5-dimethyl-4-isoxazolyl)-4-{[(5-methyl-2-furanyl)methyl]amino}-6-(methyloxy)-3-quinolinecarboxamide (for a preparation see Intermediate 72, 177 mg) and bis(trifluoroacetoxy)iodo]benzene (375 mg) in acetonitrile (10 ml) was stirred overnight at room temperature. The reaction mixture was evaporated to dryness, the residue was taken-up in water and extracted with DCM. The organic was dried over $Na_2SO_4$, filtered and evaporated to give 7-(3,5-dimethyl-4-isoxazolyl)-1-[(5-methyl-2-furanyl)methyl]-8-(methyloxy)-1,3-dihydro-2H-imidazo[4,5-c]quinolin-2-one (10 mg) as a beige powder. LC-HRMS: $ES^+$ exact mass calculated for $C_{22}H_{21}N_4O_4$ 405.1563 $MH^+$, found: 405.1626; Rt 2.39

| Example | Structure | Name |
|---------|-----------|------|
| 56 | ![structure] | 3-[7-(3,5-dimethyl-4-isoxazolyl)-8-(methyloxy)-2-oxo-1-(2-thienylmethyl)-1,2-dihydro-3H-imidazo[4,5-c]quinolin-3-yl]propanenitrile |

-continued

| Example | Structure | Name |
|---|---|---|
| 57 | 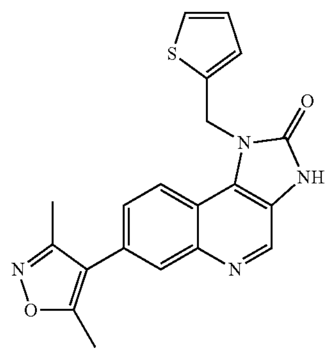 [SMILES: Cc1noc(C)c1-c1ccc2c(c1)ncc1[nH]c(=O)n(Cc3cccs3)c12] | 7-(3,5-dimethyl-4-isoxazolyl)-1-(2-thienylmethyl)-1,3-dihydro-2H-imidazo[4,5-c]quinolin-2-one |
| 58 | 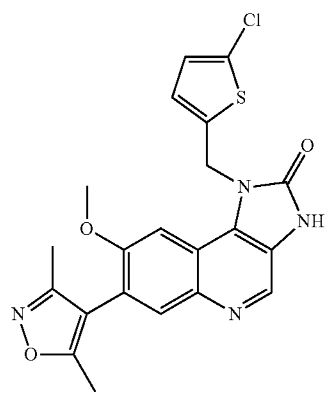 [SMILES: COc1cc2c(cc1-c1c(C)noc1C)ncc1[nH]c(=O)n(Cc3ccc(Cl)s3)c12] | 1-[(5-chloro-2-thienyl)methyl]-7-(3,5-dimethyl-4-isoxazolyl)-8-(methyloxy)-1,3-dihydro-2H-imidazo[4,5-c]quinolin-2-one |
| 59 | 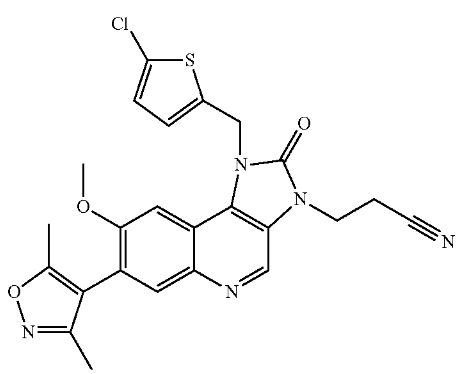 [SMILES: COc1cc2c(cc1-c1c(C)noc1C)ncc1c2n(Cc2ccc(Cl)s2)c(=O)n1CCC#N] | 3-[1-[(5-chloro-2-thienyl)methyl]-7-(3,5-dimethyl-4-isoxazolyl)-8-(methyloxy)-2-oxo-dihydro-3H-imidazo[4,5-c]quinolin-3-yl]propanenitrile |
| 60 | 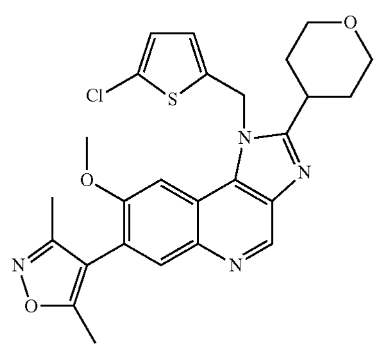 [SMILES: COc1cc2c(cc1-c1c(C)noc1C)ncc1nc(C3CCOCC3)n(Cc3ccc(Cl)s3)c12] | 1-[(5-chloro-2-thienyl)methyl]-7-(3,5-dimethyl-4-isoxazolyl)-8-(methyloxy)-2-(tetrahydro-2H-pyran-4-yl)-1H-imidazo[4,5-c]quinoline |

-continued

| Example | Structure | Name |
|---|---|---|
| 61 | 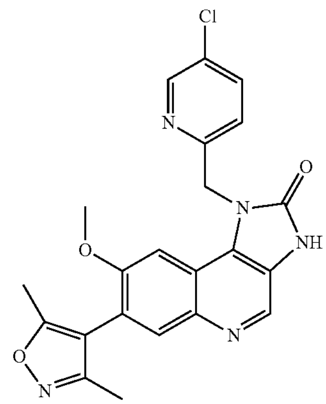 [SMILES: COc1cc2c(cc1-c1c(C)noc1C)ncc1[nH]c(=O)n(Cc3ccc(Cl)cn3)c12] | 1-[(5-chloro-2-pyridinyl)methyl]-7-(3,5-dimethyl-4-isoxazolyl)-8-(methyloxy)-1,3-dihydro-2H-imidazo[4,5-c]quinolin-2-one |
| 62 | 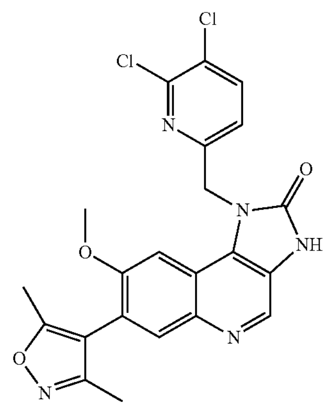 [SMILES: COc1cc2c(cc1-c1c(C)noc1C)ncc1[nH]c(=O)n(Cc3ccc(Cl)c(Cl)n3)c12] | 1-[(5,6-dichloro-2-pyridinyl)methyl]-7-(3,5-dimethyl-4-isoxazolyl)-8-(methyloxy)-1,3-dihydro-2H-imidazo[4,5-c]quinolin-2-one |
| 63 | 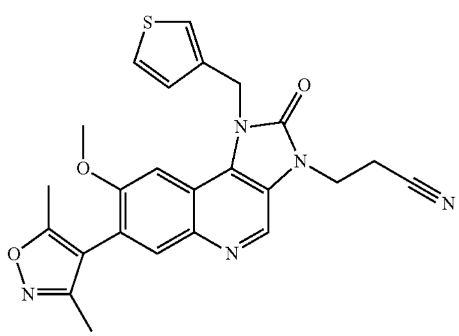 [SMILES: COc1cc2c(cc1-c1c(C)noc1C)ncc1c2n(Cc2ccsc2)c(=O)n1CCC#N] | 3-[7-(3,5-dimethyl-4-isoxazolyl)-8-(methyloxy)-2-oxo-1-(3-thienylmethyl)-1,2-dihydro-3H-imidazo[4,5-c]quinolin-3-yl]propanenitrile |
| 64 | 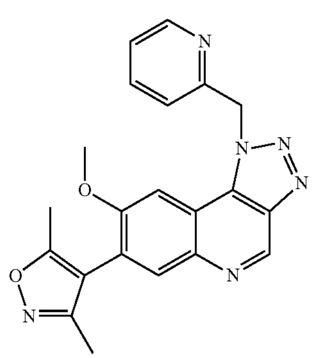 [SMILES: COc1cc2c(cc1-c1c(C)noc1C)ncc1nnn(Cc3ccccn3)c12] | 7-(3,5-dimethyl-4-isoxazolyl)-8-(methyloxy)-1-(2-pyridinylmethyl)-1H-[1,2,3]triazolo[4,5-c]quinoline |

-continued

| Example | Structure | Name |
|---|---|---|
| 65 | 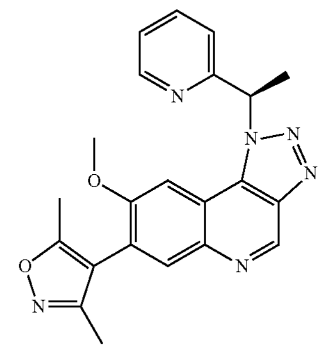 [SMILES: COc1cc2c(cc1-c1c(C)noc1C)ncc1nnn([C@H](C)c3ccccn3)c12] | 7-(3,5-dimethyl-4-isoxazolyl)-8-(methyloxy)-1-[(1R)-1-(2-pyridinyl)ethyl]-1H-[1,2,3]triazolo[4,5-c]quinoline |
| 66 | 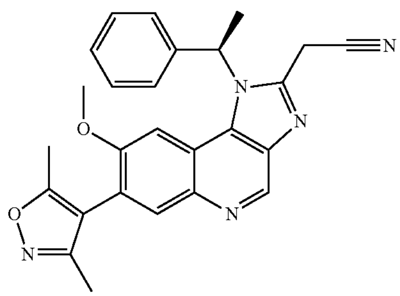 [SMILES: COc1cc2c(cc1-c1c(C)noc1C)ncc1nc(CC#N)n([C@H](C)c3ccccc3)c12] | {7-(3,5-dimethyl-4-isoxazolyl)-8-(methyloxy)-1-[(1R)-1-phenylethyl]-1H-imidazo[4,5-c]quinolin-2-yl}acetonitrile |
| 67 | 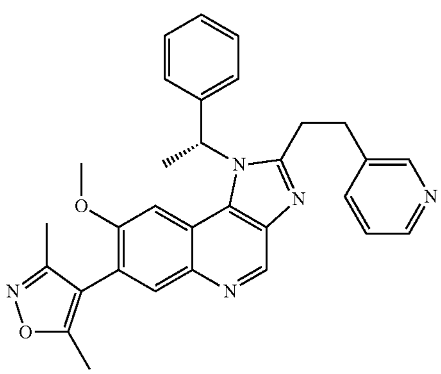 [SMILES: COc1cc2c(cc1-c1c(C)noc1C)ncc1nc(CCc3cccnc3)n([C@H](C)c3ccccc3)c12] | 7-(3,5-dimethyl-4-isoxazolyl)-8-(methyloxy)-1-[(1R)-1-phenylethyl]-2-[2-(3-pyridinyl)ethyl]-1H-imidazo[4,5-c]quinoline |
| 68 | 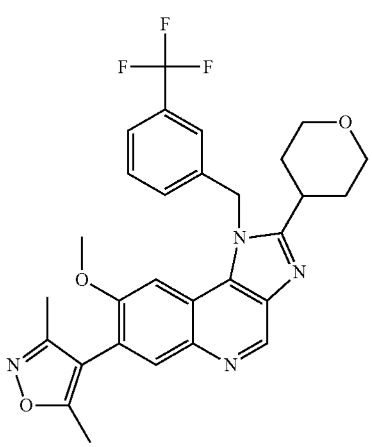 [SMILES: COc1cc2c(cc1-c1c(C)noc1C)ncc1nc(C3CCOCC3)n(Cc3cccc(C(F)(F)F)c3)c12] | 7-(3,5-dimethyl-4-isoxazolyl)-8-(methyloxy)-2-(tetrahydro-2H-pyran-4-yl)-1-{[3-(trifluoromethyl)phenyl]methyl}-1H-imidazo[4,5-c]quinoline |

-continued

| Example | Structure | Name |
|---|---|---|
| 69 | 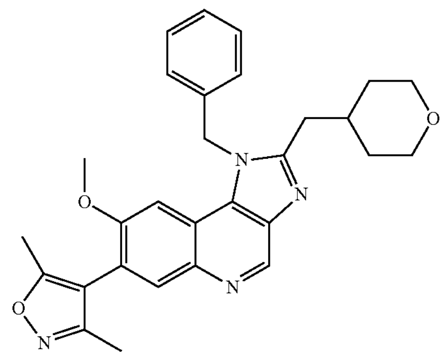 [SMILES: COc1cc2c(cc1-c1c(C)noc1C)ncc1nc(CC3CCOCC3)n(Cc3ccccc3)c12] | 7-(3,5-dimethyl-4-isoxazolyl)-8-(methyloxy)-1-(phenylmethyl)-2-(tetrahydro-2H-pyran-4-ylmethyl)-1H-imidazo[4,5-c]quinoline |
| 70 | 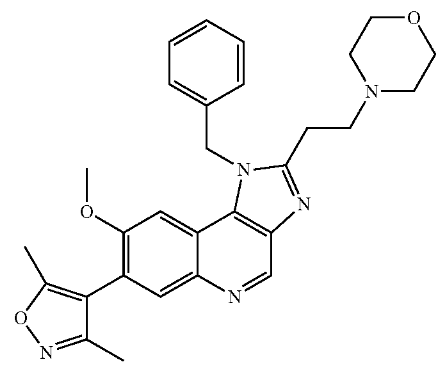 [SMILES: COc1cc2c(cc1-c1c(C)noc1C)ncc1nc(CCN3CCOCC3)n(Cc3ccccc3)c12] | 7-(3,5-dimethyl-4-isoxazolyl)-8-(methyloxy)-2-[2-(4-morpholinyl)ethyl]-1-(phenylmethyl)-1H-imidazo[4,5-c]quinoline |
| 71 | 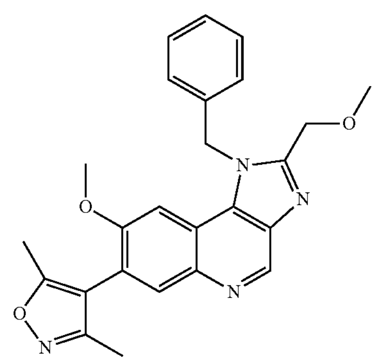 [SMILES: COCc1nc2cnc3cc(-c4c(C)noc4C)c(OC)cc3c2n1Cc1ccccc1] | 7-(3,5-dimethyl-4-isoxazolyl)-8-(methyloxy)-2-[(methyloxy)methyl]-1-(phenylmethyl)-1H-imidazo[4,5-c]quinoline |
| 72 | 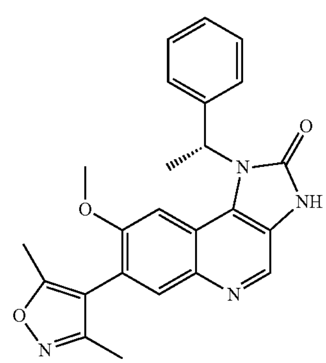 [SMILES: COc1cc2c(cc1-c1c(C)noc1C)ncc1[nH]c(=O)n([C@H](C)c3ccccc3)c12] | 7-(3,5-dimethyl-4-isoxazolyl)-8-(methyloxy)-1-[(1R)-1-phenylethyl]-1,3-dihydro-2H-imidazo[4,5-c]quinolin-2-one |

-continued

| Example | Structure | Name |
|---|---|---|
| 73 | 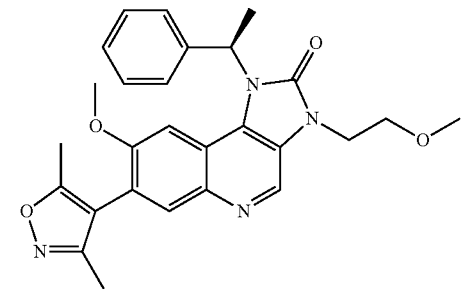 [SMILES: COCCn1c(=O)n([C@H](C)c2ccccc2)c2c3cc(OC)c(-c4c(C)noc4C)cc3ncc21] | 7-(3,5-dimethyl-4-isoxazolyl)-8-(methyloxy)-3-[2-(methyloxy)ethyl]-1-[(1R)-1-phenylethyl]-1,3-dihydro-2H-imidazo[4,5-c]quinolin-2-one |
| 74 | 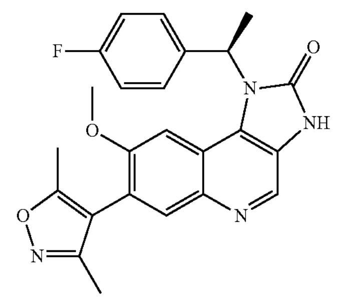 [SMILES: COc1cc2c(cc1-c1c(C)noc1C)ncc1[nH]c(=O)n([C@H](C)c3ccc(F)cc3)c12] | 7-(3,5-dimethyl-4-isoxazolyl)-1-[(1R)-1-(4-fluorophenyl)ethyl]-8-(methyloxy)-1,3-dihydro-2H-imidazo[4,5-c]quinolin-2-one |
| 75 | 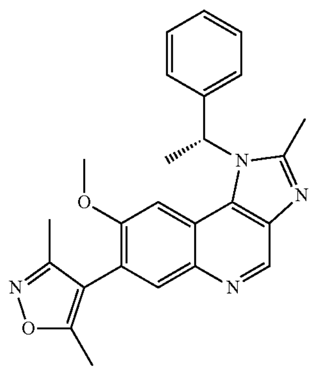 [SMILES: COc1cc2c(cc1-c1c(C)noc1C)ncc1nc(C)n([C@H](C)c3ccccc3)c12] | 7-(3,5-dimethyl-4-isoxazolyl)-2-methyl-8-(methyloxy)-1-[(1R)-1-phenylethyl]-1H-imidazo[4,5-c]quinoline |
| 76 | 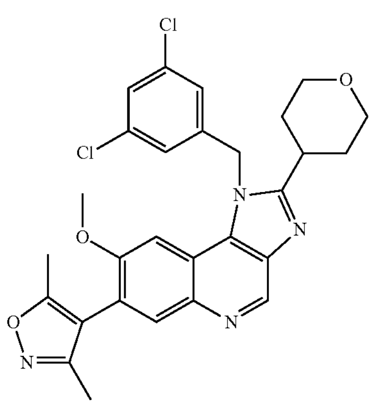 [SMILES: COc1cc2c(cc1-c1c(C)noc1C)ncc1nc(C3CCOCC3)n(Cc3cc(Cl)cc(Cl)c3)c12] | 1-[(3,5-dichlorophenyl)methyl]-7-(3,5-dimethyl-4-isoxazolyl)-8-(methyloxy)-2-(tetrahydro-2H-pyran-4-yl)-1H-imidazo[4,5-c]quinoline |

-continued

| Example | Structure | Name |
|---|---|---|
| 77 | 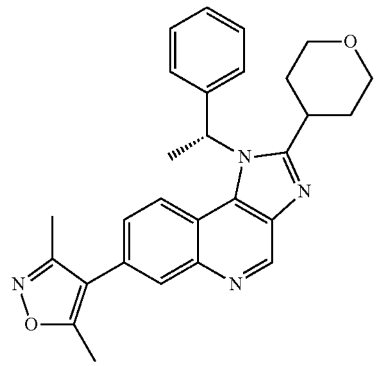 [SMILES: Cc1noc(C)c1-c1ccc2c(c1)ncc1nc(C3CCOCC3)n([C@H](C)c3ccccc3)c12] | 7-(3,5-dimethyl-4-isoxazolyl)-1-[(1R)-1-phenylethyl]-2-(tetrahydro-2H-pyran-4-yl)-1H-imidazo[4,5-c]quinoline |
| 78 | 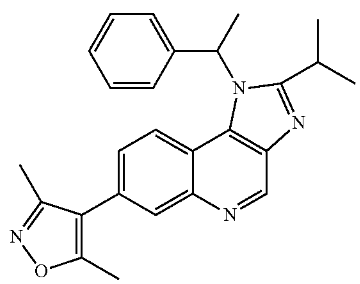 [SMILES: Cc1noc(C)c1-c1ccc2c(c1)ncc1nc(C(C)C)n(C(C)c3ccccc3)c12] | 7-(3,5-dimethyl-4-isoxazolyl)-2-(1-methylethyl)-1-(1-phenylethyl)-1H-imidazo[4,5-c]quinoline |
| 79 | 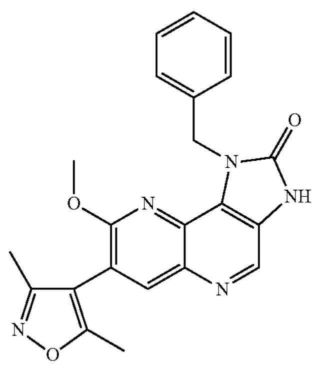 [SMILES: COc1nc2c(cc1-c1c(C)noc1C)ncc1[nH]c(=O)n(Cc3ccccc3)c12] | 7-(3,5-dimethyl-4-isoxazolyl)-8-(methyloxy)-1-(phenylmethyl)-1,3-dihydro-2H-imidazo[4,5-c]-1,5-naphthyridin-2-one |
| 80 | 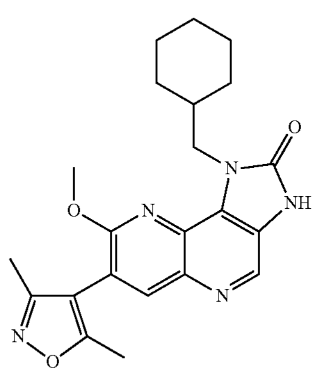 [SMILES: COc1nc2c(cc1-c1c(C)noc1C)ncc1[nH]c(=O)n(CC3CCCCC3)c12] | 1-(cyclohexylmethyl)-7-(3,5-dimethyl-4-isoxazolyl)-8-(methyloxy)-1,3-dihydro-2H-imidazo[4,5-c]-1,5-naphthyridin-2-one |

-continued

| Example | Structure | Name |
|---|---|---|
| 81 | 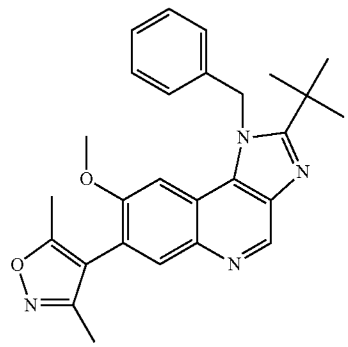 [SMILES: COc1cc2c(cc1-c1c(C)noc1C)ncc1nc(C(C)(C)C)n(Cc3ccccc3)c12] | 2-(1,1-dimethylethyl)-7-(3,5-dimethyl-4-isoxazolyl)-8-(methyloxy)-1-(phenylmethyl)-1H-imidazo[4,5-c]quinoline |
| 82 | 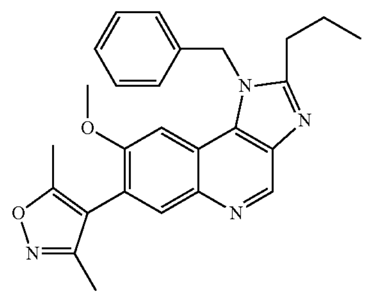 [SMILES: CCCc1nc2cnc3cc(-c4c(C)noc4C)c(OC)cc3c2n1Cc1ccccc1] | 7-(3,5-dimethyl-4-isoxazolyl)-8-(methyloxy)-1-(phenylmethyl)-2-propyl-1H-imidazo[4,5-c]quinoline |
| 83 | 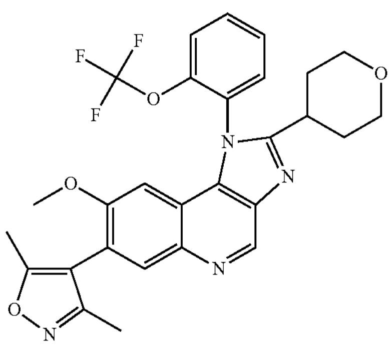 [SMILES: COc1cc2c(cc1-c1c(C)noc1C)ncc1nc(C3CCOCC3)n(-c3ccccc3OC(F)(F)F)c12] | 7-(3,5-dimethyl-4-isoxazolyl)-8-(methyloxy)-2-(tetrahydro-2H-pyran-4-yl)-1-{2-[(trifluoromethyl)oxy]phenyl}-1H-imidazo[4,5-c]quinoline |
| 84 | 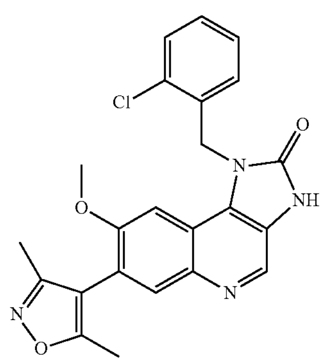 [SMILES: COc1cc2c(cc1-c1c(C)noc1C)ncc1[nH]c(=O)n(Cc3ccccc3Cl)c12] | 1-[(2-chlorophenyl)methyl]-7-(3,5-dimethyl-4-isoxazolyl)-8-(methyloxy)-1,3-dihydro-2H-imidazo[4,5-c]quinolin-2-one |

-continued

| Example | Structure | Name |
|---|---|---|
| 85 | 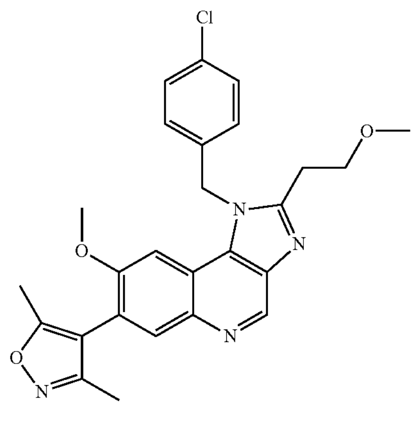 [SMILES: COCCc1nc2cnc3cc(-c4c(C)noc4C)c(OC)cc3c2n1Cc1ccc(Cl)cc1] | 1-[(4-chlorophenyl)methyl]-7-(3,5-dimethyl-4-isoxazolyl)-8-(methyloxy)-2-[2-(methyloxy)ethyl]-1H-imidazo[4,5-c]quinoline |
| 86 | 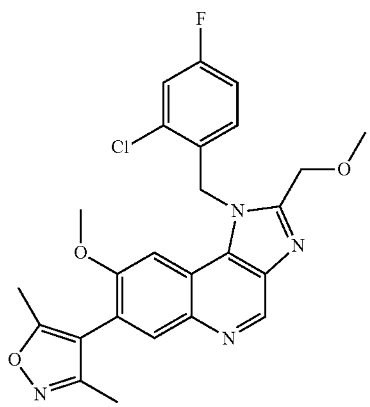 [SMILES: COCc1nc2cnc3cc(-c4c(C)noc4C)c(OC)cc3c2n1Cc1ccc(F)cc1Cl] | 1-[(2-chloro-4-fluorophenyl)methyl]-7-(3,5-dimethyl-4-isoxazolyl)-8-(methyloxy)-2-[(methyloxy)methyl]-1H-imidazo[4,5-c]quinoline |
| 87 | 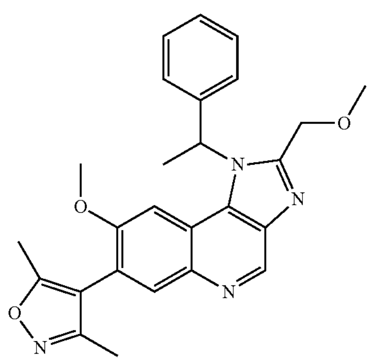 [SMILES: COCc1nc2cnc3cc(-c4c(C)noc4C)c(OC)cc3c2n1C(C)c1ccccc1] | 7-(3,5-dimethyl-4-isoxazolyl)-8-(methyloxy)-2-[(methyloxy)methyl]-1-(1-phenylethyl)-1H-imidazo[4,5-c]quinoline |
| 88 | 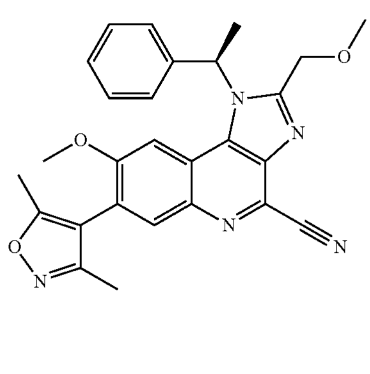 [SMILES: COCc1nc2c(C#N)nc3cc(-c4c(C)noc4C)c(OC)cc3c2n1[C@H](C)c1ccccc1] | 7-(3,5-dimethyl-4-isoxazolyl)-8-(methyloxy)-2-[(methyloxy)methyl]-1-[(1R)-1-phenylethyl]-1H-imidazo[4,5-c]quinoline-4-carbonitrile |

-continued

| Example | Structure | Name |
|---|---|---|
| 89 | 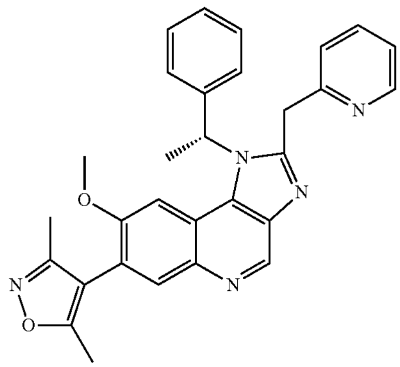 [SMILES: COc1cc2c(cc1-c1c(C)noc1C)ncc1nc(Cc3ccccn3)n([C@H](C)c3ccccc3)c12] | 7-(3,5-dimethyl-4-isoxazolyl)-8-(methyloxy)-1-[(1R)-1-phenylethyl]-2-(2-pyridinylmethyl)-1H-imidazo[4,5-c]quinoline |
| 90 | 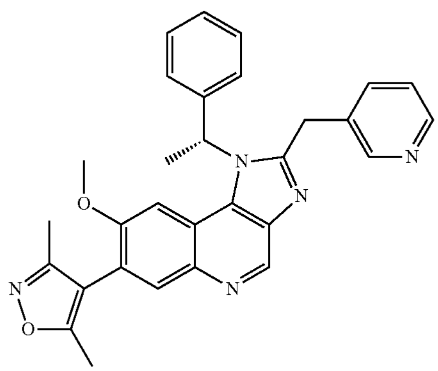 [SMILES: COc1cc2c(cc1-c1c(C)noc1C)ncc1nc(Cc3cccnc3)n([C@H](C)c3ccccc3)c12] | 7-(3,5-dimethyl-4-isoxazolyl)-8-(methyloxy)-1-[(1R)-1-phenylethyl]-2-(3-pyridinylmethyl)-1H-imidazo[4,5-c]quinoline |
| 91 | 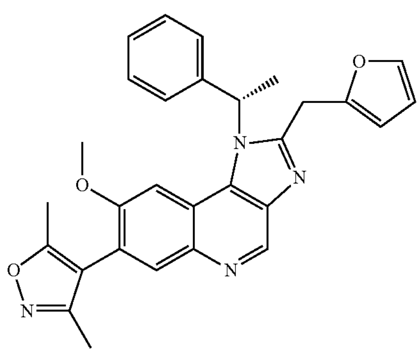 [SMILES: COc1cc2c(cc1-c1c(C)noc1C)ncc1nc(Cc3ccco3)n([C@@H](C)c3ccccc3)c12] | 7-(3,5-dimethyl-4-isoxazolyl)-2-(2-furanylmethyl)-8-(methyloxy)-1-[(1S)-1-phenylethyl]-1H-imidazo[4,5-c]quinoline |
| 92 | 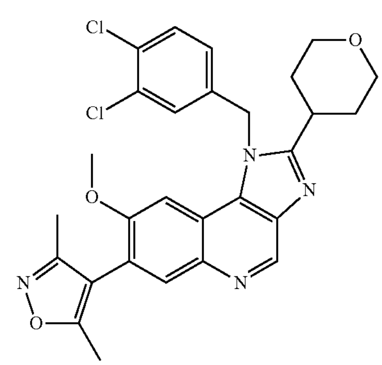 [SMILES: COc1cc2c(cc1-c1c(C)noc1C)ncc1nc(C3CCOCC3)n(Cc3ccc(Cl)c(Cl)c3)c12] | 1-[(3,4-dichlorophenyl)methyl]-7-(3,5-dimethyl-4-isoxazolyl)-8-(methyloxy)-2-(tetrahydro-2H-pyran-4-yl)-1H-imidazo[4,5-c]quinoline |

-continued

| Example | Structure | Name |
|---|---|---|
| 93 | 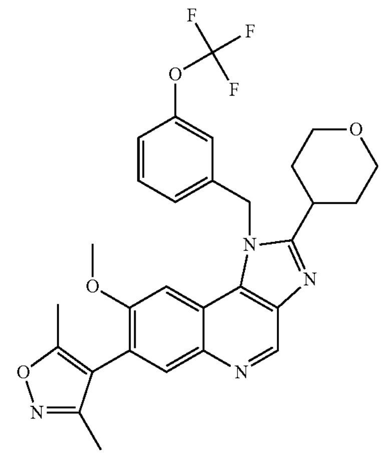 [SMILES: COc1cc2c(cc1-c1c(C)noc1C)ncc1nc(C3CCOCC3)n(Cc3cccc(OC(F)(F)F)c3)c12] | 7-(3,5-dimethyl-4-isoxazolyl)-8-(methyloxy)-2-(tetrahydro-2H-pyran-4-yl)-1-({3-[(trifluoromethyl)oxy]phenyl}methyl)-1H-imidazo[4,5-c]quinoline |
| 94 | 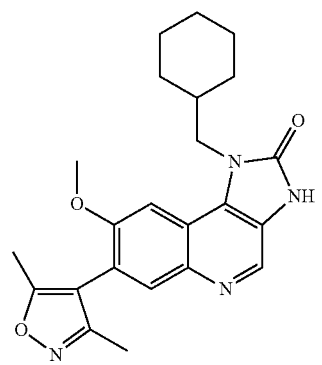 [SMILES: COc1cc2c(cc1-c1c(C)noc1C)ncc1[nH]c(=O)n(CC3CCCCC3)c12] | 1-(cyclohexylmethyl)-7-(3,5-dimethyl-4-isoxazolyl)-8-(methyloxy)-1,3-dihydro-2H-imidazo[4,5-c]quinolin-2-one |
| 95 | 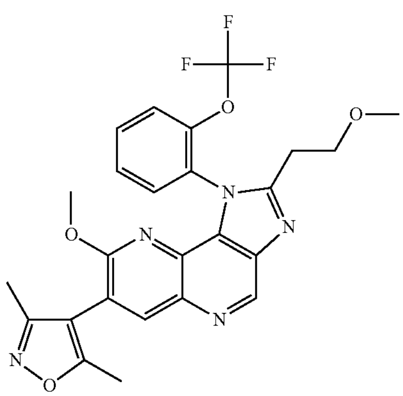 | 7-(3,5-dimethyl-4-isoxazolyl)-8-(methyloxy)-2-[2-(methyloxy)ethyl]-1-{2-[(trifluoromethyl)oxy]phenyl}-1H-imidazo[4,5-c]-1,5-naphthyridine |
| 96 | 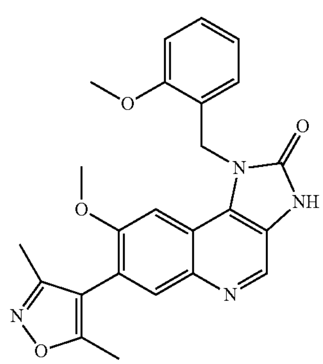 [SMILES: COc1ccccc1Cn1c(=O)[nH]c2cnc3cc(-c4c(C)noc4C)c(OC)cc3c21] | 7-(3,5-dimethyl-4-isoxazolyl)-8-(methyloxy)-1-{[2-(methyloxy)phenyl]methyl}-1,3-dihydro-2H-imidazo[4,5-c]quinolin-2-one |

| Example | Structure | Name |
|---|---|---|
| 97 | 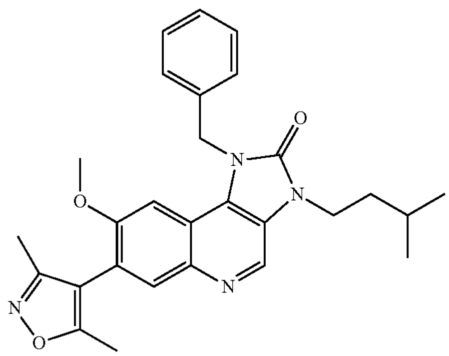 [SMILES: COc1cc2c(cc1-c1c(C)noc1C)ncc1c2n(Cc2ccccc2)c(=O)n1CCC(C)C] | 7-(3,5-dimethyl-4-isoxazolyl)-3-(3-methylbutyl)-8-(methyloxy)-1-(phenylmethyl)-1,3-dihydro-2H-imidazo[4,5-c]quinolin-2-one |
| 98 | 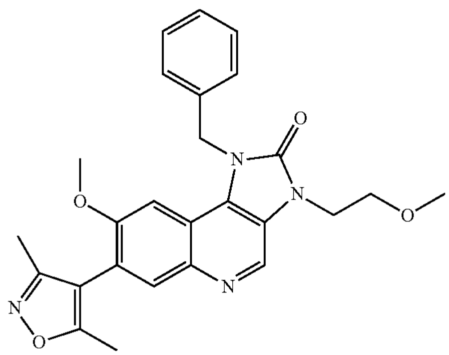 [SMILES: COCCn1c(=O)n(Cc2ccccc2)c2c3cc(OC)c(-c4c(C)noc4C)cc3ncc21] | 7-(3,5-dimethyl-4-isoxazolyl)-8-(methyloxy)-3-[2-(methyloxy)ethyl]-1-(phenylmethyl)-1,3-dihydro-2H-imidazo[4,5-c]quinolin-2-one |
| 99 | 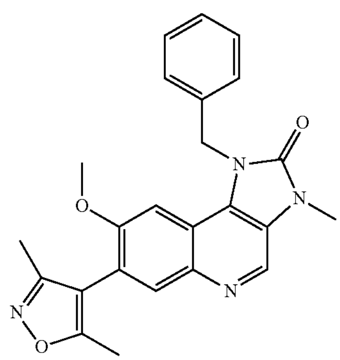 [SMILES: COc1cc2c(cc1-c1c(C)noc1C)ncc1c2n(Cc2ccccc2)c(=O)n1C] | 7-(3,5-dimethyl-4-isoxazolyl)-3-methyl-8-(methyloxy)-1-(phenylmethyl)-1,3-dihydro-2H-imidazo[4,5-c]quinolin-2-one |
| 100 | 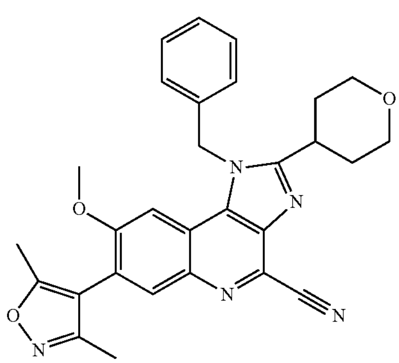 [SMILES: COc1cc2c(cc1-c1c(C)noc1C)nc(C#N)c1nc(C3CCOCC3)n(Cc3ccccc3)c12] | 7-(3,5-dimethyl-4-isoxazolyl)-8-(methyloxy)-1-(phenylmethyl)-2-(tetrahydro-2H-pyran-4-yl)-1H-imidazo[4,5-c]quinoline-4-carbonitrile |

| Example | Structure | Name |
|---|---|---|
| 101 | 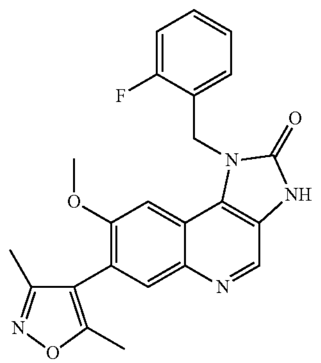 [SMILES: COc1cc2c(cc1-c1c(C)noc1C)ncc1[nH]c(=O)n(Cc3ccccc3F)c12] | 7-(3,5-dimethyl-4-isoxazolyl)-1-[(2-fluorophenyl)methyl]-8-(methyloxy)-1,3-dihydro-2H-imidazo[4,5-c]quinolin-2-one |
| 102 | 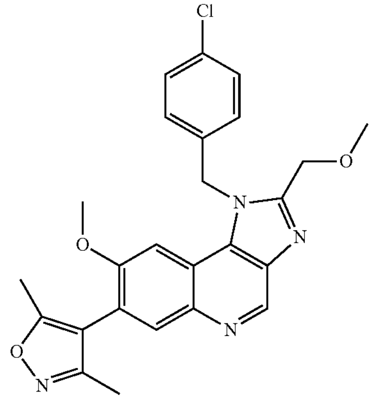 [SMILES: COCc1nc2cnc3cc(-c4c(C)noc4C)c(OC)cc3c2n1Cc1ccc(Cl)cc1] | 1-[(4-chlorophenyl)methyl]-7-(3,5-dimethyl-4-isoxazolyl)-8-(methyloxy)-2-[(methyloxy)methyl]-1H-imidazo[4,5-c]quinoline |
| 103 | 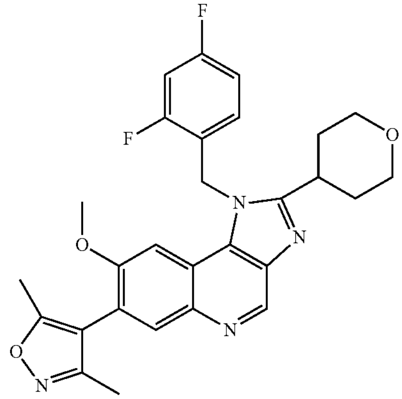 [SMILES: COc1cc2c(cc1-c1c(C)noc1C)ncc1nc(C3CCOCC3)n(Cc3ccc(F)cc3F)c12] | 1-[(2,4-difluorophenyl)methyl]-7-(3,5-dimethyl-4-isoxazolyl)-8-(methyloxy)-2-(tetrahydro-2H-pyran-4-yl)-1H-imidazo[4,5-c]quinoline |
| 104 | 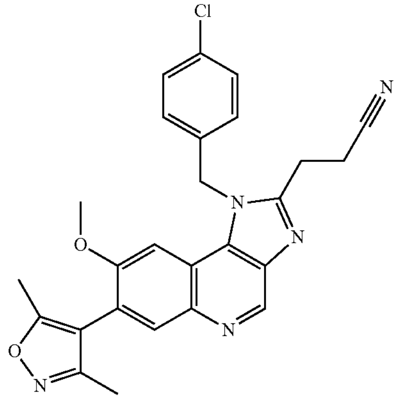 [SMILES: COc1cc2c(cc1-c1c(C)noc1C)ncc1nc(CCC#N)n(Cc3ccc(Cl)cc3)c12] | 3-[1-[(4-chlorophenyl)methyl]-7-(3,5-dimethyl-4-isoxazolyl)-8-(methyloxy)-1H-imidazo[4,5-c]quinolin-2-yl]propanenitrile |

-continued

| Example | Structure | Name |
|---|---|---|
| 105 | 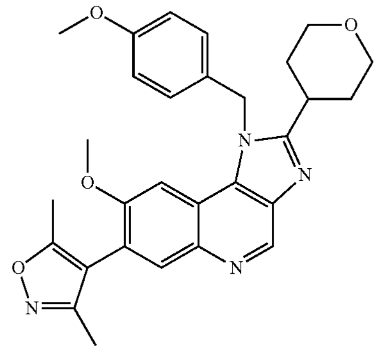 [SMILES: COc1ccc(Cn2c(C3CCOCC3)nc3cnc4cc(-c5c(C)noc5C)c(OC)cc4c32)cc1] | 7-(3,5-dimethyl-4-isoxazolyl)-8-(methyloxy)-1-{[4-(methyloxy)phenyl]methyl}-2-(tetrahydro-2H-pyran-4-yl)-1H-imidazo[4,5-c]quinoline |
| 106 | 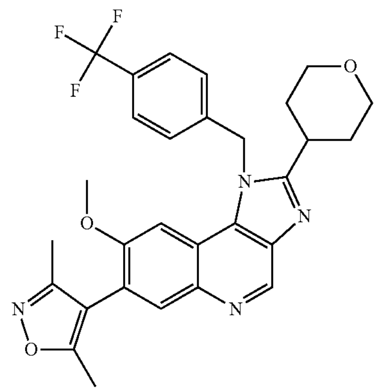 [SMILES: COc1cc2c(cc1-c1c(C)noc1C)ncc1nc(C3CCOCC3)n(Cc3ccc(C(F)(F)F)cc3)c12] | 7-(3,5-dimethyl-4-isoxazolyl)-8-(methyloxy)-2-(tetrahydro-2H-pyran-4-yl)-1-{[4-(trifluoromethyl)phenyl]methyl}-1H-imidazo[4,5-c]quinoline |
| 107 | 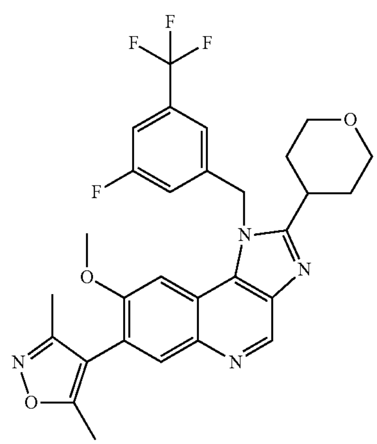 [SMILES: COc1cc2c(cc1-c1c(C)noc1C)ncc1nc(C3CCOCC3)n(Cc3cc(F)cc(C(F)(F)F)c3)c12] | 7-(3,5-dimethyl-4-isoxazolyl)-1-{[3-fluoro-5-(trifluoromethyl)phenyl]methyl}-8-(methyloxy)-2-(tetrahydro-2H-pyran-4-yl)-1H-imidazo[4,5-c]quinoline |
| 108 | 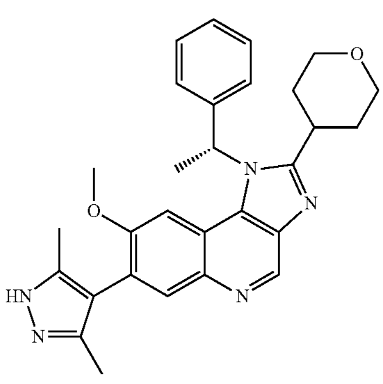 [SMILES: COc1cc2c(cc1-c1c(C)n[nH]c1C)ncc1nc(C3CCOCC3)n([C@H](C)c3ccccc3)c12] | 7-(3,5-dimethyl-1H-pyrazol-4-yl)-8-(methyloxy)-1-[(1R)-1-phenylethyl]-2-(tetrahydro-2H-pyran-4-yl)-1H-imidazo[4,5-c]quinoline |

-continued

| Example | Structure | Name |
|---|---|---|
| 109 | 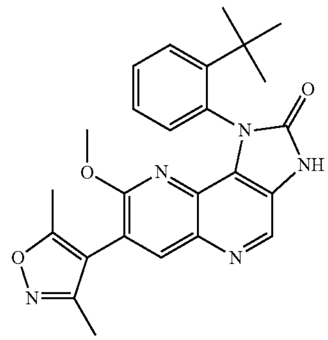 [SMILES: COc1nc2c(cc1-c1c(C)noc1C)ncc1[nH]c(=O)n(-c3ccccc3C(C)(C)C)c12] | 1-[2-(1,1-dimethylethyl)phenyl]-7-(3,5-dimethyl-4-isoxazolyl)-8-(methyloxy)-1,3-dihydro-2H-imidazo[4,5-c]-1,5-naphthyridin-2-one |
| 110 | 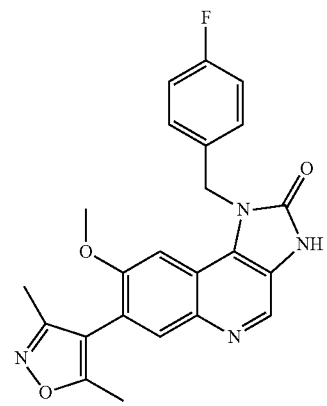 [SMILES: COc1cc2c(cc1-c1c(C)noc1C)ncc1[nH]c(=O)n(Cc3ccc(F)cc3)c12] | 7-(3,5-dimethyl-4-isoxazolyl)-1-[(4-fluorophenyl)methyl]-8-(methyloxy)-1,3-dihydro-2H-imidazo[4,5-c]quinolin-2-one |
| 111 | 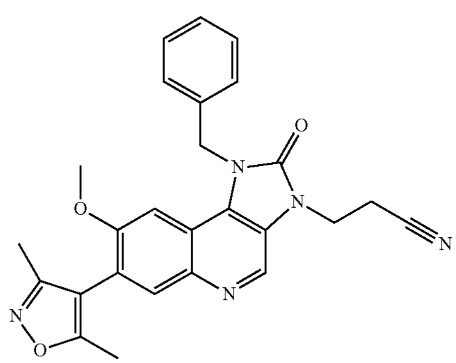 [SMILES: COc1cc2c(cc1-c1c(C)noc1C)ncc1c2n(Cc2ccccc2)c(=O)n1CCC#N] | 3-[7-(3,5-dimethyl-4-isoxazolyl)-8-(methyloxy)-2-oxo-1-(phenylmethyl)-1,2-dihydro-3H-imidazo[4,5-c]quinolin-3-yl]propanenitrile |
| 112 | 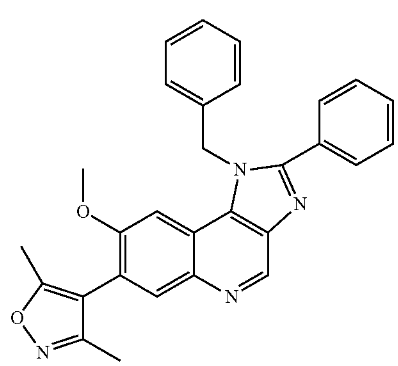 [SMILES: COc1cc2c(cc1-c1c(C)noc1C)ncc1nc(-c3ccccc3)n(Cc3ccccc3)c12] | 7-(3,5-dimethyl-4-isoxazolyl)-8-(methyloxy)-2-phenyl-1-(phenylmethyl)-1H-imidazo[4,5-c]quinoline |

-continued

| Example | Structure | Name |
|---|---|---|
| 113 | 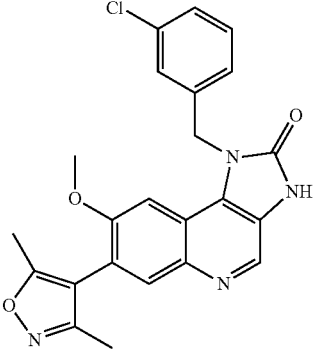 [SMILES: COc1cc2c(cc1-c1c(C)noc1C)ncc1[nH]c(=O)n(Cc3cccc(Cl)c3)c12] | 1-[(3-chlorophenyl)methyl]-7-(3,5-dimethyl-4-isoxazolyl)-8-(methyloxy)-1,3-dihydro-2H-imidazo[4,5-c]quinolin-2-one |
| 114 | 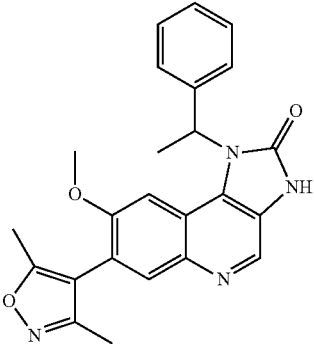 [SMILES: COc1cc2c(cc1-c1c(C)noc1C)ncc1[nH]c(=O)n(C(C)c3ccccc3)c12] | 7-(3,5-dimethyl-4-isoxazolyl)-8-(methyloxy)-1-(1-phenylethyl)-1,3-dihydro-2H-imidazo[4,5-c]quinolin-2-one |
| 115 | 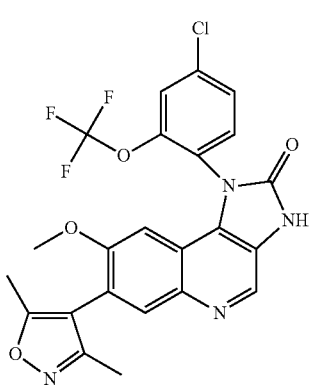 [SMILES: COc1cc2c(cc1-c1c(C)noc1C)ncc1[nH]c(=O)n(-c3ccc(Cl)cc3OC(F)(F)F)c12] | 1-{4-chloro-2-[(trifluoromethyl)oxy]phenyl}-7-(3,5-dimethyl-4-isoxazolyl)-8-(methyloxy)-1,3-dihydro-2H-imidazo[4,5-c]quinolin-2-one |
| 116 | 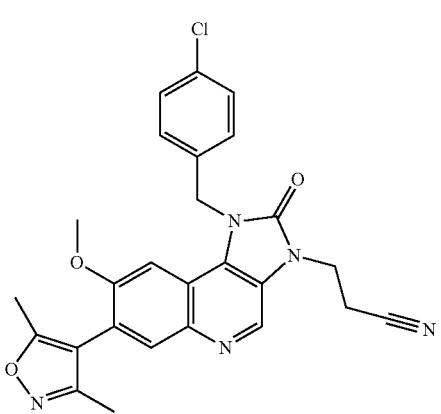 [SMILES: COc1cc2c(cc1-c1c(C)noc1C)ncc1c2n(Cc2ccc(Cl)cc2)c(=O)n1CCC#N] | 3-[1-[(4-chlorophenyl)methyl]-7-(3,5-dimethyl-4-isoxazolyl)-8-(methyloxy)-2-oxo-1,2-dihydro-3H-imidazo[4,5-c]quinolin-3-yl]propanenitrile |

| Example | Structure | Name |
|---|---|---|
| 117 | 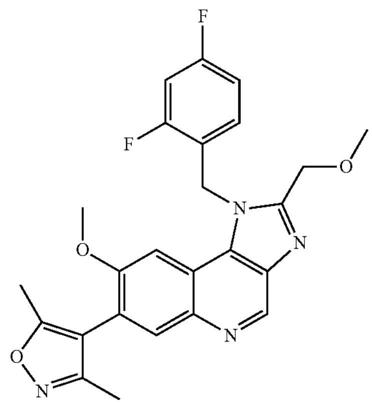 [SMILES: COCc1nc2cnc3cc(-c4c(C)noc4C)c(OC)cc3c2n1Cc1ccc(F)cc1F] | 1-[(2,4-difluorophenyl)methyl]-7-(3,5-dimethyl-4-isoxazolyl)-8-(methyloxy)-2-[(methyloxy)methyl]-1H-imidazo[4,5-c]quinoline |
| 118 | 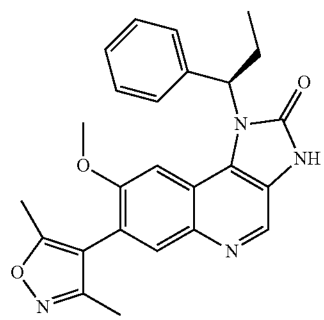 [SMILES: CC[C@H](c1ccccc1)n1c(=O)[nH]c2cnc3cc(-c4c(C)noc4C)c(OC)cc3c21] | 7-(3,5-dimethyl-4-isoxazolyl)-8-(methyloxy)-1-[(1R)-1-phenylpropyl]-1,3-dihydro-2H-imidazo[4,5-c]quinolin-2-one |
| 119 | 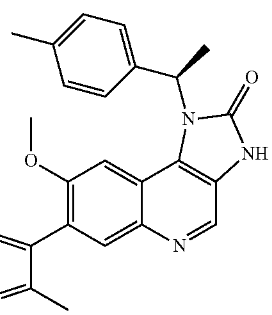 | 7-(3,5-dimethyl-4-isoxazolyl)-8-(methyloxy)-1-[(1R)-1-(4-methylphenyl)ethyl]-1,3-dihydro-2H-imidazo[4,5-c]quinolin-2-one |
| 120 | 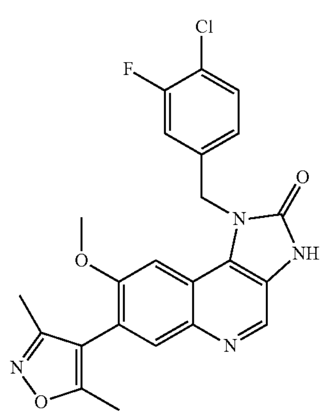 | 1-[(4-chloro-3-fluorophenyl)methyl]-7-(3,5-dimethyl-4-isoxazolyl)-8-(methyloxy)-1,3-dihydro-2H-imidazo[4,5-c]quinolin-2-one |

| Example | Structure | Name |
|---|---|---|
| 121 | 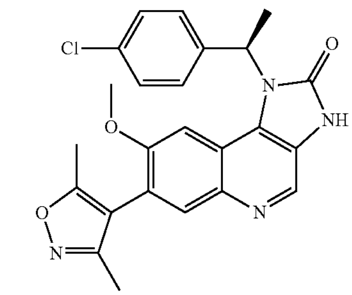 | 1-[(1R)-1-(4-chlorophenyl)ethyl]-7-(3,5-dimethyl-4-isoxazolyl)-8-(methyloxy)-1,3-dihydro-2H-imidazo[4,5-c]quinolin-2-one |
| 122 | 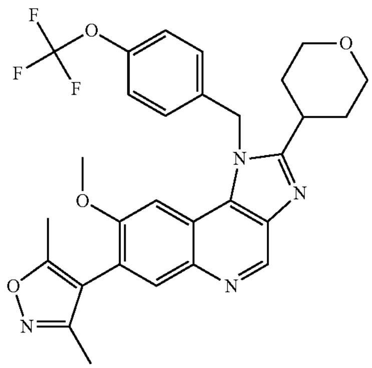 [SMILES: COc1cc2c(cc1-c1c(C)noc1C)ncc1nc(C3CCOCC3)n(Cc3ccc(OC(F)(F)F)cc3)c12] | 7-(3,5-dimethyl-4-isoxazolyl)-8-(methyloxy)-2-(tetrahydro-2H-pyran-4-yl)-1-({4-[(trifluoromethyl)oxy]phenyl}methyl)-1H-imidazo[4,5-c]quinoline |
| 123 | 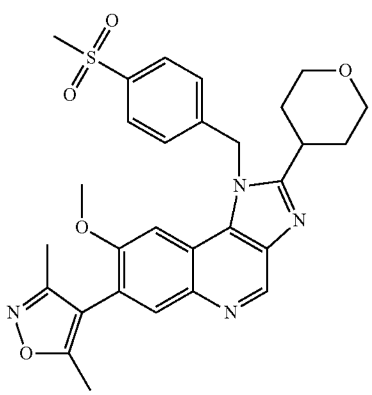 [SMILES: COc1cc2c(cc1-c1c(C)noc1C)ncc1nc(C3CCOCC3)n(Cc3ccc(S(C)(=O)=O)cc3)c12] | 7-(3,5-dimethyl-4-isoxazolyl)-8-(methyloxy)-1-{[4-(methylsulfonyl)phenyl]methyl}-2-(tetrahydro-2H-pyran-4-yl)-1H-imidazo[4,5-c]quinoline |
| 124 | 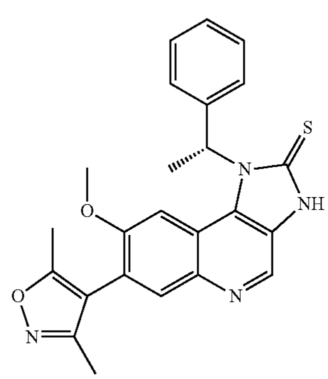 [SMILES: COc1cc2c(cc1-c1c(C)noc1C)ncc1[nH]c(=S)n([C@H](C)c3ccccc3)c12] | 7-(3,5-dimethyl-4-isoxazolyl)-8-(methyloxy)-1-[(1R)-1-phenylethyl]-1,3-dihydro-2H-imidazo[4,5-c]quinoline-2-thione |

| Example | Structure | Name |
|---|---|---|
| 125 | 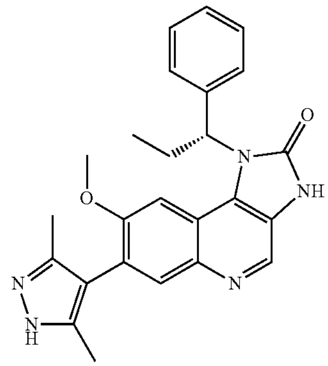 [SMILES: CC[C@H](c1ccccc1)n1c(=O)[nH]c2cnc3cc(-c4c(C)n[nH]c4C)c(OC)cc3c21] | 7-(3,5-dimethyl-1H-pyrazol-4-yl)-8-(methyloxy)-1-[(1R)-1-phenylpropyl]-1,3-dihydro-2H-imidazo[4,5-c]quinolin-2-one |
| 126 | 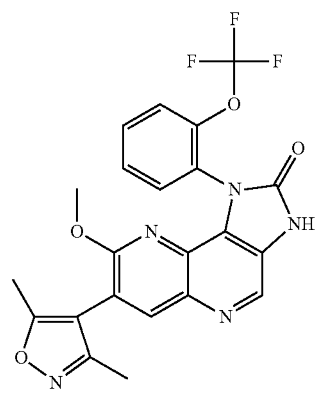 [SMILES: COc1nc2c(cc1-c1c(C)noc1C)ncc1[nH]c(=O)n(-c3ccccc3OC(F)(F)F)c12] | 7-(3,5-dimethyl-4-isoxazolyl)-8-(methyloxy)-1-{2-[(trifluoromethyl)oxy]phenyl}-1,3-dihydro-2H-imidazo[4,5-c]-1,5-naphthyridin-2-one |
| 127 | 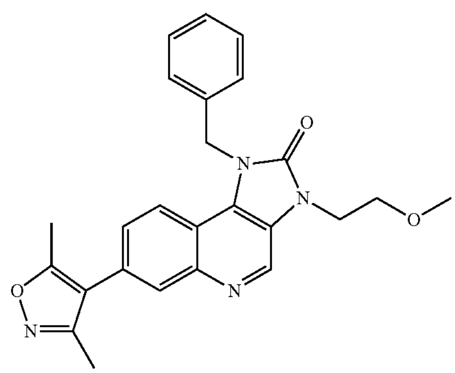 [SMILES: COCCn1c(=O)n(Cc2ccccc2)c2c3ccc(-c4c(C)noc4C)cc3ncc21] | 7-(3,5-dimethyl-4-isoxazolyl)-3-[2-(methyloxy)ethyl]-1-(phenylmethyl)-1,3-dihydro-2H-imidazo[4,5-c]quinolin-2-one |
| 128 | 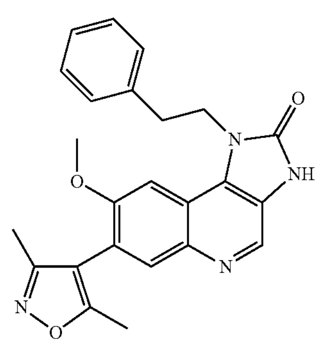 [SMILES: COc1cc2c(cc1-c1c(C)noc1C)ncc1[nH]c(=O)n(CCc3ccccc3)c12] | 7-(3,5-dimethyl-4-isoxazolyl)-8-(methyloxy)-1-(2-phenylethyl)-1,3-dihydro-2H-imidazo[4,5-c]quinolin-2-one |

-continued

| Example | Structure | Name |
|---------|-----------|------|
| 129 | 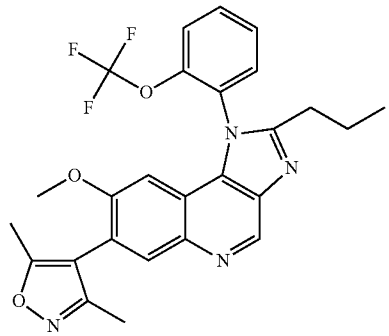 [SMILES: CCCc1nc2cnc3cc(-c4c(C)noc4C)c(OC)cc3c2n1-c1ccccc1OC(F)(F)F] | 7-(3,5-dimethyl-4-isoxazolyl)-8-(methyloxy)-2-propyl-1-{2-[(trifluoromethyl)oxy]phenyl}-1H-imidazo[4,5-c]quinoline |
| 130 | 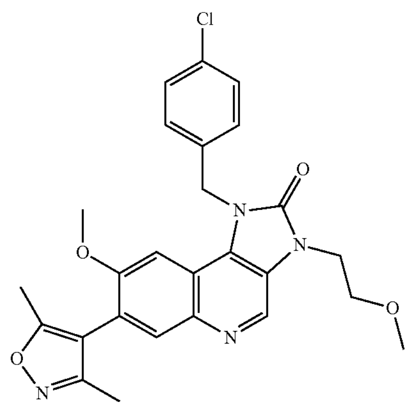 [SMILES: COCCn1c(=O)n(Cc2ccc(Cl)cc2)c2c3cc(OC)c(-c4c(C)noc4C)cc3ncc21] | 1-[(4-chlorophenyl)methyl]-7-(3,5-dimethyl-4-isoxazolyl)-8-(methyloxy)-3-[2-(methyloxy)ethyl]-1,3-dihydro-2H-imidazo[4,5-c]quinolin-2-one |
| 131 | 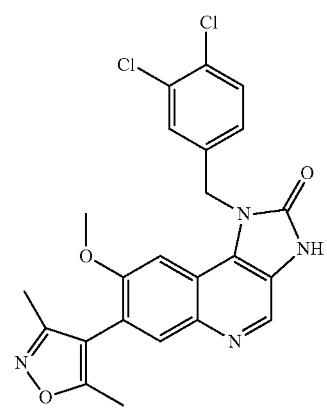 [SMILES: COc1cc2c(cc1-c1c(C)noc1C)ncc1[nH]c(=O)n(Cc3ccc(Cl)c(Cl)c3)c12] | 1-[(3,4-dichlorophenyl)methyl]-7-(3,5-dimethyl-4-isoxazolyl)-8-(methyloxy)-1,3-dihydro-2H-imidazo[4,5-c]quinolin-2-one |
| 132 | 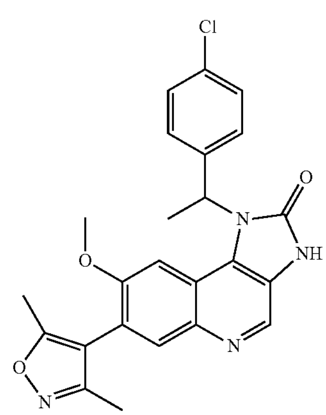 [SMILES: COc1cc2c(cc1-c1c(C)noc1C)ncc1[nH]c(=O)n(C(C)c3ccc(Cl)cc3)c12] | 1-[1-(4-chlorophenyl)ethyl]-7-(3,5-dimethyl-4-isoxazolyl)-8-(methyloxy)-1,3-dihydro-2H-imidazo[4,5-c]quinolin-2-one |

-continued

| Example | Structure | Name |
| --- | --- | --- |
| 133 | 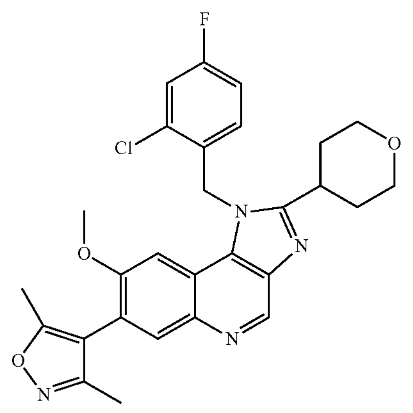 [SMILES: COc1cc2c(cc1-c1c(C)noc1C)ncc1nc(C3CCOCC3)n(Cc3ccc(F)cc3Cl)c12] | 1-[(2-chloro-4-fluorophenyl)methyl]-7-(3,5-dimethyl-4-isoxazolyl)-8-(methyloxy)-2-(tetrahydro-2H-pyran-4-yl)-1H-imidazo[4,5-c]quinoline |
| 134 | 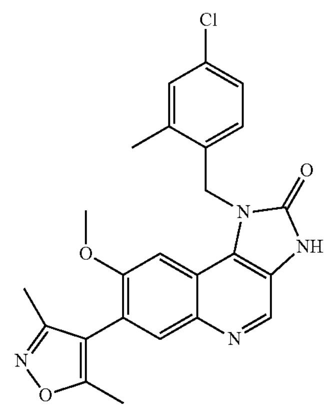 [SMILES: COc1cc2c(cc1-c1c(C)noc1C)ncc1[nH]c(=O)n(Cc3ccc(Cl)cc3C)c12] | 1-[(4-chloro-2-methylphenyl)methyl]-7-(3,5-dimethyl-4-isoxazolyl)-8-(methyloxy)-1,3-dihydro-2H-imidazo[4,5-c]quinolin-2-one |
| 135 | 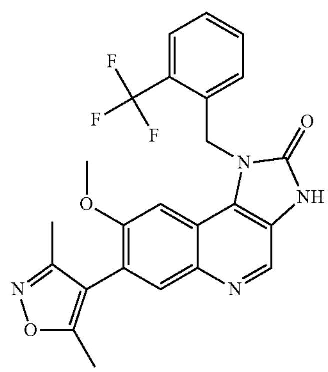 [SMILES: COc1cc2c(cc1-c1c(C)noc1C)ncc1[nH]c(=O)n(Cc3ccccc3C(F)(F)F)c12] | 7-(3,5-dimethyl-4-isoxazolyl)-8-(methyloxy)-1-{[2-(trifluoromethyl)phenyl]methyl}-1,3-dihydro-2H-imidazo[4,5-c]quinolin-2-one |
| 136 | 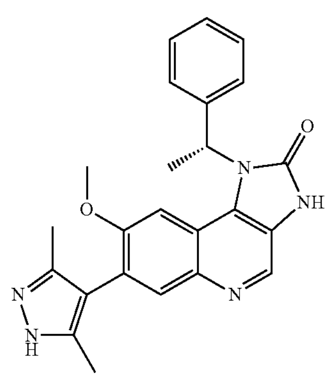 [SMILES: COc1cc2c(cc1-c1c(C)n[nH]c1C)ncc1[nH]c(=O)n([C@H](C)c3ccccc3)c12] | 7-(3,5-dimethyl-1H-pyrazol-4-yl)-8-(methyloxy)-1-[(1R)-1-phenylethyl]-1,3-dihydro-2H-imidazo[4,5-c]quinolin-2-one |

-continued

| Example | Structure | Name |
|---|---|---|
| 137 | 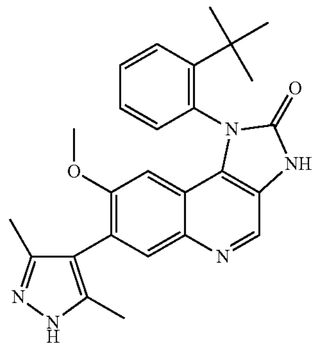 [SMILES: COc1cc2c(cc1-c1c(C)n[nH]c1C)ncc1[nH]c(=O)n(-c3ccccc3C(C)(C)C)c12] | 1-[2-(1,1-dimethylethyl)phenyl]-7-(3,5-dimethyl-1H-pyrazol-4-yl)-8-(methyloxy)-1,3-dihydro-2H-imidazo[4,5-c]quinolin-2-one |
| 138 | 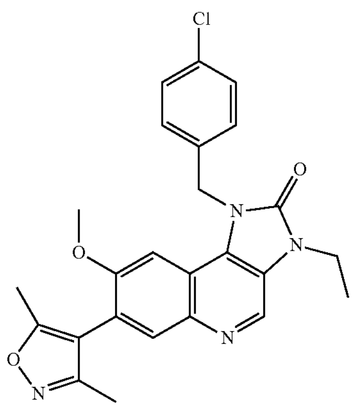 [SMILES: CCn1c(=O)n(Cc2ccc(Cl)cc2)c2c3cc(OC)c(-c4c(C)noc4C)cc3ncc21] | 1-[(4-chlorophenyl)methyl]-7-(3,5-dimethyl-4-isoxazolyl)-3-ethyl-8-(methyloxy)-1,3-dihydro-2H-imidazo[4,5-c]quinolin-2-one |
| 139 | 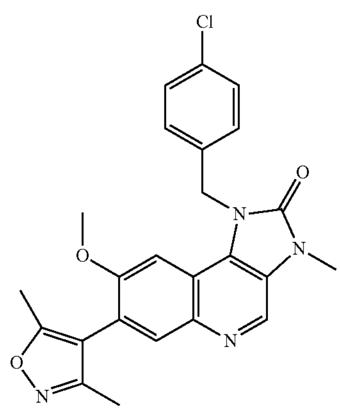 [SMILES: COc1cc2c(cc1-c1c(C)noc1C)ncc1c2n(Cc2ccc(Cl)cc2)c(=O)n1C] | 1-[(4-chlorophenyl)methyl]-7-(3,5-dimethyl-4-isoxazolyl)-3-methyl-8-(methyloxy)-1,3-dihydro-2H-imidazo[4,5-c]quinolin-2-one |
| 140 | 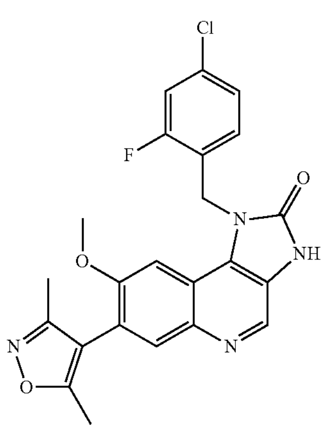 [SMILES: COc1cc2c(cc1-c1c(C)noc1C)ncc1[nH]c(=O)n(Cc3ccc(Cl)cc3F)c12] | 1-[(4-chloro-2-fluorophenyl)methyl]-7-(3,5-dimethyl-4-isoxazolyl)-8-(methyloxy)-1,3-dihydro-2H-imidazo[4,5-c]quinolin-2-one |

| Example | Structure | Name |
|---|---|---|
| 141 | 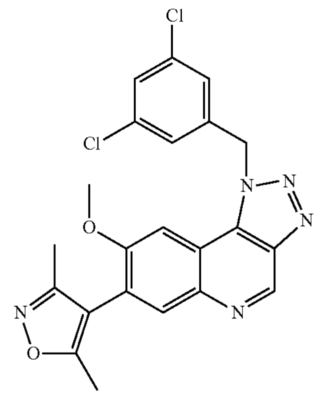 [SMILES: COc1cc2c(cc1-c1c(C)noc1C)ncc1nnn(Cc3cc(Cl)cc(Cl)c3)c12] | 1-[(3,5-dichlorophenyl)methyl]-7-(3,5-dimethyl-4-isoxazolyl)-8-(methyloxy)-1H-[1,2,3]triazolo[4,5-c]quinoline |
| 142 | 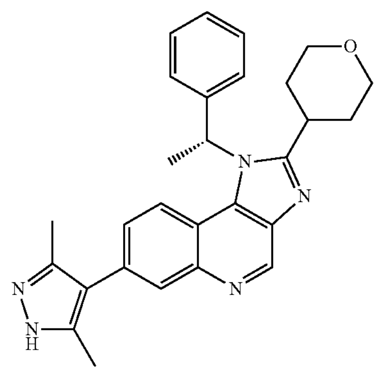 [SMILES: Cc1n[nH]c(C)c1-c1ccc2c(c1)ncc1nc(C3CCOCC3)n([C@H](C)c3ccccc3)c12] | 7-(3,5-dimethyl-1H-pyrazol-4-yl)-1-[(1R)-1-phenylethyl]-2-(tetrahydro-2H-pyran-4-yl)-1H-imidazo[4,5-c]quinoline |
| 143 | 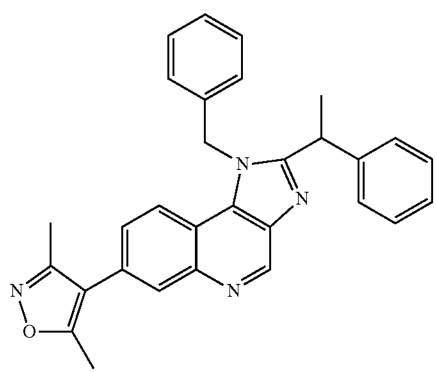 [SMILES: Cc1noc(C)c1-c1ccc2c(c1)ncc1nc(C(C)c3ccccc3)n(Cc3ccccc3)c12] | 7-(3,5-dimethyl-4-isoxazolyl)-2-(1-phenylethyl)-1-(phenylmethyl)-1H-imidazo[4,5-c]quinoline |
| 144 | 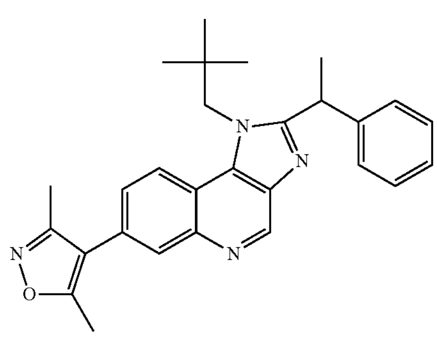 [SMILES: Cc1noc(C)c1-c1ccc2c(c1)ncc1nc(C(C)c3ccccc3)n(CC(C)(C)C)c12] | 7-(3,5-dimethyl-4-isoxazolyl)-1-(2,2-dimethylpropyl)-2-(1-phenylethyl)-1H-imidazo[4,5-c]quinoline |

-continued

| Example | Structure | Name |
| --- | --- | --- |
| 145 | 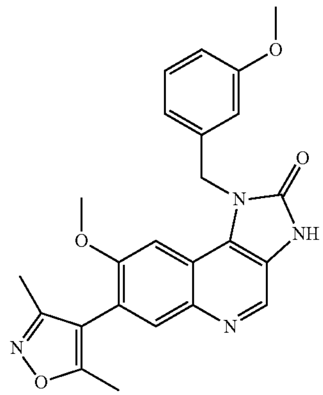 [SMILES: COc1cccc(Cn2c(=O)[nH]c3cnc4cc(-c5c(C)noc5C)c(OC)cc4c32)c1] | 7-(3,5-dimethyl-4-isoxazolyl)-8-(methyloxy)-1-[2-(methyloxy)phenyl]-1,3-dihydro-2H-imidazo[4,5-c]quinolin-2-one |
| 146 | 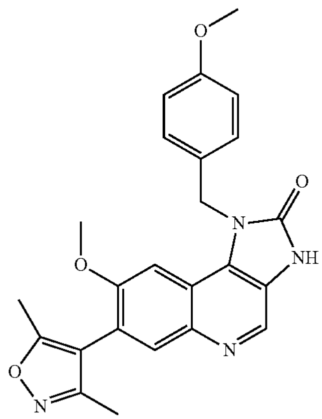 [SMILES: COc1ccc(Cn2c(=O)[nH]c3cnc4cc(-c5c(C)noc5C)c(OC)cc4c32)cc1] | 7-(3,5-dimethyl-4-isoxazolyl)-8-(methyloxy)-1-{[4-(methyloxy)phenyl]methyl}-1,3-dihydro-2H-imidazo[4,5-c]quinolin-2-one |
| 147 | 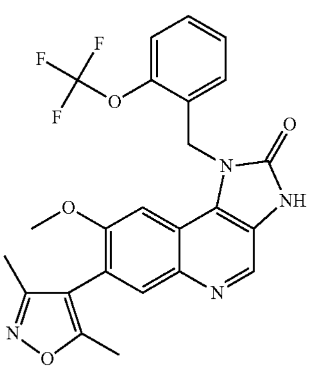 [SMILES: COc1cc2c(cc1-c1c(C)noc1C)ncc1[nH]c(=O)n(Cc3ccccc3OC(F)(F)F)c12] | 7-(3,5-dimethyl-4-isoxazolyl)-8-(methyloxy)-1-({2-[(trifluoromethyl)oxy]phenyl}methyl)-1,3-dihydro-2H-imidazo[4,5-c]quinolin-2-one |
| 148 | 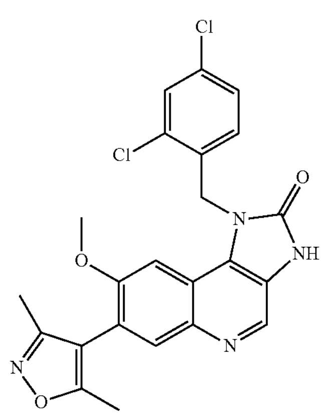 [SMILES: COc1cc2c(cc1-c1c(C)noc1C)ncc1[nH]c(=O)n(Cc3ccc(Cl)cc3Cl)c12] | 1-[(2,4-dichlorophenyl)methyl]-7-(3,5-dimethyl-4-isoxazolyl)-8-(methyloxy)-1,3-dihydro-2H-imidazo[4,5-c]quinolin-2-one |

| Example | Structure | Name |
|---|---|---|
| 149 | 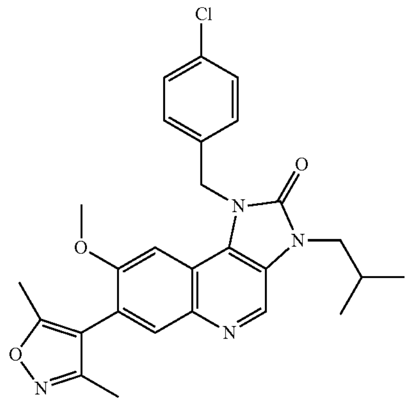 [SMILES: COc1cc2c(cc1-c1c(C)noc1C)ncc1c2n(Cc2ccc(Cl)cc2)c(=O)n1CC(C)C] | 1-[(4-chlorophenyl)methyl]-7-(3,5-dimethyl-4-isoxazolyl)-8-(methyloxy)-3-(2-methylpropyl)-1,3-dihydro-2H-imidazo[4,5-c]quinolin-2-one |
| 150 | 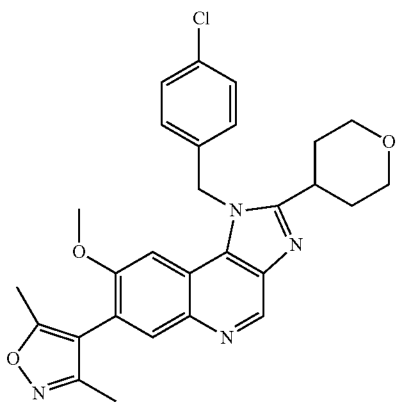 [SMILES: COc1cc2c(cc1-c1c(C)noc1C)ncc1nc(C3CCOCC3)n(Cc3ccc(Cl)cc3)c12] | 1-[(4-chlorophenyl)methyl]-7-(3,5-dimethyl-4-isoxazolyl)-8-(methyloxy)-2-(tetrahydro-2H-pyran-4-yl)-1H-imidazo[4,5-c]quinoline |
| 151 | 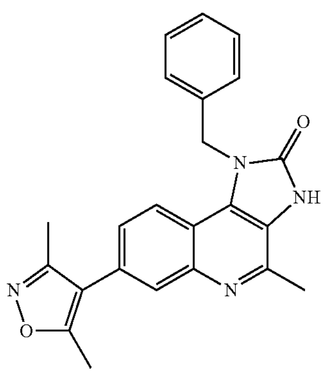 [SMILES: Cc1noc(C)c1-c1ccc2c(c1)nc(C)c1[nH]c(=O)n(Cc3ccccc3)c12] | 7-(3,5-dimethyl-4-isoxazolyl)-4-methyl-1-(phenylmethyl)-1,3-dihydro-2H-imidazo[4,5-c]quinolin-2-one |
| 152 | 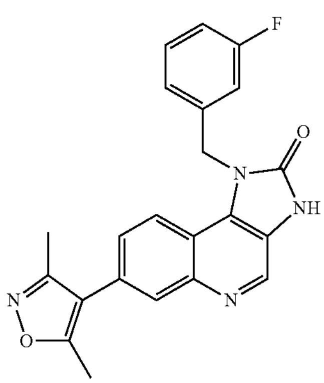 [SMILES: Cc1noc(C)c1-c1ccc2c(c1)ncc1[nH]c(=O)n(Cc3cccc(F)c3)c12] | 7-(3,5-dimethyl-4-isoxazolyl)-1-[(3-fluorophenyl)methyl]-1,3-dihydro-2H-imidazo[4,5-c]quinolin-2-one |

-continued

| Example | Structure | Name |
|---|---|---|
| 153 | 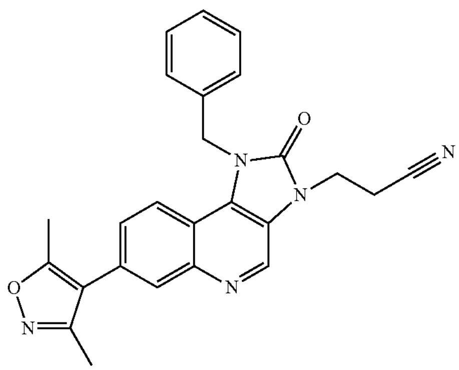 [SMILES: Cc1noc(C)c1-c1ccc2c(c1)ncc1c2n(Cc2ccccc2)c(=O)n1CCC#N] | 3-[7-(3,5-dimethyl-4-isoxazolyl)-2-oxo-1-(phenylmethyl)-1,2-dihydro-3H-imidazo[4,5-c]quinolin-3-yl]propanenitrile |
| 154 | 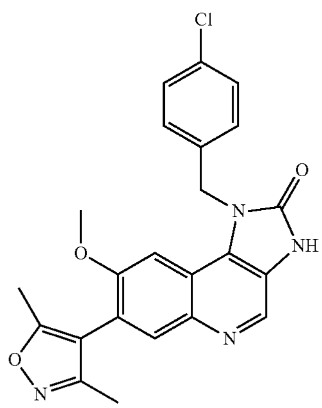 [SMILES: COc1cc2c(cc1-c1c(C)noc1C)ncc1[nH]c(=O)n(Cc3ccc(Cl)cc3)c12] | 1-[(4-chlorophenyl)methyl]-7-(3,5-dimethyl-4-isoxazolyl)-8-(methyloxy)-1,3-dihydro-2H-imidaszo[4,5-c]quinolin-2-one |
| 155 | 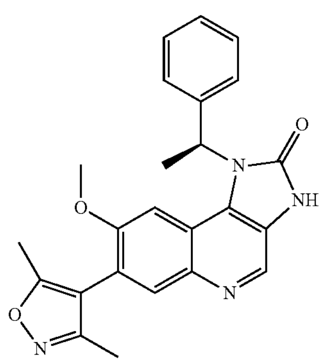 [SMILES: COc1cc2c(cc1-c1c(C)noc1C)ncc1[nH]c(=O)n([C@@H](C)c3ccccc3)c12] | 7-(3,5-dimethyl-4-isoxazolyl)-8-(methyloxy)-1-[(1S)-1-phenylethyl]-1,3-dihydro-2H-imidazo[4,5-c]quinolin-2-one |
| 156 | 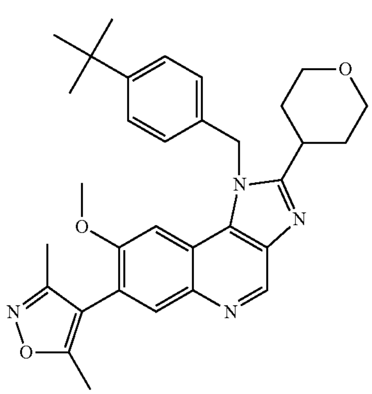 [SMILES: COc1cc2c(cc1-c1c(C)noc1C)ncc1nc(C3CCOCC3)n(Cc3ccc(C(C)(C)C)cc3)c12] | 1-{[4-(1,1-dimethylethyl)phenyl]methyl}-7-(3,5-dimethyl-4-isoxazolyl)-8-(methyloxy)-2-(tetrahydro-2H-pyran-4-yl)-1H-imidazo[4,5-c]quinoline |

-continued

| Example | Structure | Name |
| --- | --- | --- |
| 157 | 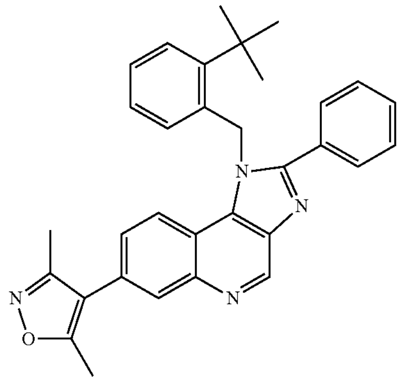 [SMILES: Cc1noc(C)c1-c1ccc2c(c1)ncc1nc(-c3ccccc3)n(Cc3ccccc3C(C)(C)C)c12] | 1-[2-(1,1-dimethylethyl)phenyl]-7-(3,5-dimethyl-4-isoxazolyl)-2-phenyl-1H-imidazo[4,5-c]quinoline |
| 158 | 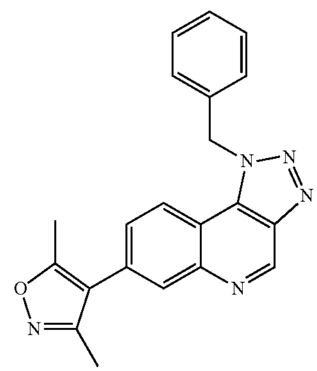 [SMILES: Cc1noc(C)c1-c1ccc2c(c1)ncc1nnn(Cc3ccccc3)c12] | 7-(3,5-dimethyl-4-isoxazolyl)-1-(phenylmethyl)-1H-[1,2,3]triazolo[4,5-c]quinoline |
| 159 | 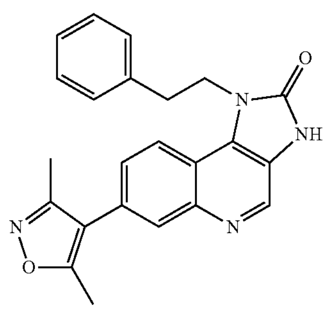 [SMILES: Cc1noc(C)c1-c1ccc2c(c1)ncc1[nH]c(=O)n(CCc3ccccc3)c12] | 7-(3,5-dimethyl-4-isoxazolyl)-1-(2-phenylethyl)-1,3-dihydro-2H-imidazo[4,5-c]quinolin-2-one |
| 160 | 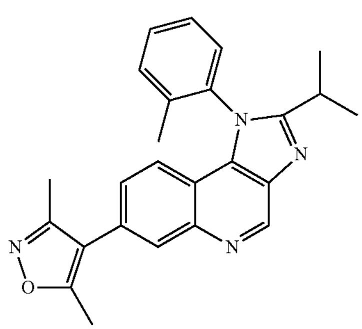 [SMILES: Cc1ccccc1-n1c(C(C)C)nc2cnc3cc(-c4c(C)noc4C)ccc3c21] | 7-(3,5-dimethyl-4-isoxazolyl)-2-(1-methylethyl)-1-(2-methylphenyl)-1H-imidazo[4,5-c]quinoline |

-continued

| Example | Structure | Name |
|---|---|---|
| 161 | 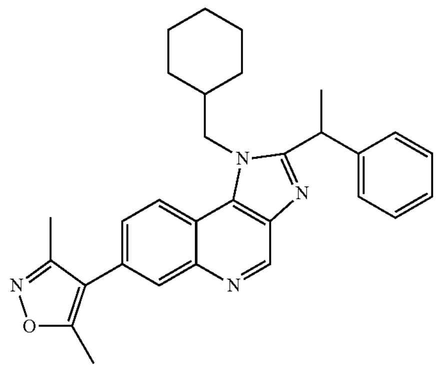 [SMILES: Cc1noc(C)c1-c1ccc2c(c1)ncc1nc(C(C)c3ccccc3)n(CC3CCCCC3)c12] | 1-(cyclohexylmethyl)-7-(3,5-dimethyl-4-isoxazolyl)-2-(1-phenylethyl)-1H-imidazo[4,5-c]quinoline |
| 162 | 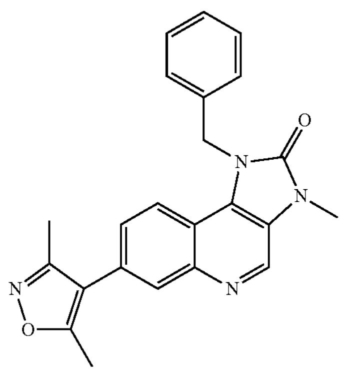 [SMILES: Cc1noc(C)c1-c1ccc2c(c1)ncc1c2n(Cc2ccccc2)c(=O)n1C] | 7-(3,5-dimethyl-4-isoxazolyl)-3-methyl-1-(phenylmethyl)-1,3-dihydro-2H-imidazo[4,5-c]quinolin-2-one |
| 163 | 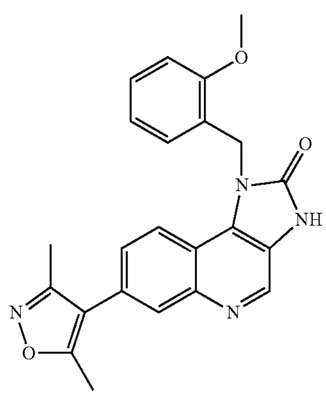 [SMILES: COc1ccccc1Cn1c(=O)[nH]c2cnc3cc(-c4c(C)noc4C)ccc3c21] | 7-(3,5-dimethyl-4-isoxazolyl)-1-[2-(methyloxy)phenyl]-1,3-dihydro-2H-imidazo[4,5-c]quinolin-2-one |
| 164 | 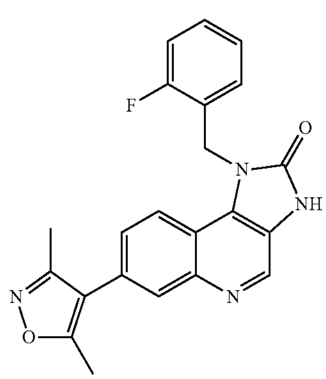 [SMILES: Cc1noc(C)c1-c1ccc2c(c1)ncc1[nH]c(=O)n(Cc3ccccc3F)c12] | 7-(3,5-dimethyl-4-isoxazolyl)-1-[(2-fluorophenyl)methyl]-1,3-dihydro-2H-imidazo[4,5-c]quinolin-2-one |

-continued

| Example | Structure | Name |
|---|---|---|
| 165 | 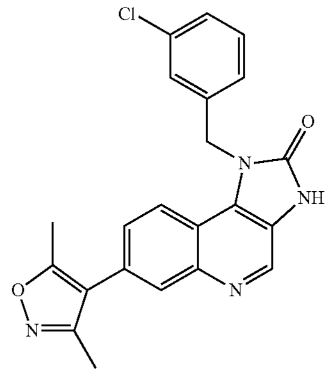 [SMILES: Cc1noc(C)c1-c1ccc2c(c1)ncc1[nH]c(=O)n(Cc3cccc(Cl)c3)c12] | 1-[(3-chlorophenyl)methyl]-7-(3,5-dimethyl-4-isoxazolyl)-1,3-dihydro-2H-imidazo[4,5-c]quinolin-2-one |
| 166 | 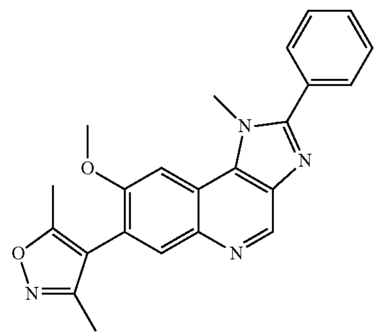 [SMILES: COc1cc2c(cc1-c1c(C)noc1C)ncc1nc(-c3ccccc3)n(C)c12] | 7-(3,5-dimethyl-4-isoxazolyl)-1-methyl-8-(methyloxy)-2-phenyl-1H-imidazo[4,5-c]quinoline |
| 167 | 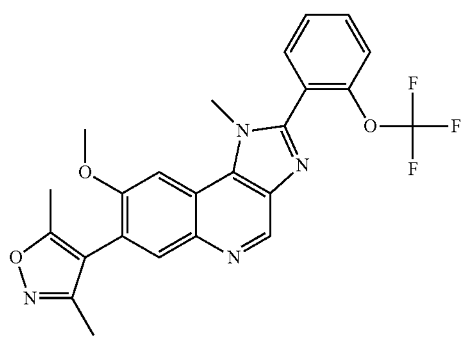 [SMILES: COc1cc2c(cc1-c1c(C)noc1C)ncc1nc(-c3ccccc3OC(F)(F)F)n(C)c12] | 7-(3,5-dimethyl-4-isoxazolyl)-1-methyl-8-(methyloxy)-2-{2-[(trifluoromethyl)oxy]phenyl}-1H-imidazo[4,5-c]quinoline |
| 168 | 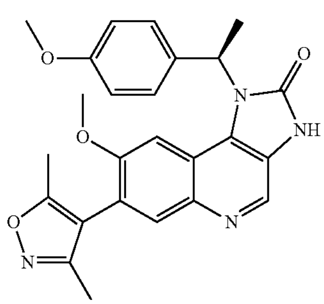 [SMILES: COc1ccc([C@@H](C)n2c(=O)[nH]c3cnc4cc(-c5c(C)noc5C)c(OC)cc4c32)cc1] | 7-(3,5-dimethyl-4-isoxazolyl)-8-(methyloxy)-1-{(1R)-1-[4-(methyloxy)phenyl]ethyl}-1,3-dihydro-2H-imidazo[4,5-c]quinolin-2-one |

| Example | Structure | Name |
|---|---|---|
| 169 | 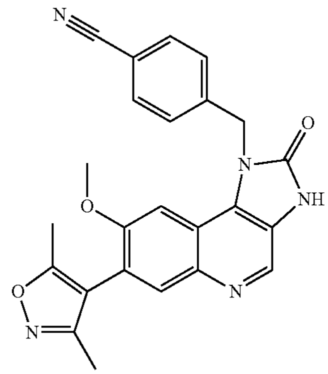 [SMILES: COc1cc2c(cc1-c1c(C)noc1C)ncc1[nH]c(=O)n(Cc3ccc(C#N)cc3)c12] | 4-{[7-(3,5-dimethyl-4-isoxazolyl)-8-(methyloxy)-2-oxo-2,3-dihydro-1H-imidazo[4,5-c]quinolin-1-yl]methyl}benzonitrile |
| 170 | 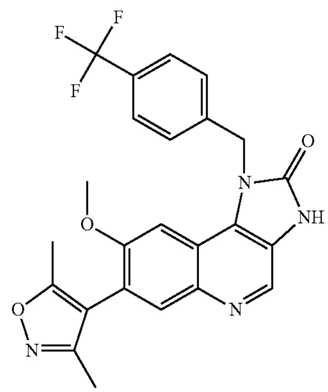 [SMILES: COc1cc2c(cc1-c1c(C)noc1C)ncc1[nH]c(=O)n(Cc3ccc(C(F)(F)F)cc3)c12] | 7-(3,5-dimethyl-4-isoxazolyl)-8-(methyloxy)-1-{[4-(trifluoromethyl)phenyl]methyl}-1,3-dihydro-2H-imidazo[4,5-c]quinolin-2-one |
| 171 | 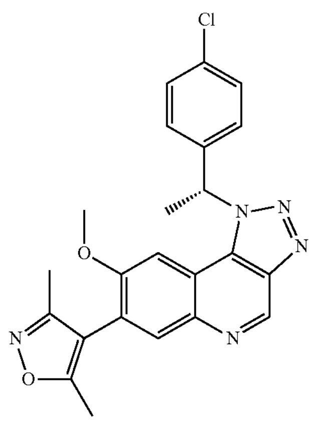 [SMILES: COc1cc2c(cc1-c1c(C)noc1C)ncc1nnn([C@H](C)c3ccc(Cl)cc3)c12] | 1-[(1R)-1-(4-chlorophenyl)ethyl]-7-(3,5-dimethyl-4-isoxazolyl)-8-(methyloxy)-1H-[1,2,3]triazolo[4,5-c]quinoline |
| 172 | 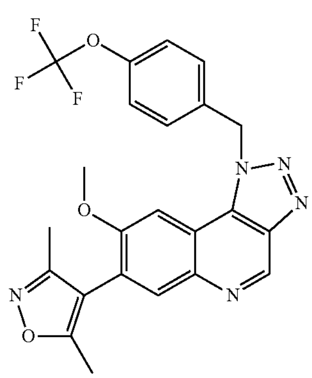 [SMILES: COc1cc2c(cc1-c1c(C)noc1C)ncc1nnn(Cc3ccc(OC(F)(F)F)cc3)c12] | 7-(3,5-dimethyl-4-isoxazolyl)-8-(methyloxy)-1-({4-[(trifluoromethyl)oxy]phenyl}methyl)-1H-[1,2,3]triazolo[4,5-c]quinoline |

-continued

| Example | Structure | Name |
| --- | --- | --- |
| 173 | 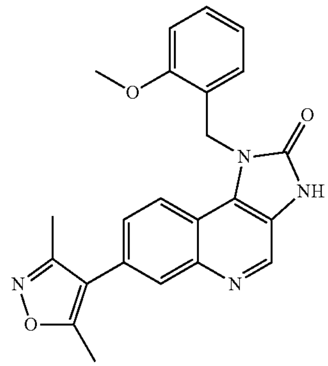 [SMILES: COc1ccccc1Cn1c(=O)[nH]c2cnc3cc(-c4c(C)noc4C)ccc3c21] | 7-(3,5-dimethyl-4-isoxazolyl)-1-{[2-(methyloxy)phenyl]methyl}-1,3-dihydro-2H-imidazo[4,5-c]quinolin-2-one |
| 174 | 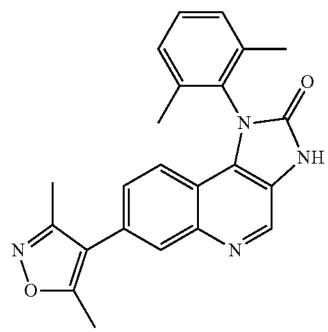 [SMILES: Cc1cccc(C)c1-n1c(=O)[nH]c2cnc3cc(-c4c(C)noc4C)ccc3c21] | 7-(3,5-dimethyl-4-isoxazolyl)-1-(2,6-dimethylphenyl)-1,3-dihydro-2H-imidazo[4,5-c]quinolin-2-one |
| 175 | 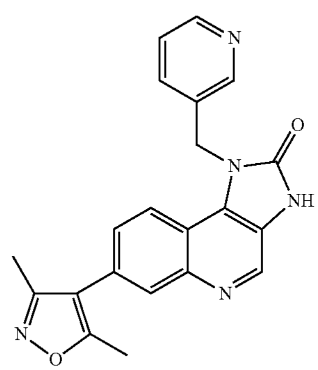 [SMILES: Cc1noc(C)c1-c1ccc2c(c1)ncc1[nH]c(=O)n(Cc3cccnc3)c12] | 7-(3,5-dimethyl-4-isoxazolyl)-1-(3-pyridinylmethyl)-1,3-dihydro-2H-imidazo[4,5-c]quinolin-2-one |
| 176 | 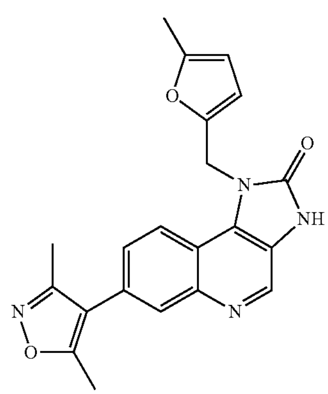 [SMILES: Cc1ccc(Cn2c(=O)[nH]c3cnc4cc(-c5c(C)noc5C)ccc4c32)o1] | 7-(3,5-dimethyl-4-isoxazolyl)-1-[(5-methyl-2-furanyl)methyl]-1,3-dihydro-2H-imidazo[4,5-c]quinolin-2-one |

-continued

| Example | Structure | Name |
|---|---|---|
| 177 | 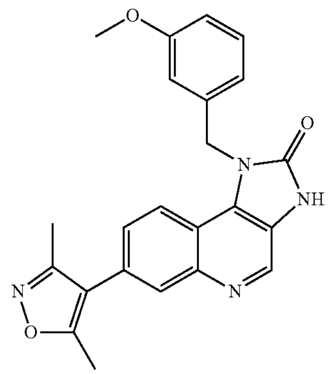 [SMILES: COc1cccc(Cn2c(=O)[nH]c3cnc4cc(-c5c(C)noc5C)ccc4c32)c1] | 7-(3,5-dimethyl-4-isoxazolyl)-1-{[3-(methyloxy)phenyl]methyl}-1,3-dihydro-2H-imidazo[4,5-c]quinolin-2-one |
| 178 | 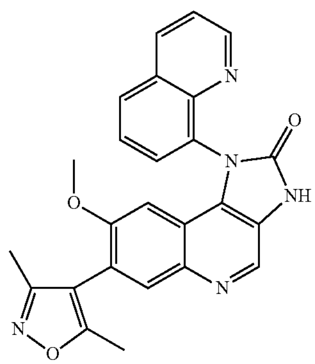 [SMILES: COc1cc2c(cc1-c1c(C)noc1C)ncc1[nH]c(=O)n(-c3cccc4cccnc34)c12] | 7-(3,5-dimethyl-4-isoxazolyl)-8-(methyloxy)-1-(8-quinolinyl)-1,3-dihydro-2H-imidazo[4,5-c]quinolin-2-one |
| 179 | 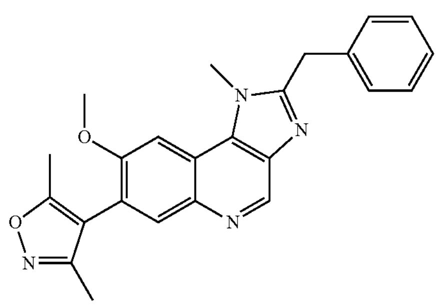 [SMILES: COc1cc2c(cc1-c1c(C)noc1C)ncc1nc(Cc3ccccc3)n(C)c12] | 7-(3,5-dimethyl-4-isoxazolyl)-1-methyl-8-(methyloxy)-2-(phenylmethyl)-1H-imidazo[4,5-c]quinoline |
| 180 | 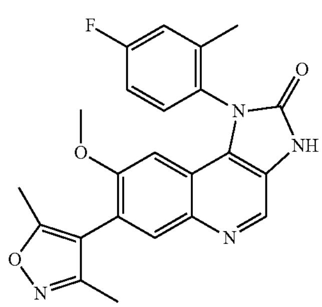 [SMILES: COc1cc2c(cc1-c1c(C)noc1C)ncc1[nH]c(=O)n(-c3ccc(F)cc3C)c12] | 7-(3,5-dimethyl-4-isoxazolyl)-1-(4-fluoro-2-methylphenyl)-8-(methyloxy)-1,3-dihydro-2H-imidazo[4,5-c]quinolin-2-one |

-continued

| Example | Structure | Name |
|---|---|---|
| 181 | 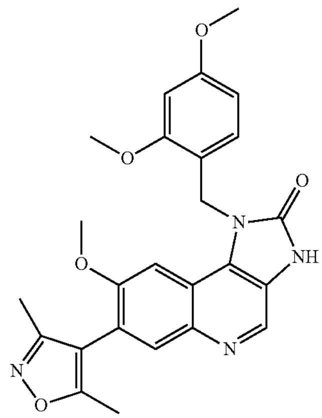 [SMILES: COc1ccc(Cn2c(=O)[nH]c3cnc4cc(-c5c(C)noc5C)c(OC)cc4c32)c(OC)c1] | 1-{[2,4-bis(methyloxy)phenyl]methyl}-7-(3,5-dimethyl-4-isoxazolyl)-8-(methyloxy)-1,3-dihydro-2H-imidazo[4,5-c]quinolin-2-one |
| 182 | 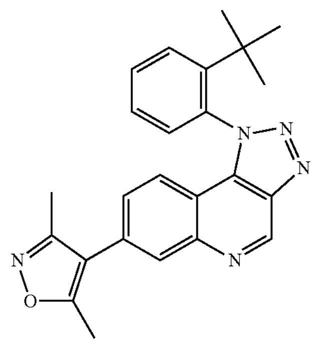 [SMILES: Cc1noc(C)c1-c1ccc2c(c1)ncc1nnn(-c3ccccc3C(C)(C)C)c12] | 1-[2-(1,1-dimethylethyl)phenyl]-7-(3,5-dimethyl-4-isoxazolyl)-1H-[1,2,3]triazolo[4,5-c]quinoline |
| 183 | 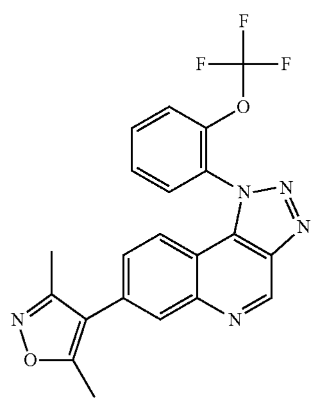 [SMILES: Cc1noc(C)c1-c1ccc2c(c1)ncc1nnn(-c3ccccc3OC(F)(F)F)c12] | 7-(3,5-dimethyl-4-isoxazolyl)-1-{2-[(trifluoromethyl)oxy]phenyl}-1H-[1,2,3]triazolo[4,5-c]quinoline |
| 184 | 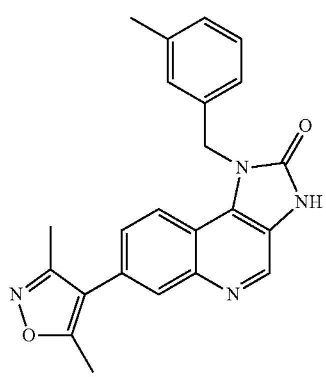 [SMILES: Cc1cccc(Cn2c(=O)[nH]c3cnc4cc(-c5c(C)noc5C)ccc4c32)c1] | 7-(3,5-dimethyl-4-isoxazolyl)-1-[(3-methylphenyl)methyl]-1,3-dihydro-2H-imidazo[4,5-c]quinolin-2-one |

-continued

| Example | Structure | Name |
|---|---|---|
| 185 | 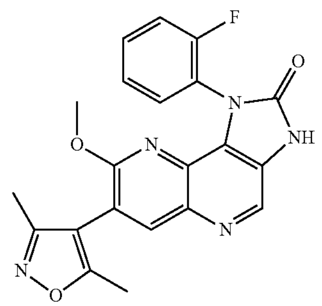 [SMILES: COc1nc2c(cc1-c1c(C)noc1C)ncc1[nH]c(=O)n(-c3ccccc3F)c12] | 7-(3,5-dimethyl-4-isoxazolyl)-1-(2-fluorophenyl)-8-(methyloxy)-1,3-dihydro-2H-imidazo[4,5-c]-1,5-naphthyridin-2-one |
| 186 | 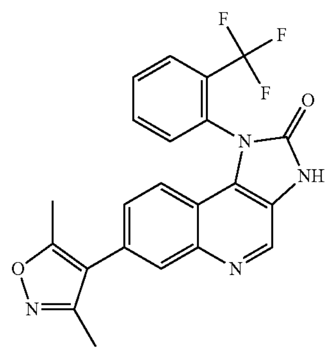 [SMILES: Cc1noc(C)c1-c1ccc2c(c1)ncc1[nH]c(=O)n(-c3ccccc3C(F)(F)F)c12] | 7-(3,5-dimethyl-4-isoxazolyl)-1-[2-(trifluoromethyl)phenyl]-1,3-dihydro-2H-imidazo[4,5-c]quinolin-2-one |
| 187 | 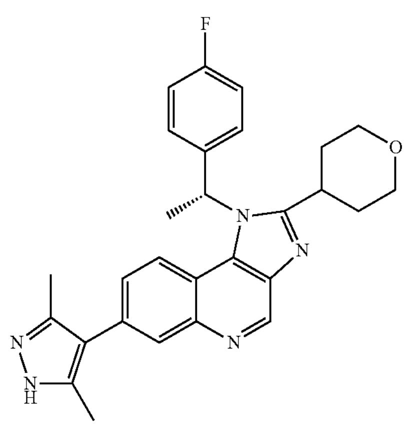 [SMILES: Cc1n[nH]c(C)c1-c1ccc2c(c1)ncc1nc(C3CCOCC3)n([C@H](C)c3ccc(F)cc3)c12] | 7-(3,5-dimethyl-1H-pyrazol-4-yl)-1-[(1R)-1-(4-fluorophenyl)ethyl]-2-(tetrahydro-2H-pyran-4-yl)-1H-imidazo[4,5-c]quinoline |
| 188 | 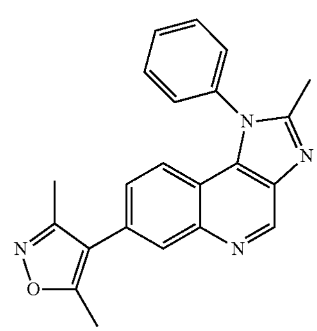 [SMILES: Cc1noc(C)c1-c1ccc2c(c1)ncc1nc(C)n(-c3ccccc3)c12] | 7-(3,5-dimethyl-4-isoxazolyl)-2-methyl-1-phenyl-1H-imidazo[4,5-c]quinoline |

-continued

| Example | Structure | Name |
|---|---|---|
| 189 | 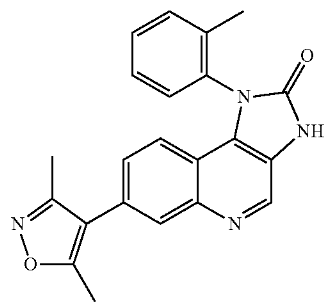 [SMILES: Cc1ccccc1-n1c(=O)[nH]c2cnc3cc(-c4c(C)noc4C)ccc3c21] | 7-(3,5-dimethyl-4-isoxazolyl)-1-(2-methylphenyl)-1,3-dihydro-2H-imidazo[4,5-c]quinolin-2-one |
| 190 | 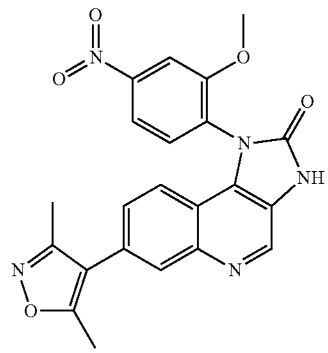 [SMILES: COc1cc([N+](=O)[O-])ccc1-n1c(=O)[nH]c2cnc3cc(-c4c(C)noc4C)ccc3c21] | 7-(3,5-dimethyl-4-isoxazolyl)-1-[2-(methyloxy)-4-nitrophenyl]-1,3-dihydro-2H-imidazo[4,5-c]quinolin-2-one |
| 191 | 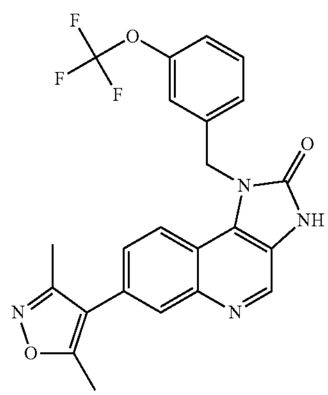 [SMILES: Cc1noc(C)c1-c1ccc2c(c1)ncc1[nH]c(=O)n(Cc3cccc(OC(F)(F)F)c3)c12] | 7-(3,5-dimethyl-4-isoxazolyl)-1-({3-[(trifluoromethyl)oxy]phenyl}methyl)-1,3-dihydro-2H-imidazo[4,5-c]quinolin-2-one |
| 192 | 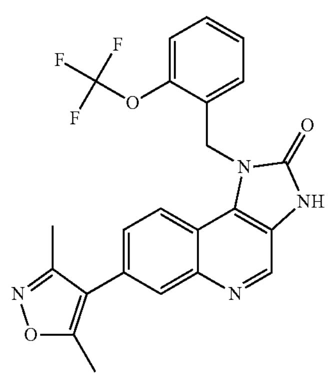 [SMILES: Cc1noc(C)c1-c1ccc2c(c1)ncc1[nH]c(=O)n(Cc3ccccc3OC(F)(F)F)c12] | 7-(3,5-dimethyl-4-isoxazolyl)-1-({2-[(trifluoromethyl)oxy]phenyl}methyl)-1,3-dihydro-2H-imidazo[4,5-c]quinolin-2-one |

-continued

| Example | Structure | Name |
|---|---|---|
| 193 | 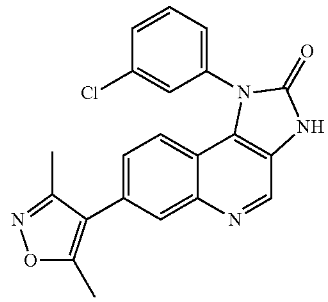 [SMILES: Cc1noc(C)c1-c1ccc2c(c1)ncc1[nH]c(=O)n(-c3cccc(Cl)c3)c12] | 1-(3-chlorophenyl)-7-(3,5-dimethyl-4-isoxazolyl)-1,3-dihydro-2H-imidazo[4,5-c]quinolin-2-one |
| 194 | 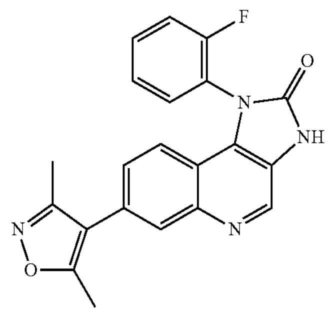 [SMILES: Cc1noc(C)c1-c1ccc2c(c1)ncc1[nH]c(=O)n(-c3ccccc3F)c12] | 7-(3,5-dimethyl-4-isoxazolyl)-1-(2-fluorophenyl)-1,3-dihydro-2H-imidazo[4,5-c]quinolin-2-one |
| 195 | 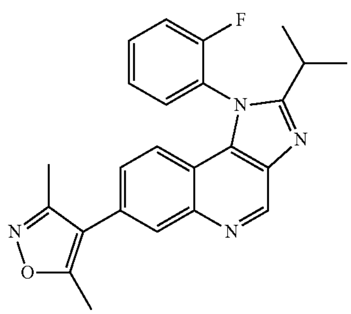 [SMILES: Cc1noc(C)c1-c1ccc2c(c1)ncc1nc(C(C)C)n(-c3ccccc3F)c12] | 7-(3,5-dimethyl-4-isoxazolyl)-1-(2-fluorophenyl)-2-(1-methylethyl)-1H-imidazo[4,5-c]quinoline |
| 196 | 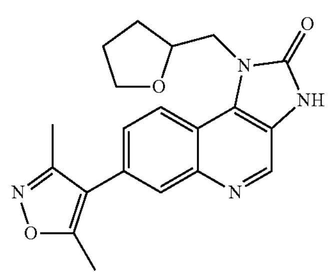 [SMILES: Cc1noc(C)c1-c1ccc2c(c1)ncc1[nH]c(=O)n(CC3CCCO3)c12] | 7-(3,5-dimethyl-4-isoxazolyl)-1-(tetrahydro-2-furanylmethyl)-1,3-dihydro-2H-imidazo[4,5-c]quinolin-2-one |
| 197 | 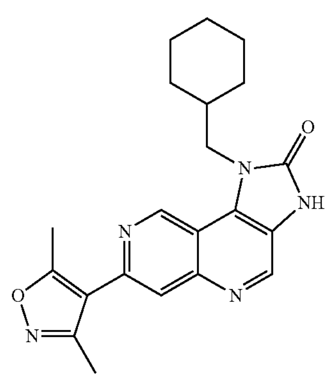 [SMILES: Cc1noc(C)c1-c1cc2ncc3[nH]c(=O)n(CC4CCCCC4)c3c2cn1] | 1-(cyclohexylmethyl)-7-(3,5-dimethyl-4-isoxazolyl)-1,3-dihydro-2H-imidazo[4,5-c]-1,6-naphthyridin-2-one |

-continued

| Example | Structure | Name |
|---|---|---|
| 198 | 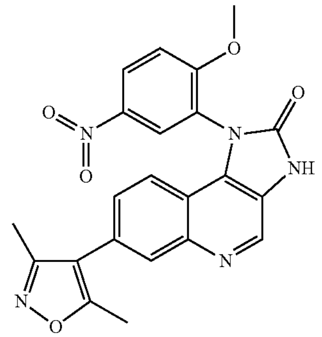 [SMILES: COc1ccc([N+](=O)[O-])cc1-n1c(=O)[nH]c2cnc3cc(-c4c(C)noc4C)ccc3c21] | 7-(3,5-dimethyl-4-isoxazolyl)-1-[2-(methyloxy)-5-nitrophenyl]-1,3-dihydro-2H-imidazo[4,5-c]quinolin-2-one |
| 199 | 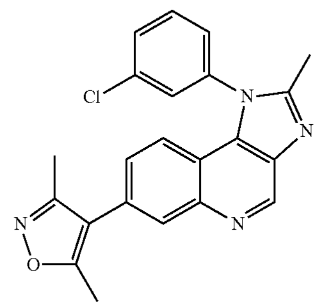 [SMILES: Cc1noc(C)c1-c1ccc2c(c1)ncc1nc(C)n(-c3cccc(Cl)c3)c12] | 1-(3-chlorophenyl)-7-(3,5-dimethyl-4-isoxazolyl)-2-methyl-1H-imidazo[4,5-c]quinoline |
| 200 | 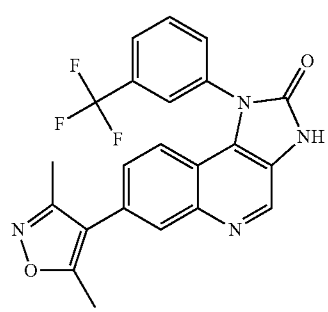 [SMILES: Cc1noc(C)c1-c1ccc2c(c1)ncc1[nH]c(=O)n(-c3cccc(C(F)(F)F)c3)c12] | 7-(3,5-dimethyl-4-isoxazolyl)-1-{[2-(trifluoromethyl)phenyl]methyl}-1,3-dihydro-2H-imidazo[4,5-c]quinolin-2-one |
| 201 | 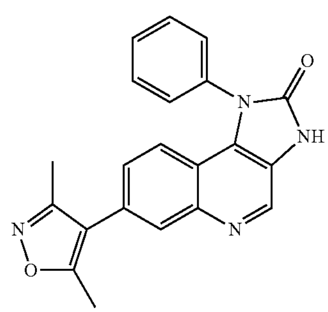 [SMILES: Cc1noc(C)c1-c1ccc2c(c1)ncc1[nH]c(=O)n(-c3ccccc3)c12] | 7-(3,5-dimethyl-4-isoxazolyl)-1-phenyl-1,3-dihydro-2H-imidazo[4,5-c]quinolin-2-one |
| 202 | 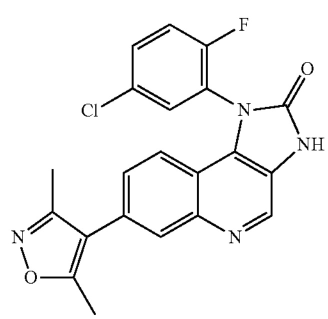 [SMILES: Cc1noc(C)c1-c1ccc2c(c1)ncc1[nH]c(=O)n(-c3cc(Cl)ccc3F)c12] | 1-(5-chloro-2-fluorophenyl)-7-(3,5-dimethyl-4-isoxazolyl)-1,3-dihydro-2H-imidazo[4,5-c]quinolin-2-one |

-continued

| Example | Structure | Name |
|---|---|---|
| 203 | 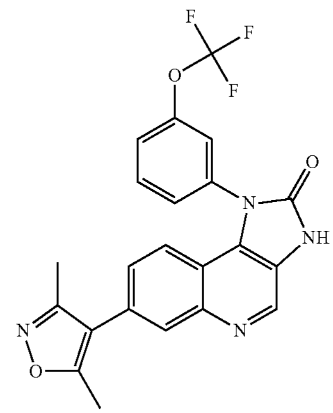 [SMILES: Cc1noc(C)c1-c1ccc2c(c1)ncc1[nH]c(=O)n(-c3cccc(OC(F)(F)F)c3)c12] | 7-(3,5-dimethyl-4-isoxazolyl)-1-{3-[(trifluoromethyl)oxy]phenyl}-1,3-dihydro-2H-imidazo[4,5-c]quinolin-2-one |
| 204 | 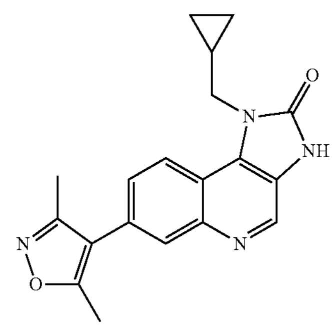 [SMILES: Cc1noc(C)c1-c1ccc2c(c1)ncc1[nH]c(=O)n(CC3CC3)c12] | 1-(cyclopropylmethyl)-7-(3,5-dimethyl-4-isoxazolyl)-1,3-dihydro-2H-imidazo[4,5-c]quinolin-2-one |
| 205 | 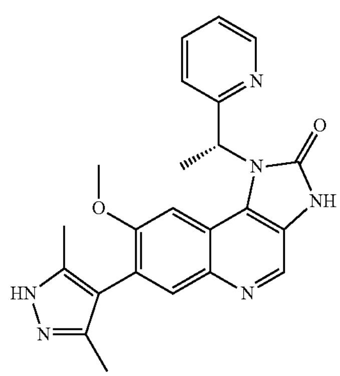 [SMILES: COc1cc2c(cc1-c1c(C)n[nH]c1C)ncc1[nH]c(=O)n([C@H](C)c3ccccn3)c12] | 7-(3,5-dimethyl-1H-pyrazol-4-yl)-8-(methyloxy)-1-[(1R)-1-(2-pyridinyl)ethyl]-1,3-dihydro-2H-imidazo[4,5-c]quinolin-2-one |
| 206 | 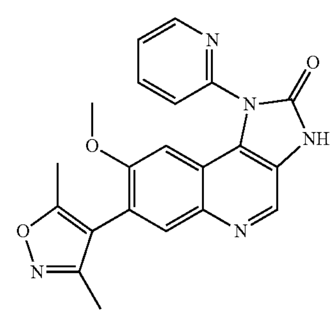 [SMILES: COc1cc2c(cc1-c1c(C)noc1C)ncc1[nH]c(=O)n(-c3ccccn3)c12] | 7-(3,5-dimethyl-4-isoxazolyl)-8-(methoxy)-1-(2-pyridinyl)-1,3-dihydro-2H-imidazo[4,5-c]quinolin-2-one |

-continued

| Example | Structure | Name |
|---|---|---|
| 207 | 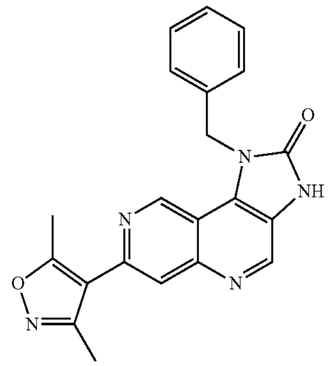 [SMILES: Cc1noc(C)c1-c1cc2ncc3[nH]c(=O)n(Cc4ccccc4)c3c2cn1] | 7-(3,5-dimethyl-4-isoxazolyl)-1-(phenylmethyl)-1,3-dihydro-2H-imidazo[4,5-c]-1,6-naphthyridin-2-one |
| 208 | 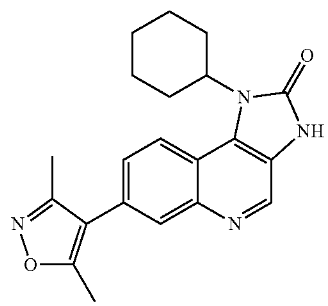 [SMILES: Cc1noc(C)c1-c1ccc2c(c1)ncc1[nH]c(=O)n(C3CCCCC3)c12] | 1-cyclohexyl-7-(3,5-dimethyl-4-isoxazolyl)-1,3-dihydro-2H-imidazo[4,5-c]quinolin-2-one |
| 209 | 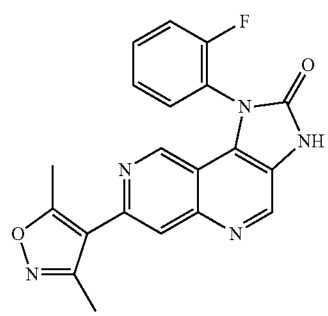 [SMILES: Cc1noc(C)c1-c1cc2ncc3[nH]c(=O)n(-c4ccccc4F)c3c2cn1] | 7-(3,5-dimethyl-4-isoxazolyl)-1-(2-fluorophenyl)-1,3-dihydro-2H-imidazo[4,5-c]-1,6-naphthyridin-2-one |
| 210 | 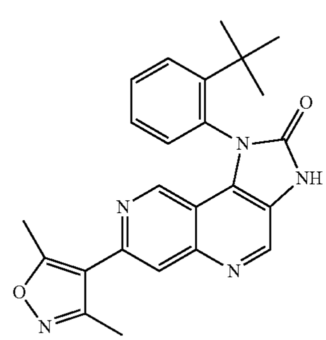 [SMILES: Cc1noc(C)c1-c1cc2ncc3[nH]c(=O)n(-c4ccccc4C(C)(C)C)c3c2cn1] | 1-[2-(1,1-dimethylethyl)phenyl]-7-(3,5-dimethyl-4-isoxazolyl)-1,3-dihydro-2H-imidazo[4,5-c]-1,6-naphthyridin-2-one |

-continued

| Example | Structure | Name |
|---|---|---|
| 211 | 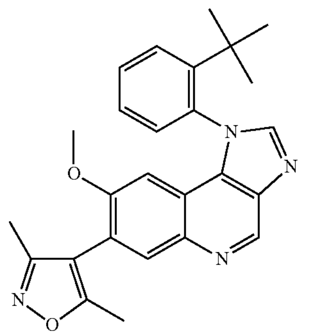 [SMILES: COc1cc2c(cc1-c1c(C)noc1C)ncc1ncn(-c3ccccc3C(C)(C)C)c12] | 1-[2-(1,1-dimethylethyl)phenyl]-7-(3,5-dimethyl-4-isoxazolyl)-8-(methyloxy)-1H-imidazo[4,5-c]quinoline |
| 212 | 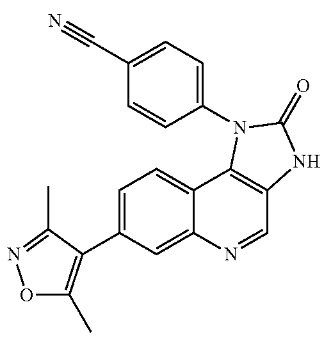 [SMILES: Cc1noc(C)c1-c1ccc2c(c1)ncc1[nH]c(=O)n(-c3ccc(C#N)cc3)c12] | 4-[7-(3,5-dimethyl-4-isoxazolyl)-2-oxo-2,3-dihydro-1H-imidazo[4,5-c]quinolin-1-yl]benzonitrile |
| 213 | 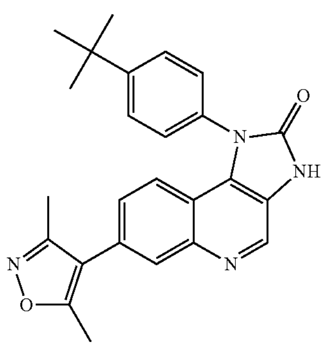 [SMILES: Cc1noc(C)c1-c1ccc2c(c1)ncc1[nH]c(=O)n(-c3ccc(C(C)(C)C)cc3)c12] | 1-[4-(1,1-dimethylethyl)phenyl]-7-(3,5-dimethyl-4-isoxazolyl)-1,3-dihydro-2H-imidazo[4,5-c]quinolin-2-one |
| 214 | 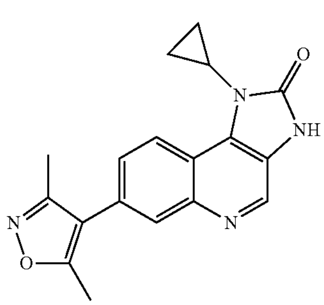 [SMILES: Cc1noc(C)c1-c1ccc2c(c1)ncc1[nH]c(=O)n(C3CC3)c12] | 1-cyclopropyl-7-(3,5-dimethyl-4-isoxazolyl)-1,3-dihydro-2H-imidazo[4,5-c]quinolin-2-one |

-continued

| Example | Structure | Name |
|---|---|---|
| 215 | 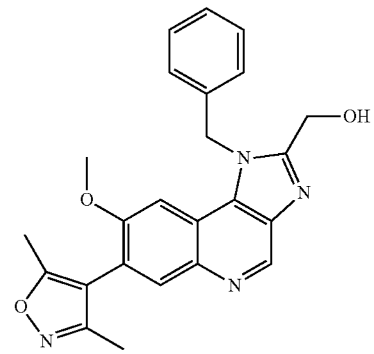 [SMILES: COc1cc2c(cc1-c1c(C)noc1C)ncc1nc(CO)n(Cc3ccccc3)c12] | [7-(3,5-dimethyl-4-isoxazolyl)-8-(methyloxy)-1-(phenylmethyl)-1H-imidazo[4,5-c]quinolin-2-yl]methanol |
| 216 | 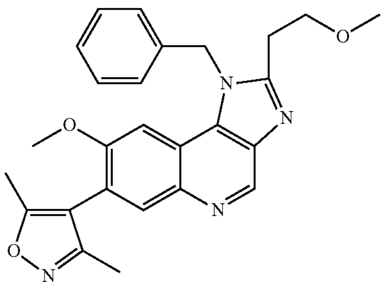 | [7-(3,5-dimethyl-4-isoxazolyl)-8-(methyloxy)-2-[2-(methyloxy)ethyl]-1-(phenylmethyl)-1H-imidazo[4,5-c]quinoline |
| 217 | 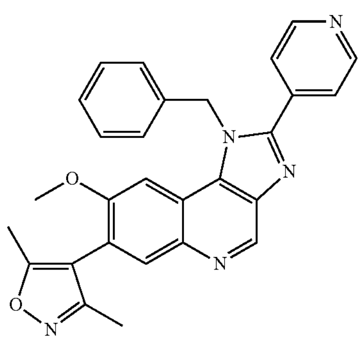 [SMILES: COc1cc2c(cc1-c1c(C)noc1C)ncc1nc(-c3ccncc3)n(Cc3ccccc3)c12] | 7-(3,5-dimethyl-4-isoxazolyl)-8-(methyloxy)-1-(phenylmethyl)-2-(4-pyridinyl)-1H-imidazo[4,5-c]quinoline |
| 218 | 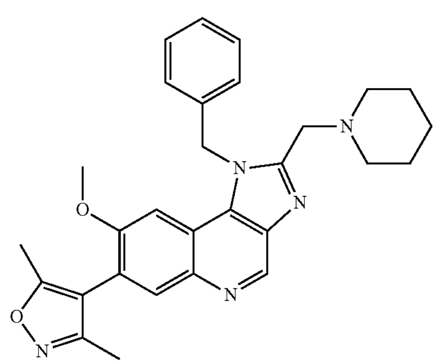 [SMILES: COc1cc2c(cc1-c1c(C)noc1C)ncc1nc(CN3CCCCC3)n(Cc3ccccc3)c12] | 7-(3,5-dimethyl-4-isoxazolyl)-8-(methyloxy)-1-(phenylmethyl)-2-(1-piperidinylmethyl)-1H-imidazo[4,5-c]quinoline |

-continued

| Example | Structure | Name |
|---|---|---|
| 219 | 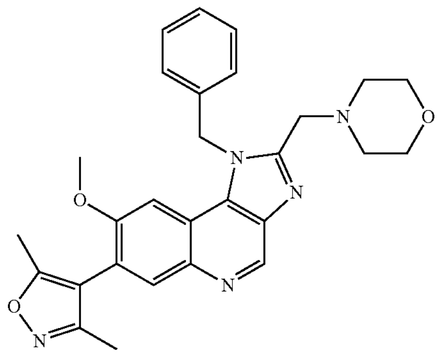 [SMILES: COc1cc2c(cc1-c1c(C)noc1C)ncc1nc(CN3CCOCC3)n(Cc3ccccc3)c12] | 7-(3,5-dimethyl-4-isoxazolyl)-8-(methyloxy)-2-(4-morpholinylmethyl)-1-(phenylmethyl)-1H-imidazo[4,5-c]quinoline |
| 220 | 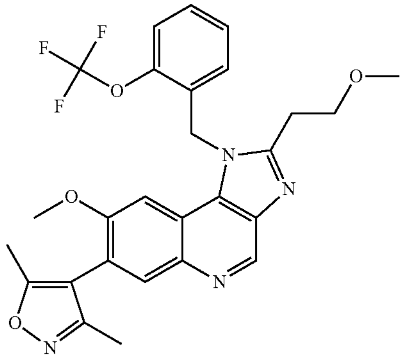 | 7-(3,5-dimethyl-4-isoxazolyl)-8-(methyloxy)-2-[2-(methyloxy)ethyl]-1-{2-[(trifluoromethyl)oxy]phenyl}-1H-imidazo[4,5-c]quinoline |
| 221 | 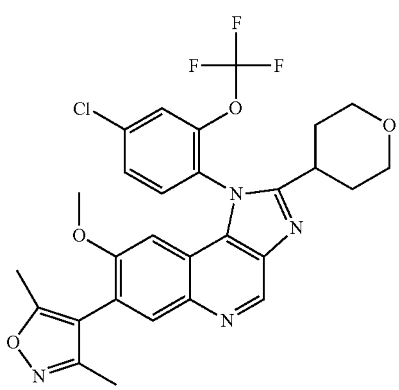 [SMILES: COc1cc2c(cc1-c1c(C)noc1C)ncc1nc(C3CCOCC3)n(-c3ccc(Cl)cc3OC(F)(F)F)c12] | 1-{4-chloro-2-[(trifluoromethyl)oxy]phenyl}-7-(3,5-dimethyl-4-isoxazolyl)-8-(methyloxy)-2-(tetrahydro-2H-pyran-4-yl)-1H-imidazo[4,5-c]quinoline |
| 222 | 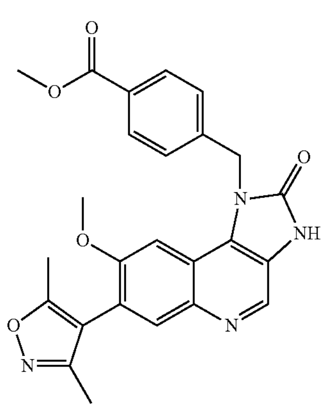 [SMILES: COC(=O)c1ccc(Cn2c(=O)[nH]c3cnc4cc(-c5c(C)noc5C)c(OC)cc4c32)cc1] | methyl 4-{[7-(3,5-dimethyl-4-isoxazolyl)-8-(methyloxy)-2-oxo-2,3-dihydro-1H-imidazo[4,5-c]quinolin-1-yl]methyl}benzoate |

-continued

| Example | Structure | Name |
|---|---|---|
| 223 | 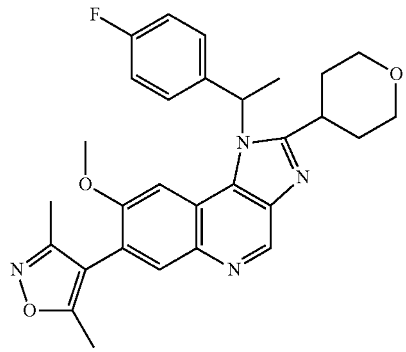 [SMILES: COc1cc2c(cc1-c1c(C)noc1C)ncc1nc(C3CCOCC3)n(C(C)c3ccc(F)cc3)c12] | 7-(3,5-dimethyl-4-isoxazolyl)-1-[1-(4-fluorophenyl)ethyl]-8-(methyloxy)-2-(tetrahydro-2H-pyran-4-yl)-1H-imidazo[4,5-c]quinoline |
| 224 | 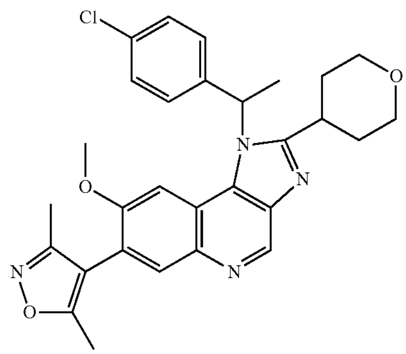 | 1-[1-(4-chlorophenyl)ethyl]-7-(3,5-dimethyl-4-isoxazolyl)-8-(methyloxy)-2-(tetrahydro-2H-pyran-4-yl)-1H-imidazo[4,5-c]quinoline |
| 225 | 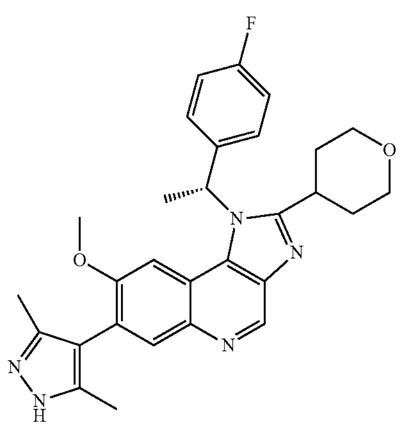 [SMILES: COc1cc2c(cc1-c1c(C)n[nH]c1C)ncc1nc(C3CCOCC3)n([C@H](C)c3ccc(F)cc3)c12] | 7-(3,5-dimethyl-1H-pyrazol-4-yl)-1-[(1R)-1-(4-fluorophenyl)ethyl]-8-(methyloxy)-2-(tetrahydro-2H-pyran-4-yl)-1H-imidazo[4,5-c]quinoline |
| 226 | 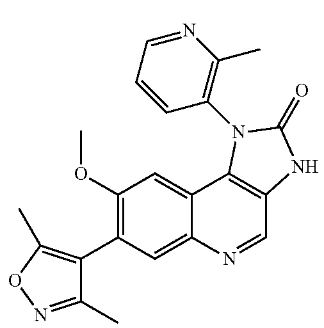 [SMILES: COc1cc2c(cc1-c1c(C)noc1C)ncc1[nH]c(=O)n(-c3cccnc3C)c12] | 7-(3,5-dimethyl-4-isoxazolyl)-8-(methyloxy)-1-(2-methyl-3-pyridinyl)-1,3-dihydro-2H-imidazo[4,5-c]quinolin-2-one |

Reference Compounds

Experimental details of LC-MS methods D and F as referred to in the Reference compounds below are as follows:

LC/MS (Method D) was conducted on a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]⁺ and [M+NH₄]⁺ molecular ions] or electrospray negative ionisation [(ES−ve to give [M−H]− molecular ion] modes. Analytical data from this apparatus are given with the following format: [M+H]⁺ or [M−H]⁻.

LC/MS (Method F) was conducted on an Sunfire C18 column (30 mm×4.6 mm i.d. 3.5 µm packing diameter) at 30 degrees centigrade, eluting with 0.1% v/v solution of trifluoroacetic acid in water (Solvent A) and 0.1% v/v solution of trifluoroacetic acid in acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/HRMS: Analytical HPLC was conducted on a Uptisphere-hsc column (3 µm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH⁺ molecular ions] or electrospray negative ionisation [ES−ve to give (M−H)− molecular ions] modes.

TLC (thin layer chromatography) refers to the use of TLC plates sold by Merck coated with silica gel 60 F254.

Reference Compound A:
2-methyl-6-(methyloxy)-4H-3,1-benzoxazin-4-one

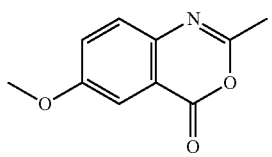

A solution of 5-methoxyanthranilic acid (Lancaster) (41.8 g, 0.25 mol) was refluxed in acetic anhydride (230 ml) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 [M+H]⁺, Rt 1.69 min.

Reference Compound B: [2-amino-5-(methyloxy)phenyl](4-chlorophenyl)methanone

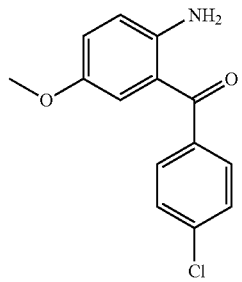 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 ml) at 0° C. was added dropwise a solution of 4-chlorophenylmagnesium bromide (170 ml, 1M in diethyl ether, 0.17 mol). The reaction mixture was allowed to warm to room temperature and stirred for 1 h before being quenched with 1N HCl (200 ml). The aqueous layer was extracted with EtOAc (3×150 ml) and the combined organics were washed with brine (100 ml), dried over Na₂SO₄, filtered and concentrated under reduced pressure. The crude compound was then dissolved in ethanol (400 ml) and 6N HCl (160 ml) was added. The reaction mixture was refluxed for 2 h before being concentrated to one-third in volume. The resulting solid was filtered and washed twice with ether before being suspended in EtOAc and neutralised with 1N sodium hydroxide. The aqueous layer was extracted with EtOAc (3×150 ml) and the combined organics were washed with brine (150 ml), dried over Na₂SO₄, filtered and concentrated under reduced pressure. The title compound was obtained as a yellow solid (39 g, 88% yield); LC/MS (Method D): m/z 262 [M+H]⁺, Rt 2.57 min.

Reference Compound C: Methyl N¹-[2-[(4-chlorophenyl)carbonyl]-4-(methyloxy)phenyl]-N²-{[(9H-fluoren-9-ylmethyl)oxy]carbonyl}-L-□-asparaginate

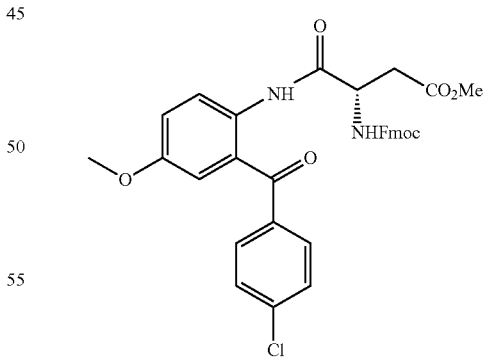

Methyl N-{[(9H-fluoren-9-ylmethyl)oxy]carbonyl}-L-α-aspartyl chloride (Int. J. Peptide Protein Res. 1992, 40, 13-18) (93 g, 0.24 mol) was dissolved in CHCl₃ (270 ml) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference Compound D: Methyl [(3S)-5-(4-chlorophenyl)-7-(methyloxy)-2-oxo-2,3-dihydro-1H-1,4-benzodiazepin-3-yl]acetate

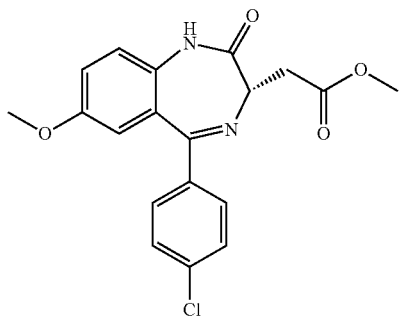

To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 ml) was added Et₃N (500 ml, 3.65 mol) and the resulting mixture was refluxed for 24 h before being concentrated. The resulting crude amine was dissolved in 1,2-DCE (1.5 L) and AcOH (104 ml, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na₂SO₄, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product $R_f$=0.34 (DCM/MeOH:95/5).
HRMS MH+ calculated for $C_{19}H_{18}{}^{35}ClN_2O_4$ 373.0955; found 373.0957.

Reference Compound E: Methyl [(3S)-5-(4-chlorophenyl)-7-(methyloxy)-2-thioxo-2,3-dihydro-1H-1,4-benzodiazepin-3-yl]acetate

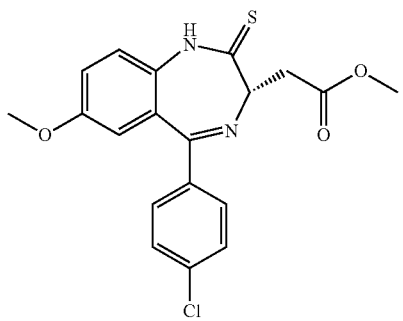

A suspension of $P_4S_{10}$ (36.1 g, 81.1 mmol) and $Na_2CO_3$ (8.6 g, 81.1 mmol) in 1,2-DCE (700 ml) at room temperature was stirred for 2 h before methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. Sodium hydrogen carbonate and brine. The organic layer was dried over Na₂SO₄, filtered and concentrated under reduced pressure. The crude product was purified by flash-chromatography on silica gel (DOM/MeOH: 99/1) to afford the title compound (17.2 g, 98% yield) as a yellowish solid.
LC/MS (Method D): m/z 389 [M(³⁵Cl)+H]⁺, Rt 2.64 min
HRMS MH+calculated for $C_{19}H_{18}{}^{35}ClN_2O_3S$ 389.0727; found 389.0714.

Reference Compound F: Methyl [(3S)-2-[(1Z)-2-acetylhydrazino]-5-(4-chlorophenyl)-7-(methyloxy)-3H-1,4-benzodiazepin-3-yl]acetate

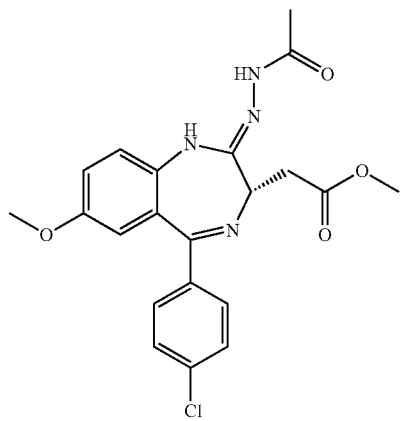

To a suspension of methyl [(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 ml) at 0° C. was added hydrazine monohydrate (3.4 ml, 69.6 mmol) dropwise. The reaction mixture was stirred for 5 h between 5° C. and 15° C. before being cooled at 0° C. Et₃N (9.7 ml, 69.6 mmol) was then added slowly and acetyl chloride (7.95 ml, 69.6 mmol) was added dropwise. The mixture was then allowed to warm to room temperature for 16 h before being concentrated under reduced pressure. The crude product was dissolved in DCM and washed with water. The organic layer was dried over Na₂SO₄, filtered and concentrated in vacuo to give the crude title compound (9.7 g, 98% yield) which was used without further purification. $R_f$=0.49 (DCM/MeOH:90/10).

Reference Compound G: Methyl [(4S)-6-(4-chlorophenyl)-1-methyl-8-(methyloxy)-4H-[1,2,4]triazolo[4,3-a][1,4]benzodiazepin-4-yl]acetate

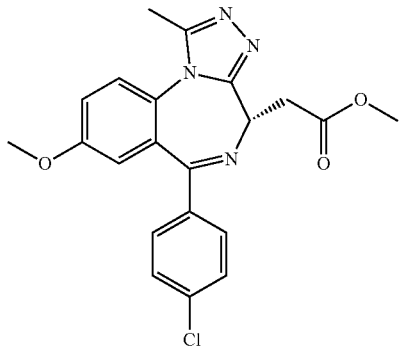

The crude methyl [(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 ml) was added at room temperature. The reaction mixture was stirred at this temperature for 2 days before being concentrated under reduced pressure. The crude solid was triturated in i-Pr₂O and filtered to give the title compound (8.7 g, 91% over 3 steps) as an off-white solid.

HRMS MH+calculated for $C_{21}H_{20}ClN_4O_3$ 411.1229; found 411.1245.

Reference Compound H: [(4S)-6-(4-Chlorophenyl)-1-methyl-8-(methyloxy)-4H-[1,2,4]triazolo[4,3-a][1,4]benzodiazepin-4-yl]acetic acid

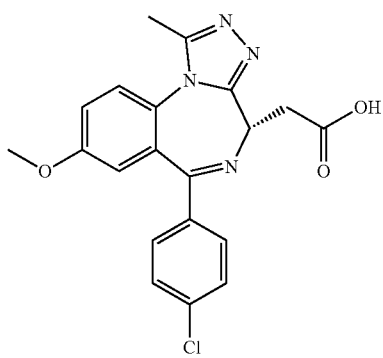 [SMILES: COc1ccc2c(c1)C(c1ccc(Cl)cc1)=N[C@@H](CC(=O)O)c1nnc(C)n1-2]

To a solution of methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 ml) at room temperature was added 1N sodium hydroxide (36.2 ml, 36.2 mmol). The reaction mixture was stirred at this temperature for 5 h before being quenched with 1N HCl (36.2 ml) and concentrated in vacuo. Water is then added and the aqueous layer was extracted with DCM (×3) and the combined organic layers were dried over Na₂SO₄, filtered and concentrated under reduced pressure to give the title compound (7 g, 98% yield) as a pale yellow solid.

Reference Compound H: 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

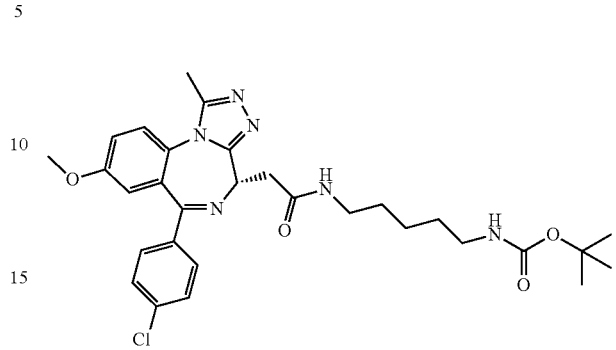

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound G) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference Compound J: N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

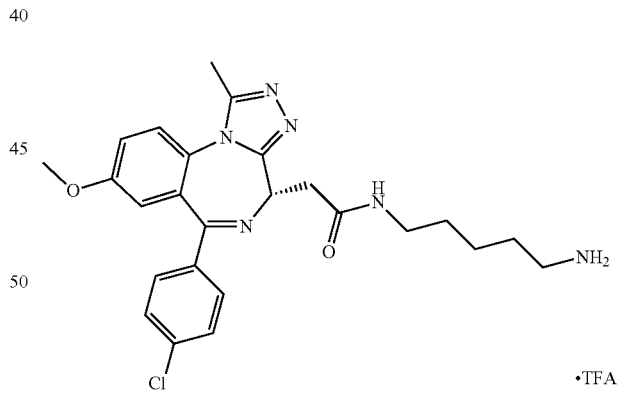

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound H) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS MH+calculated for $C_{25}H_{29}ClN_6O_2$ 481.2119; found 481.2162.

Reference Compound K: Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

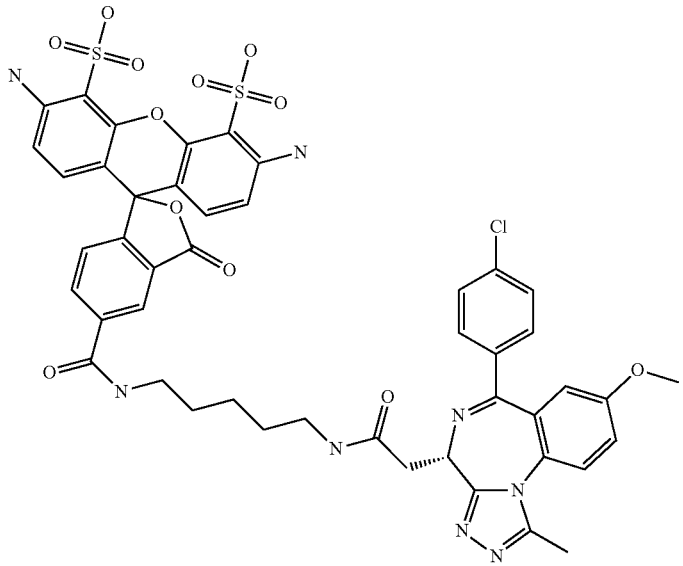

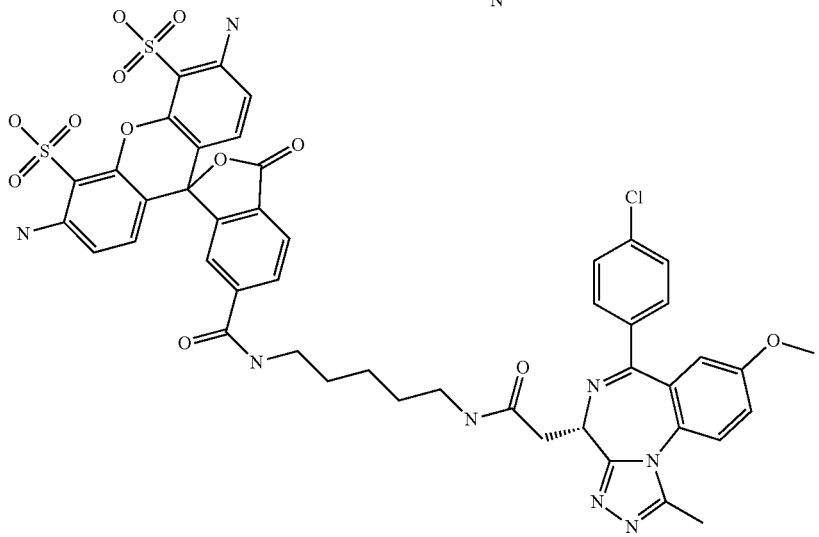

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown.

LC/MS (Method F): MH+=999, rt=1.88 min.

Biological Test Methods

Fluorescence Anisotropy Binding Assay

The binding of the compounds of formula (I) to Bromodomain BRD2, BRD3 and BRD4 was assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y=a+((b-a)/(1+(10\char`\^x/10\char`\^c)\char`\^d))$$

Where 'a' is the minimum, 'b' is the Hill slope, 'c' is the $pIC_{50}$ and 'd' is the maximum.

Recombinant Human Bromodomains (Bromodomain BRD2 (1-473), Bromodomain BRD3 (1-435) and Bromodomain BRD4 (1-477)) were expressed in *E. coli* cells (in pET 15b vector) with a six-His tag at the N-terminal. The His-tagged Bromodomain was extracted from *E. coli* cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80° C. in 20 mM HEPES pH 7.5 and 100 mM NaCl.

Protocol for Bromodomain BRD2:

All components were dissolved in buffer composition of 50 mM HEPES pH7.4, 150 mm NaCl and 0.5 mM CHAPS with final concentrations of Bromodomain 2, 75 nM, fluorescent ligand SnM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD3:

All components were dissolved in buffer of composition 50 mM HEPES pH7.4, 150 mm NaCl and 0.5 mM CHAPS with final concentrations of Bromodomains 3 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD4:

All components were dissolved in buffer of composition 50 mM HEPES pH7.4, 150 mm NaCl and 0.5 mM CHAPS with final concentrations of Bromodomain 4 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

All examples (with the exception of examples 22, 38 and 210-225) were tested in the assays described above. All tested compounds had a $pIC_{50} \geq 5.0$ in one or more of the BRD2, BRD3 and BRD4 assays described above. Examples 1, 3-8, 10-21, 23-31, 33-37, 39-43, 45-61, 63-158, 160, 162-170, 172, 173, 176-181, 183-185 and 187 had a $pIC_{50} \geq 6.0$ in one or more of the BRD2, BRD3 and BRD4 assays described above.

LPS Stimulated Whole Blood Measuring TNFα Levels Assay

Activation of monocytic cells by agonists of toll-like receptors such as bacterial lipopolysaccharide (LPS) results in production of key inflammatory mediators including TNFα. Such pathways are widely considered to be central to the pathophysiology of a range of auto-immune and inflammatory disorders.

Compounds to be tested are diluted to give a range of appropriate concentrations and 1 ul of the dilution stocks is added to wells of a 96 plate. Following addition of whole blood (130 ul) the plates are incubated at 37 degrees (5% $CO_2$) for 30 min before the addition of 10 ul of 2.8 ug/ml LPS, diluted in complete RPMI 1640 (final concentration=200 ng/ml), to give a total volume of 140 ul per well. After further incubation for 24 h at 37 degrees, 140 ul of PBS are added to each well. The plates are sealed, shaken for 10 minutes and then centrifuged (2500 rpm×10 min). 100 ul of the supernatant are removed and TNFα levels assayed by immunoassay (typically by MesoScale Discovery technology) either immediately or following storage at −20 degrees. Dose response curves for each compound was generated from the data and an $IC_{50}$ value was calculated.

Examples 11, 12, 15, 27, 31, 33, 36, 108 and 126 were tested in the above assay were found to have a $pIC_{50} \geq 5.5$.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 ul of the diluted stocks is added to a 96 well plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and IL-6 levels assayed by immunoassay (typically by MesoScale Discovery technology) either immediately or following storage at −20 degrees. Concentration response curves for each compound was generated from the data and an $IC_{50}$ value was calculated Examples 11, 36-37, 39-40, 45 and 51 were tested in the above assay were found to have a $pIC_{50} \geq 5.5$.

These data demonstrate that bromodomain inhibitors tested in the above two whole blood assays inhibited the production of key inflammatory mediators TNFα and/or IL-6.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds for use in the invention groups of eight Balb/c male mice were given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals was monitored at 4 days.

Numbers of animals surviving at 4 days (summed across multiple repeat experiments)

| | |
|---|---|
| Vehicle | 4/66 (6%) |
| Compound of Example 11 | 55/66 (83%) |
| Compound of Example 31 | 9/24 (38%) |

These data demonstrate that the bromodomain inhibitors teated in the above model gave rise to a significant animal survival effect following intravenous administration.

Oncology Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (T0) measurement and compound (20 point titration from 14.7 uM to 7 pM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results were expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin-T0 value is determined by subtracting the T0 value (100%) from the Ymin value (%) determined from the fit of the concentration response curve. Values from the wells with no cells were subtracted from all samples for background correction.

The compound of Examples 11 and 36 was tested in accordance with the above assay and found to have a $gIC_{50}$ in the range 118-11100 nM across all cell lines, more specifically in the range 118-1036 nM for heme cell lines and 432-11100 nM for breast cell lines.

These data demonstrate that the bromodomain inhibitor tested in the above assay inhibited cell growth in a panel of oncology cell lines.

All publications, including but not limited to patents and patent applications, cited in this specification are herein incorporated by reference as if each individual publication were specifically and individually indicated to be incorporated by reference herein as though fully set forth.

What is claimed is:

1. A compound of formula (I) or a salt thereof

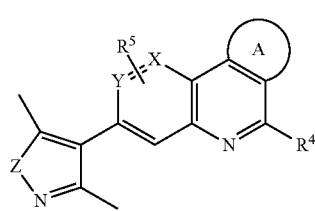

(I)

wherein:
A is a group selected from the following:

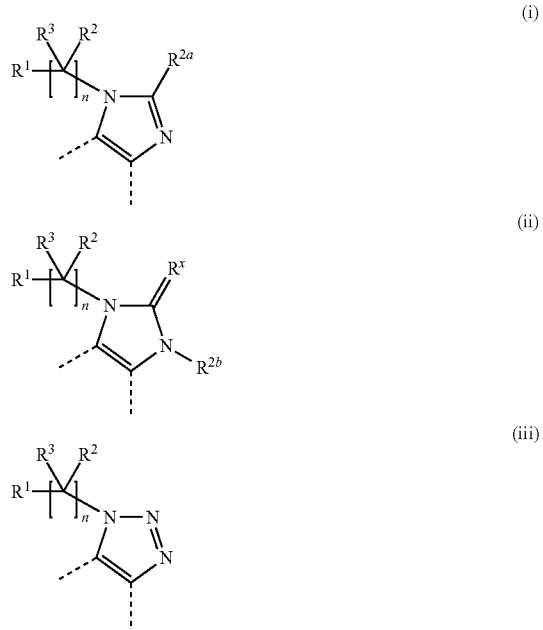

X represents CH or N;
Y represents CH or N with the proviso that when X is N, Y is CH;
$R^x$ represents O or S;
$R^1$ represents $C_{1-6}$alkyl, $C_{3-6}$cycloalkyl, a 5 or 6 membered heterocyclyl, an aromatic group or a heteroaromatic group, wherein the aromatic group or the heteroaromatic group is optionally substituted by one to three groups selected from:
  halogen, hydroxy, cyano, nitro, $C_{1-6}$alkyl, $C_{1-4}$alkoxy, halo$C_{1-4}$alkyl, halo$C_{1-4}$-alkoxy, hydroxy$C_{1-4}$alkyl, $C_{1-4}$-alkoxy$C_{1-4}$alkyl, $C_{1-4}$-alkoxycarbonyl, $C_{1-4}$-alkylsulfonyl, $C_{1-4}$-alkylsulfonyloxy, $C_{1-4}$alkylsulfonyl$C_{1-4}$alkyl, $C_{1-4}$-alkylsulfonamido;
$R^2$ is hydrogen or $C_{1-6}$alkyl,
$R^{2a}$ represents:
  H, $C_{1-6}$alkyl, $C_{1-6}$haloallyl, $(CH_2)_m$cyano, $(CH_2)_m$OH, $(CH_2)_m C_{1-6}$alkoxy, $(CH_2)_m C_{1-6}$haloalkoxy, $(CH_2)_m C_{1-6}$haloalkyl $(CH_2)_m C(O)NR^aR^b$, $(CH_2)_m NR^aR^b$ and $(CH_2)_m C(O)CH_3$,
  $(CHR^6)_p$phenyl optionally substituted by $C_{1-6}$alkyl, $C_{1-6}$alkoxy, cyano halo$C_{1-4}$-alkoxy, halo$C_{1-4}$-alkyl,
  $(CHR^6)_p$heteroaromatic, $(CHR^6)_p$heterocyclyl, wherein
    $R^a$ represents H, $C_{1-6}$alkyl, or heterocyclyl;
    $R^b$ represents H or $C_{1-6}$alkyl, or
    $R^a$ and $R^b$ together with the N to which they are attached form a 5 or 6 membered heterocyclyl;
$R^{2b}$ represents H, $C_{1-6}$alkyl, $(CH_2)_2 C_{1-6}$alkoxy, $(CH_2)_2$cyano, $(CH_2)_m$phenyl, $(CH_2)_2$heterocyclyl;
$R^3$ represents hydrogen;
$R^4$ represents hydrogen, cyano or $C_{1-6}$alkyl;
Z represents O; or when $R^4$ represents hydrogen and A is a group selected from (i) or (ii) and wherein $R^x$ represents 0, Z may additionally represent NH;
$R^5$ represents hydrogen or $C_{1-6}$alkoxy;
$R^6$ represents hydrogen or $C_{1-6}$alkyl;

m represents 1, 2 or 3; and
n represents 0, 1 or 2
p represents 0, 1 or 2.

2. A compound or a salt thereof according to claim 1 which is a compound of formula (IA)

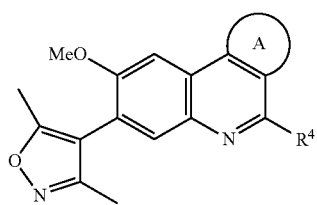

(IA)

wherein A and $R^4$ are as defined for formula (I).

3. A compound or a salt thereof according to claim 2 in which $R^4$ is hydrogen and A is a group of formula (I) or (ii) wherein n is 1.

4. A compound or a salt thereof according to claim 1 in which A is a group of formula (II) wherein $R^{2b}$ represents $(CH_2)_2C_{1-6}$alkoxy.

5. A compound or a salt thereof according to claim 1 which is a compound of formula (IB)

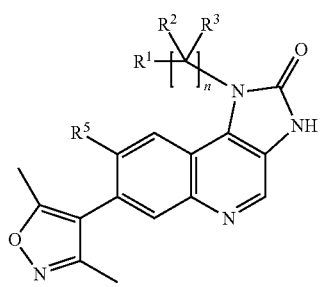

(IB)

wherein $R^1$, $R^2$, $R^3$, $R^5$ and n are as defined for compounds of formula (I).

6. A compound or a salt thereof according to claim 5 in which $R^5$ is —$OCH_3$.

7. A compound or a salt thereof according to claim 1 which is a compound of formula (1C)

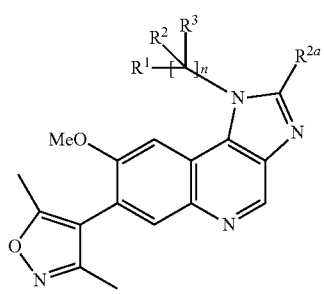

(IC)

wherein $R^1$, $R^2$, $R^3$, $R^{2a}$ and n are defined above for compounds of formula (I).

8. A compound or a salt thereof according to claim 7 in which $R^{2a}$ represents H, $C_{1-3}$alkyl, $(CH_2)_m$OH, $(CH_2)_m C_{1-3}$alkoxy, $(CH_2)_m NR^a R^b$ or $(CHR^6)_p$heterocyclyl, wherein $R^a$ represents H, $C_{1-3}$alkyl, or heterocyclyl;

$R^b$ represents H or $C_{1-3}$alkyl, or $R^a$ and $R^b$ together with the N to which they are attached form a 5 or 6 membered heterocyclyl;

$R^6$ represents H or $C_{1-3}$alkyl;

m represents 1, 2 or 3; and p represents 0, 1, 2.

9. A compound or a salt thereof according to claim 7 in which $R^{2a}$ is tetrahydropyranyl.

10. A compound or a salt thereof according to claim 1 in which n is 1.

11. A compound or a salt thereof according to claim 1 in which $R^2$ is hydrogen or methyl.

12. A compound or a salt thereof according claim 1 in which $R^1$ represents a heteroaromatic group optionally substituted by one or two groups selected from hydroxy, $C_{1-3}$alkyl, $C_{1-3}$alkoxy, hydroxy$C_{1-4}$-alkyl and $C_{1-4}$alkoxy$C_{1-4}$alkyl.

13. A compound or a salt thereof according to claim 12 in which the heteroaromatic group is pyridyl.

14. A compound or a salt thereof according to claim 12 in which the heteroaromatic group is selected from furanyl, thienyl, isoxazolyl, thiazolyl, pyrazolyl, pyrazinyl and pyrimidinyl.

15. A compound which is any of one of Examples 1-226 or a salt thereof.

16. A compound which is 7-(3,5-dimethyl-4-isoxazolyl)-8-(methyloxy)-1-[(1R)-1-(2-pyridinyl)ethyl]-1,3-dihydro-2H-imidazo[4,5-c]quinolin-2-one

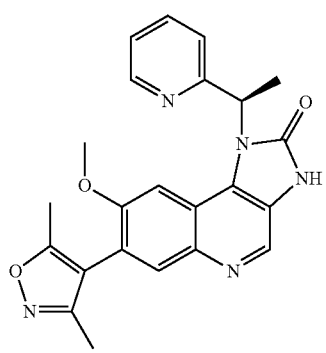 [SMILES: COc1cc2c(cc1-c1c(C)noc1C)ncc1[nH]c(=O)n([C@H](C)c3ccccn3)c12]

or a salt thereof.

17. A pharmaceutical composition which comprises a compound or a salt thereof as defined in claim 1 and one or more pharmaceutically acceptable carriers, diluents or excipients.

* * * * *